United States Patent [19]

Fischer et al.

[11] Patent Number: 5,567,671
[45] Date of Patent: Oct. 22, 1996

[54] SUBSTITUTED 1-H-3-PHENYL-5-CYCLOALKYLPYRROLIDINE-2,4-DIONES, THEIR PREPARATION AND THEIR USE

[75] Inventors: Reiner Fischer, Monheim; Thomas Bretschneider, Siegburg; Bernd-Wieland Krüger, Bergisch Gladbach; Hans-Joachim Santel, Leverkusen; Markus Dollinger, Leichlingen; Andreas Turberg, Erkrath; Ulrike Wachendorff-Neumann, Monheim, all of Germany

[73] Assignee: Bayer Aktiengesellschaft, Leverkusen, Germany

[21] Appl. No.: 200,139

[22] Filed: Feb. 22, 1994

[30] Foreign Application Priority Data

Mar. 1, 1993 [DE] Germany .................... 43 06 257.1

[51] Int. Cl.⁶ .................... A01N 43/36; C07D 207/22
[52] U.S. Cl. .................... 504/283; 504/225; 504/242; 504/252; 504/266; 544/243; 544/333; 544/141; 548/200; 548/364.1; 548/408; 548/413; 548/517; 548/518; 548/523; 548/544; 548/407; 546/24; 546/278.7
[58] Field of Search .................... 548/413, 408, 548/407, 544, 517, 518, 523, 364.1, 200; 504/283, 252, 242, 225, 266; 546/24, 275, 278, 280, 281; 544/243, 333, 141

[56] References Cited

FOREIGN PATENT DOCUMENTS

| | | | |
|---|---|---|---|
| 415185 | 3/1991 | European Pat. Off. | 548/544 |
| 0456063 | 11/1991 | European Pat. Off. | 548/408 |
| 0521334 | 1/1993 | European Pat. Off. | 548/408 |
| 521334 | 1/1993 | European Pat. Off. | 548/544 |
| 0595130 | 5/1994 | European Pat. Off. | 548/408 |

*Primary Examiner*—Joseph K. McKane
*Attorney, Agent, or Firm*—Sprung Horn Kramer & Woods

[57] ABSTRACT

The present invention relates to 1-H-3-phenyl-5-cyloalkylpyrrolidine-2,4-diones of the formula (I)

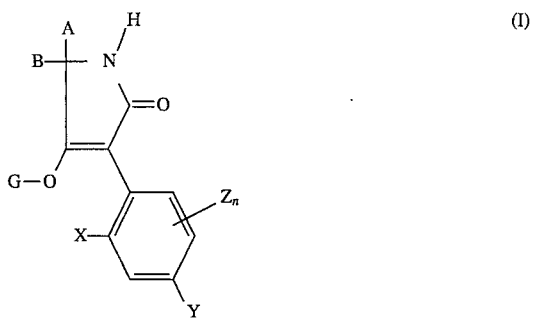

in which
A represents optionally substituted cycloalkyl and
B represents hydrogen or optionally substituted alkyl,
X represents alkyl, halogen or alkoxy,
Y represents hydrogen, alkyl, halogen, alkoxy or halogenoalkyl,
Z represents alkyl, halogen or alkoxy,
n represents a number 0, 1, 2 or 3,
G represents hydrogen (a) or the groups

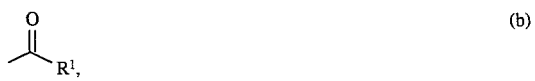

(b)

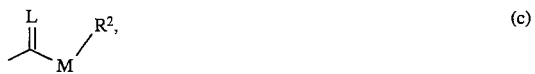

(c)

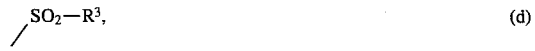

(d)

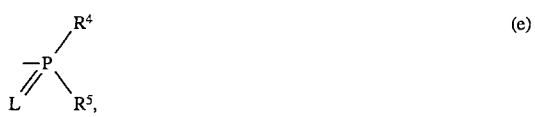

(e)

E (f)

or

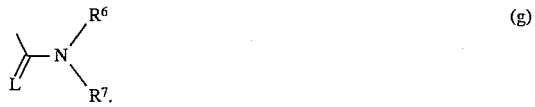

(g)

These compounds possess herbicidal and pesticidal activity.

20 Claims, No Drawings

SUBSTITUTED 1-H-3-PHENYL-5-CYCLOALKYLPYRROLIDINE-2,4-DIONES, THEIR PREPARATION AND THEIR USE

The invention relates to new 1-H-3-phenyl-5-cycloalkylpyrrolidine-2,4-diones, to a plurality of processes for their preparation and to their use as pesticides (in particular as insecticides and acaricides) and as herbicides.

3-Aryl-pyrrolidine-2,4-diones have previously been described as having pharmaceutical properties (S. Suzuki et al. Chem. Pharm. Bull. 15 1120 (1967)). Furthermore, N-phenyl-pyrrolidine-2,4-diones were synthesized by R. Schmierer and H. Mildenberger (Liebigs Ann. Chem. 1985 1095). A biological activity of these compounds has not been described.

EP-A 0,262,399 discloses compounds of a similar structure (3-aryl-pyrrolidine-2,4-diones), from which, however, no herbicidal, insecticidal or acaricidal activity has been disclosed. Unsubstituted, bicyclic 3-aryl-pyrrolidine-2,4-dione derivatives (EP-A 355,599) and (EP 415,211), substituted bicyclic 3-aryl-pyrrolidine-2,4-dione derivatives (EP 501,129) and substituted monocyclic 3-aryl-pyrrolidine-2,4-dione derivatives (EP-A 377,893), (EP 442,077) and (EP 497,127) are known and have a herbicidal, insecticidal or acaricidal activity.

Also known are polycyclic 3-arylpyrrolidine-2,4-dione derivatives (EP 442,073) and 1-H-3-arylpyrrolidine-dione derivatives (EP 456,063) and (EP 521,334).

New 1-H-3-phenyl-5-cycloalkylpyrrolidine-2,4-diones of the formula (I)

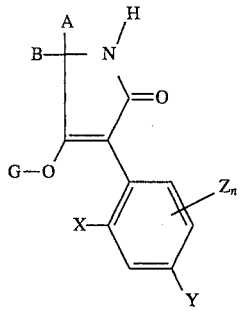

have now been found, in which

A represents optionally substituted cycloalkyl and

B represents hydrogen or optionally substituted alkyl,

X represents alkyl, halogen or alkoxy,

Y represents hydrogen, alkyl, halogen, alkoxy or halogenoalkyl,

Z represents alkyl, halogen or alkoxy, n represents a number 0, 1, 2 or 3,

G represents hydrogen (a) or the groups

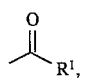 (b)

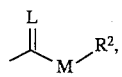 (c)

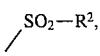 (d)

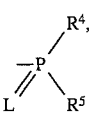 (e)

E (f)

or

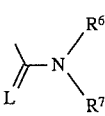 (g)

E represents a metal ion equivalent or an ammonium ion,

L and M represent oxygen and/or sulphur, $R^1$ represents in each case optionally halogen-substituted alkyl, alkenyl, alkoxyalkyl, alkylthioalkyl, polyalkoxyalkyl or cycloalkyl, it being possible for the latter to be interrupted by hetero atoms, or represents optionally substituted phenyl, optionally substituted phenylalkyl, substituted hetaryl, substituted phenoxyalkyl or substituted hetaryloxyalkyl, $R^2$ represents in each case optionally halogen-substituted alkyl, alkenyl, alkoxyalkyl, polyalkoxyalkyl or in each case optionally substituted cycloalkyl, phenyl or benzyl, $R^3$, $R^4$ and $R^5$ independently of one another represent in each case optionally halogen-substituted alkyl, alkoxy, cycloalkyloxy, alkylamino, dialkylamino, alkylthio, alkenylthio or cycloalkylthio and in each case optionally substituted phenyl, phenoxy, benzyloxy or phenylthio, $R^6$ and $R^7$ independently of one another represent hydrogen, in each case optionally halogen-substituted alkyl, alkenyl, alkoxy or alkoxyalkyl, optionally substituted phenyl, optionally substituted benzyl, or together with the N-atom to which they are bound represent a cycle which is optionally interrupted by oxygen or sulphur.

Taking into consideration the various meanings (a), (b), (c), (d), (e), (f) and (g) of group G in the general formula (I), the following main structures (Ia) to (Ig) result:

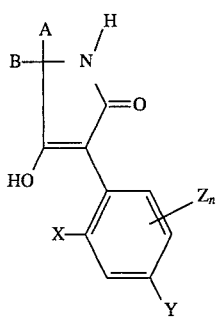 (Ia)

-continued

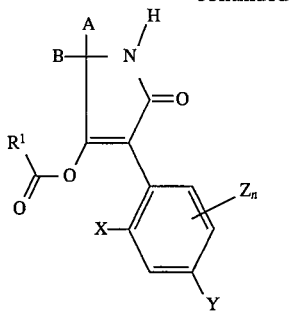
(Ib)

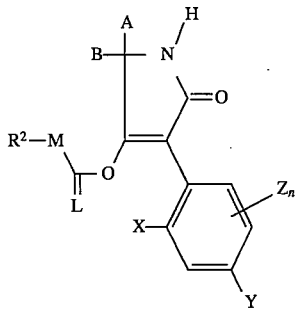
(Ic)

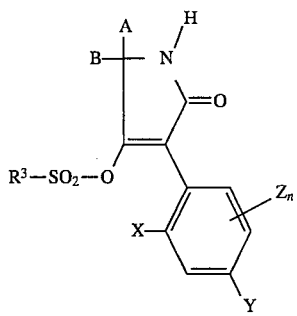
(Id)

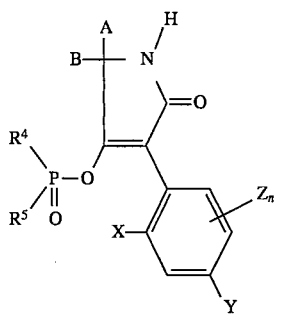
(Ie)

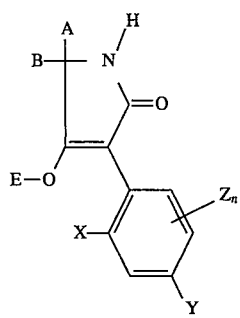
(If)

-continued

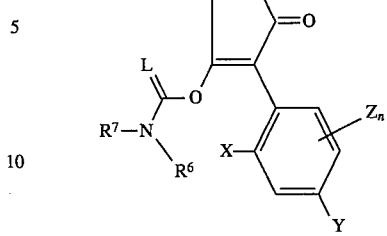
(Ig)

in which

A, B, E, L, M, X, Y, $Z_n$, $R^1$, $R^2$, $R^3$, $R^4$, $R^5$, $R^6$ and $R^7$ have the abovementioned meanings.

Due to one or more centres of chirality, the compounds of the formula (Ia)–(Ig) are generally obtained as a mixture of stereoisomers which, if appropriate, can be separated in the customary manner. They can be used in the form of their diastereomer mixtures and also as pure diastereomers or enantiomers. The following text will always mention compounds of the formula (Ia) to (Ig), for simplicity's sake, even though this is to be understood as meaning the pure compounds and also the mixtures containing various proportions of isomeric, enantiomeric and stereomeric compounds.

Furthermore, it has been found that the new substituted 1-H-3-phenyl-5-cycloalkylpyrrolidine-2,4-diones of the formula (I) are obtained by one of the processes described below.

(A) 1-H-3-phenyl-5-cycloalkylpyrrolidine-2,4-diones or their enols of the formula (Ia)

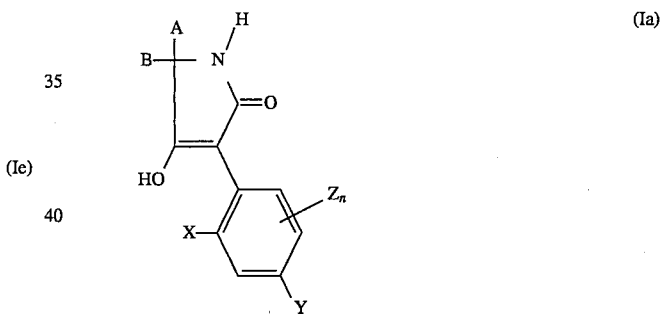
(Ia)

in which

A, B, X, Y, Z and n have the abovementioned meaning, are obtained when

N-acylamino acid esters of the formula (II)

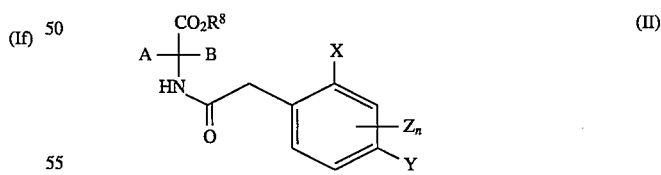
(II)

in which

A, B, X, Y, Z and n have the abovementioned meaning and $R^8$ represents alkyl, are subjected to an intramolecular condensation reaction in the presence of a diluent and in the presence of a base;

or (B) compounds of the formula (Ib)

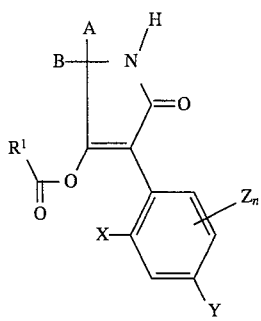
(Ib)

in which

A, B, X, Y, Z, $R^1$ and n have the abovementioned meaning are obtained when compounds of the formula (Ia)

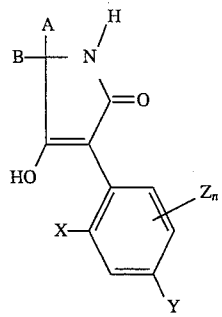
(Ia)

in which

A, B, X, Y, Z and n have the abovementioned meaning, are reacted

α) with acid halides of the general formula (III)

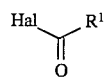
(III)

in which $R^1$ has the abovementioned meaning and

Hal represents halogen, in particular chlorine and bromine, if appropriate in the presence of a diluent and if appropriate in the presence of an acid-binding agent, or β) with carboxylic anhydrides of the general formula (IV)

$R^1$—CO—O—CO—$R^1$  (IV)

in which $R^1$ has the abovementioned meaning, if appropriate in the presence of a diluent and if appropriate in the presence of an acid-binding agent;

or (C) compounds of the formula (Ic-1)

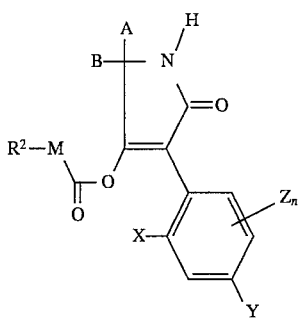
(Ic-1)

in which

A, B, X, Y, Z, $R^2$ and n have the abovementioned meaning and

M represents oxygen or sulphur, are obtained when compounds of the formula (Ia)

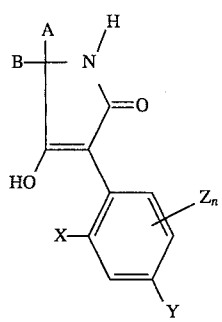
(Ia)

in which

A, B, X, Y, Z and n have the abovementioned meaning, are reacted with chloroformic ester or chloroformic thioester of the general formula (V)

$R^2$—M—CO—Cl  (V)

in which $R^2$ and M have the abovementioned meaning, if appropriate in the presence of a diluent and if appropriate in the presence of an acid-binding agent;

or (D) compounds of the formula (Ic-2)

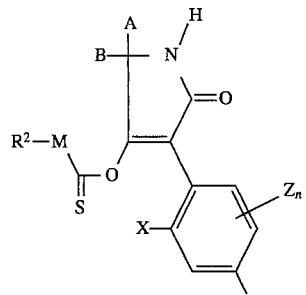
(Ic-2)

in which

A, B, $R^2$, X, Y, Z and n have the abovementioned meaning and

M represents oxygen or sulphur, are obtained when compounds of the formula (Ia)

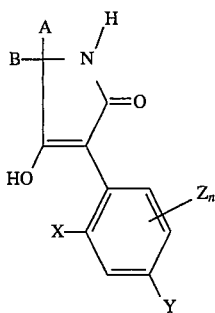

in which

A, B, X, Y, Z and n have the abovementioned meaning, are reacted

α) with chloromonothioformic esters or chlorodithioformic esters of the general formula (VI)

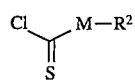

in which

M and $R^2$ have the abovementioned meaning, if appropriate in the presence of a diluent and if appropriate in the presence of an acid-binding agent, or β) with carbon disulphide and subsequently with alkyl halides of the general formula (VII)

in which $R^2$ has the abovementioned meaning and

Hal represents chlorine, bromine or iodine, if appropriate in the presence of a diluent; or (E) compounds of the formula (Id)

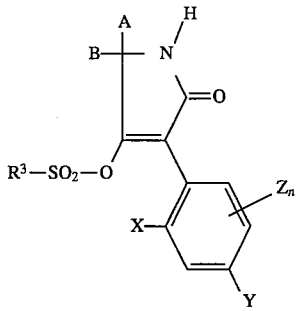

in which

A, B, X, Y, Z, $R^3$ and n have the abovementioned meaning, are obtained when compounds of the formula (Ia)

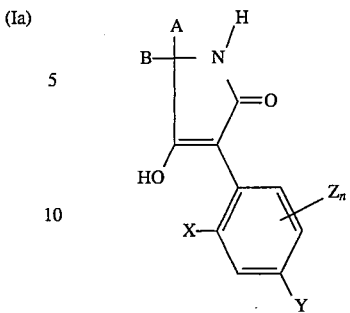

in which

A, B, X, Y, Z and n have the abovementioned meaning, are reacted with sulphonyl chlorides of the general formula (VIII)

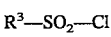

in which $R^3$ has the abovementioned meaning, if appropriate in the presence of a diluent and if appropriate in the presence of an acid-binding agent;

or (F) compounds of the formula (Ie)

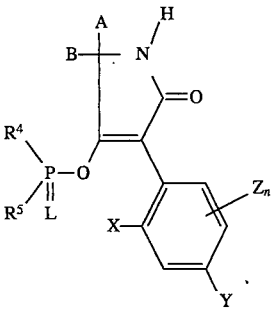

in which

A, B, L, X, Y, Z, $R^4$, $R^5$ and n have the abovementioned meaning, are obtained when 1-H-3-aryl-pyrrolidine-2,4-diones of the formula (Ia) or their enols

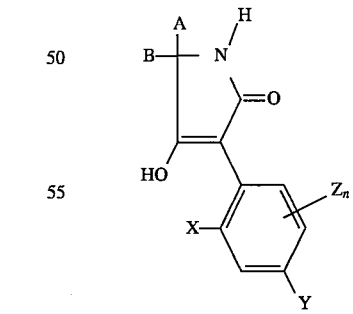

in which

A, B, X, Y, Z and n have the abovementioned meaning, are reacted with phosphorus compounds of the general formula (IX)

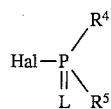 (IX)

in which

L, $R^4$ and $R^5$ have the abovementioned meaning and Hal represents halogen, in particular chlorine or bromine, if appropriate in the presence of a diluent and if appropriate in the presence of an acid-binding agent;

or (G) compounds of the formula (If)

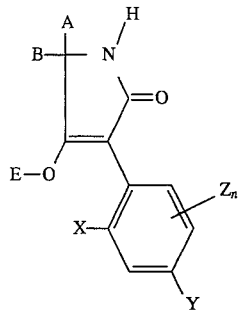 (I-f)

in which

A, B, X, Y, Z and n have the abovementioned meaning, and

E represents a metal ion equivalent or an ammonium ion, are obtained when compounds of the formula (Ia)

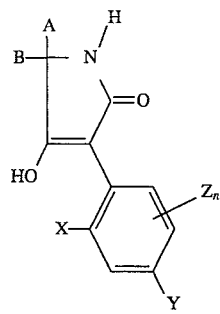 (Ia)

in which

A, B, X, Y, Z and n have the abovementioned meaning, are reacted with metal hydroxides or amines of the general formulae (X) and (XI)

Me OH$_t$ (X)

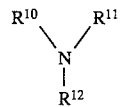 (XI)

in which

Me represents mono- or divalent metal ions, t represents the number 1 or 2 and $R^{10}$, $R^{11}$ and $R^{12}$ independently of one another represent hydrogen and alkyl, if appropriate in the presence of a diluent.

(H) Furthermore, it has been found that compounds of the formula (I)

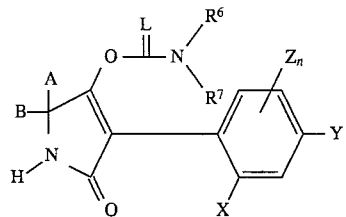 (Ig)

in which

A, B, L, X, Y, Z, $R^6$, $R^7$ and n have the abovementioned meaning, are obtained when compounds of the formula (Ia)

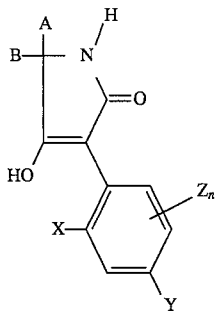 (Ia)

in which

A, B, X, Y, Z and n have the abovementioned meaning, are reacted

α) with compounds of the general formula (XII)

$R^6$—N=C=L (XII)

in which

L and $R^6$ have the abovementioned meaning, if appropriate in the presence of a diluent and if appropriate in the presence of a catalyst or β) with carbamoyl chlorides or thiocarbamoyl chlorides of the general formula (XIII)

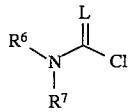 (XIII)

in which

L, $R^6$ and $R^7$ have the abovementioned meaning, if appropriate in the presence of a diluent and if appropriate in the presence of an acid-binding agent.

Furthermore, it has been found that the new 1-H-3-phenyl-5-cycloalkylpyrrolidine-2,4-diones of the formula (I) are distinguished by outstanding insecticidal, acaricidal and herbicidal activities.

The following applies to the general formulae of the present application:

A preferably represents $C_3$–$C_{10}$-cycloalkyl which is optionally substituted by halogen, $C_1$–$C_6$-alkyl, $C_1$–$C_6$-alkoxy, $C_1$–$C_4$-halogenoalkyl or $C_1$–$C_4$-halogenoalkoxy, B preferably represents hydrogen or optionally halogen-substituted straight-chain or branched alkyl, A particularly preferably represents $C_3$–$C_8$-cycloalkyl which is optionally substituted by fluorine, chlorine, $C_1$–$C_5$-alkyl, $C_1$–$C_5$-alkoxy, $C_1$–$C_2$-halogenoalkyl or $C_1$–$C_2$-halogenoalkoxy, B particularly preferably represents hydrogen or straight-chain or branched $C_1$–$C_6$-alkyl which is optionally substituted by chlorine or fluorine.

A very particularly preferably represents $C_3$–$C_6$-cycloalkyl which is optionally substituted by fluorine, methyl, ethyl, propyl, i-propyl, butyl, i-butyl, s-butyl, t-butyl, methoxy, ethoxy, propoxy, i-propoxy, trifluoromethyl or trifluoromethoxy, B very particularly preferably represents hydrogen or methyl, ethyl, propyl, i-propyl, butyl, i-butyl, s-butyl or t-butyl, each of which is optionally substituted by fluorine.

X preferably represents $C_1$–$C_6$-alkyl, halogen or $C_1$–$C_6$-alkoxy.

X particularly preferably represents $C_1$–$C_4$-alkyl, halogen or $C_1$–$C_4$-alkoxy.

X very particularly preferably represents methyl, ethyl, propyl, i-propyl, fluorine, chlorine, bromine, methoxy or ethoxy.

Y preferably represents hydrogen, $C_1$–$C_6$-alkyl, halogen, $C_1$–$C_6$-alkoxy or $C_1$–$C_3$-halogenoalkyl.

Y particularly preferably represents hydrogen, $C_1$–$C_4$-alkyl, halogen, $C_1$–$C_4$-alkoxy or $C_1$–$C_2$-halogenoalkyl.

Y very particularly preferably represents hydrogen, methyl, ethyl, propyl, i-propyl, butyl, i-butyl, tert.-butyl, fluorine, chlorine, bromine, methoxy, ethoxy or trifluoromethyl.

Z preferably represents $C_1$–$C_6$-alkyl, halogen or $C_1$–$C_6$-alkoxy.

Z particularly preferably represents $C_1$–$C_4$-alkyl, halogen or $C_1$–$C_4$-alkoxy.

Z very particularly preferably represents methyl, ethyl, propyl, i-propyl, butyl, i-butyl, tert.-butyl, fluorine, chlorine, bromine, methoxy or ethoxy.

G preferably represents hydrogen (a) or the groups

 (b)

 (c)

 (d)

 (e)

E (f)

or

 (g)

in which

E in each case represents a metal ion equivalent or an ammonium ion and

L and M in each case represent oxygen and/or sulphur, $R^1$ represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_2$–$C_8$-alkyl or cycloalkyl having 3 to 8 ring atoms, it being possible for the latter to be interrupted by oxygen and/or sulphur atoms, or represents phenyl which is optionally substituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or -$C_1$–$C_6$-alkylsulphonyl, or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which is optionally substituted by halogen and/or $C_1$–$C_6$-alkyl, or represents phenoxy-$C_1$–$C_6$-alkyl which is optionally substituted by halogen and/or $C_1$–$C_6$-alkyl, or represents hetaryloxy-$C_1$–$C_6$-alkyl which is optionally substituted by halogen, amino and/or $C_1$–$C_6$-alkyl, $R^2$ represents in each case optionally halogen-substituted $C_1$–$C_{20}$-alkyl, $C_3$–$C_{20}$-alkenyl, $C_1$–$C_8$-alkoxy-$C_2$–$C_8$-alkyl or $C_1$–$C_8$-polyalkoxy-$C_2$–$C_8$-alkyl, or represents $C_3$–$C_8$-cycloalkyl which is optionally substituted by halogen, $C_1$–$C_6$-alkyl, $C_1$–$C_6$-alkoxy and/or $C_1$–$C_6$-alkylthio, or represents phenyl or benzyl, each of which is optionally substituted by halogen, nitro, $C_1$–$C_6$-alkyl, $C_1$–$C_6$-alkoxy or $C_1$–$C_6$-halogenoalkyl, $R^3$, $R^4$ and $R^5$ independently of one another represent in each case optionally halogen-substituted $C_1$–$C_8$-alkyl, $C_1$–$C_8$-alkoxy, $C_3$–$C_7$-cycloalkyloxy, $C_1$–$C_8$-alkylamino, Di-($C_1$–$C_8$)-alkylamino $C_1$–$C_8$-alkylthio, $C_3$–$C_8$-alkenylthio or $C_3$–$C_7$-cycloalkylthio, or represent phenyl, phenoxy, benzyloxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen or represent in each case optionally halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-alkyl, $C_1$–$C_8$-halogenoalkyl or $C_1$–$C_8$-alkoxy, or together with the N-atom to which they are bound represent a ring having 3–6 atoms which is optionally interrupted by oxygen or sulphur, G particularly preferably represents hydrogen (a) or the groups

 (b)

 (c)

 (d)

 (e)

E (f)

-continued or

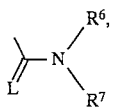

in which

E represents a metal ion equivalent or an ammonium ion,

L and M in each case represent oxygen and/or sulphur, $R^1$ represents in each case optionally halogen-substituted $C_1$–$C_{16}$-alkyl, $C_2$–$C_{16}$-alkenyl, $C_1$–$C_6$-alkoxy-$C_1$–$C_6$-alkyl, $C_1$–$C_{16}$-alkylthio-$C_1$ _$C_6$-alkyl, $C_1$–$C_6$-polyalkoxy-$C_2$–$C_6$-alkyl or cycloalkyl having 3 to 7 ring atoms which can be interrupted by 1–2 oxygen and/or sulphur atoms, or represents phenyl which is optionally substituted by halogen, nitro, $C_1$–$C_4$-alkyl, $C_1$–$C_4$-alkoxy, $C_1$–$C_3$-halogenoalkyl, $C_1$–$C_3$-halogenoalkoxy $C_1$–$C_6$-alkylthio or $C_1$–$C_6$-alkylsulphonyl, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, or represents hetaryl which is optionally substituted by fluorine, chlorine, bromine and/or $C_1$–$C_4$-alkyl, or represents phenoxy-$C_1$–$C_5$-alkyl which is optionally substituted by fluorine, chlorine, bromine and/or $C_1$–$C_4$-alkyl, or represents hetaryloxy-$C_1$–$C_5$-alkyl which is optionally substituted by fluorine, chlorine, bromine, amino and/or $C_1$–$C_4$-alkyl, $R^2$ represents in each case optionally halogen-substituted $C_1$–$C_{16}$-alkyl, $C_3$–$C_{16}$-alkenyl, $C_1$–$C_6$-alkoxy-$C_2$–$C_6$-alkyl or $C_1$–$C_6$-polyalkoxy-$C_2$–$C_6$-alkyl, or represents $C_3$–$C_7$-cycloalkyl which is optionally substituted by halogen, $C_1$–$C_4$-alkyl, $C_1$–$C_4$-alkoxy and/or $C_1$–$C_4$-alkylthio, or represents phenyl or benzyl, each of which is optionally substituted by halogen, nitro, $C_1$–$C_4$-alkyl, $C_1$–$C_3$-alkoxy or $C_1$–$C_3$-halogenoalkyl, $R^3$, $R^4$ and $R^5$ independently of one another represent in each case optionally halogen-substituted $C_1$–$C_6$-alkyl, $C_1$–$C_6$-alkoxy, $C_3$–$C_6$-cycloalkyloxy, $C_1$–$C_6$-alkylamino, di-($C_1$–$C_6$-alkylamino, $C_1$–$C_6$-alkylthio, $C_3$–$C_6$-alkenylthio or $C_3$–$C_6$-cycloalkylthio, or represent phenyl, phenoxy, benzyloxy, or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another represent hydrogen, or represent in each case optionally halogen-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together with the N-atom to which they are bound represent a ring having 3–6 C-atoms which is Optionally substituted by oxygen or sulphur, G very particularly preferably represents hydrogen (a) or the groups

 (b)

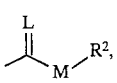 (c)

 (d)

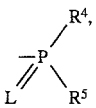 (e)

E (f)

or

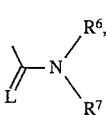 (g)

in which

E represents a metal ion equivalent or an ammonium ion and

L and M represent oxygen and/or sulphur, $R^1$ represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_2$–$C_4$-alkyl or cycloalkyl having 3 to 6 ring atoms which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy, nitro, methylthio, ethylthio, methylsulphonyl or ethylsulphonyl, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents furanoyl, thienyl, pyridyl, pyrimidyl, thiazolyl and pyrazolyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl and thiazolyloxy-$C_1$–$C_4$-alkyl, each of which is optionally substituted by fluorine, chlorine, amino, methyl or ethyl, represents $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, each of which is optionally substituted by fluorine or chlorine, or represents $C_3$–$C_6$-cycloalkyl which is optionally substituted by fluorine, chlorine, methyl, ethyl, propyl, methoxy, ethoxy, methylthio or ethylthio, or represents phenyl or benzyl, each of which is optionally substituted by fluorine, chlorine, nitro, methyl, ethyl, propyl, i-propyl, methoxy, ethoxy or trifluoromethyl, $R^3$, $R^4$ and $R^5$ independently of one another represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, each of which is optionally substituted by fluorine or chlorine, or represent phenyl, phenoxy, benzyloxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-alkylthio, $C_1$–$C_2$-fluoroalkylthio or $C_1$–$C_3$-alkyl.

$R^6$ and $R^7$ independently of one another represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine, chlorine or bromine, or represent phenyl which is optionally substituted by fluorine, chlorine, bromine, $C_1$–$C_4$-halogenoalkyl, $C_1$–$C_4$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, or together with the N-atom to which they are bound represent a ring having 4–6 C-atoms which is optionally substituted by oxygen or sulphur.

The following compounds of the formula (Ia) may be mentioned individually in addition to the compounds mentioned in the Preparation Examples:

TABLE 1

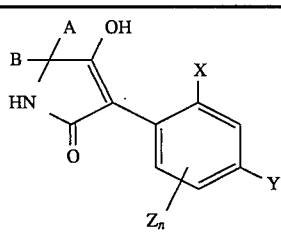
(Ia)

| X | Y | $Z_n$ | A* | B |
|---|---|-------|----|----|
| Cl | Cl | H | $C_3H_5$ | $CH_3$ |
| Cl | H | 6-Cl | $C_3H_5$ | $CH_3$ |
| Cl | H | 6-F | $C_3H_5$ | $CH_3$ |
| $CH_3$ | $CH_3$ | H | $C_3H_5$ | $CH_3$ |
| $CH_3$ | $CH_3$ | 6-$CH_3$ | $C_3H_5$ | $CH_3$ |
| Cl | Cl | H | $C_5H_9$ | $CH_3$ |
| Cl | H | 6-Cl | $C_5H_9$ | $CH_3$ |
| Cl | H | 6-F | $C_5H_9$ | $CH_3$ |
| $CH_3$ | $CH_3$ | H | $C_5H_9$ | $CH_3$ |
| $CH_3$ | $CH_3$ | 6-$CH_3$ | $C_5H_9$ | $CH_3$ |
| Cl | Cl | H | $C_6H_{11}$ | $CH_3$ |
| Cl | H | 6-Cl | $C_6H_{11}$ | $CH_3$ |
| Cl | H | 6-F | $C_6H_{11}$ | $CH_3$ |
| $CH_3$ | $CH_3$ | H | $C_6H_{11}$ | $CH_3$ |
| $CH_3$ | $CH_3$ | 6-$CH_3$ | $C_6H_{11}$ | $CH_3$ |

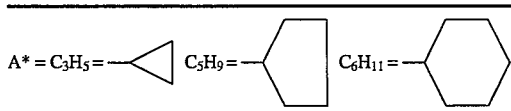

The following compounds of the formula (Ib) may be mentioned individually in addition to the compounds mentioned in the Preparation Examples:

TABLE 2

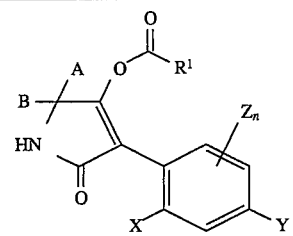
(Ib)

| A* | B | X | Y | $Z_n$ | $R^1$ |
|----|----|----|----|------|------|
| $C_3H_5$ | $CH_3$ | Cl | Cl | H | $CH_3$ |
| $C_3H_5$ | $CH_3$ | Cl | Cl | H | $C_2H_5-$ |
| $C_3H_5$ | $CH_3$ | Cl | Cl | H | $C_3H_7-$ |
| $C_3H_5$ | $CH_3$ | Cl | Cl | H | $i$-$C_3H_7-$ |
| $C_3H_5$ | $CH_3$ | Cl | Cl | H | $C_4H_9-$ |
| $C_3H_5$ | $CH_3$ | Cl | Cl | H | $i$-$C_4H_9-$ |
| $C_3H_5$ | $CH_3$ | Cl | Cl | H | $t$-$C_4H_9-$ |
| $C_3H_5$ | $CH_3$ | Cl | Cl | H | $H_5C_2-C(CH_3)_2-$ |
| $C_3H_5$ | $CH_3$ | Cl | Cl | H | $i$-$C_3H_7-C(CH_3)_2-$ |
| $C_3H_5$ | $CH_3$ | Cl | Cl | H | $Cl-CH_2-C(CH_3)_2-$ |
| $C_3H_5$ | $CH_3$ | Cl | Cl | H | $H_3C-O-CH_2-C(CH_3)_2-$ |
| $C_3H_5$ | $CH_3$ | Cl | Cl | H | $t$-$C_4H_9-CH_2-$ |
| $C_3H_5$ | $CH_3$ | Cl | Cl | H | $C_4H_9-CH(C_2H_5)-$ |
| $C_3H_5$ | $CH_3$ | Cl | Cl | H | $H_3C-S-CH_2-$ |
| $C_3H_5$ | $CH_3$ | Cl | Cl | H | $(CH_3)_2C=CH-$ |
| $C_3H_5$ | $CH_3$ | Cl | Cl | H | phenyl |
| $C_3H_5$ | $CH_3$ | Cl | Cl | H | 4-Cl-phenyl |
| $C_3H_5$ | $CH_3$ | Cl | Cl | H | 4-$CH_3$-phenyl |
| $C_3H_5$ | $CH_3$ | Cl | Cl | H | 4-$O_2N$-phenyl |
| $C_3H_5$ | $CH_3$ | Cl | Cl | H | 4-$H_3CO$-phenyl |
| $C_3H_5$ | $CH_3$ | Cl | Cl | H | benzyl-CH(CH_3)- |
| $C_3H_5$ | $CH_3$ | $CH_3$ | $CH_3$ | H | $CH_3$ |
| $C_3H_5$ | $CH_3$ | $CH_3$ | $CH_3$ | H | $C_2H_5-$ |
| $C_3H_5$ | $CH_3$ | $CH_3$ | $CH_3$ | H | $C_3H_7-$ |
| $C_3H_5$ | $CH_3$ | $CH_3$ | $CH_3$ | H | $i$-$C_3H_7-$ |
| $C_3H_5$ | $CH_3$ | $CH_3$ | $CH_3$ | H | $C_4H_9-$ |
| $C_3H_5$ | $CH_3$ | $CH_3$ | $CH_3$ | H | $i$-$C_4H_9-$ |
| $C_3H_5$ | $CH_3$ | $CH_3$ | $CH_3$ | H | $t$-$C_4H_9-$ |
| $C_3H_5$ | $CH_3$ | $CH_3$ | $CH_3$ | H | $H_5C_2-C(CH_3)_2-$ |
| $C_3H_5$ | $CH_3$ | $CH_3$ | $CH_3$ | H | $i$-$C_3H_7-C(CH_3)_2-$ |
| $C_3H_5$ | $CH_3$ | $CH_3$ | $CH_3$ | H | $Cl-CH_2-C(CH_3)_2-$ |
| $C_3H_5$ | $CH_3$ | $CH_3$ | $CH_3$ | H | $H_3C-O-CH_2-C(CH_3)_2-$ |
| $C_3H_5$ | $CH_3$ | $CH_3$ | $CH_3$ | H | $t$-$C_4H_9-CH_2-$ |

TABLE 2-continued

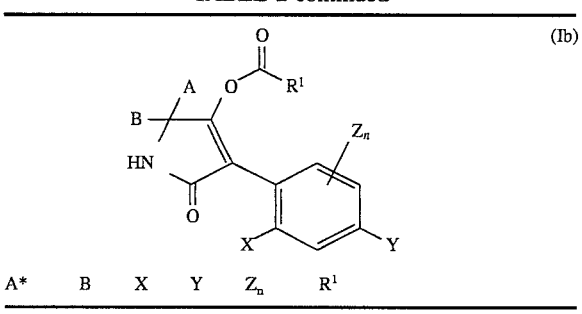

(Ib)

| A* | B | X | Y | Zn | R1 |
|---|---|---|---|---|---|
| C3H5 | CH3 | CH3 | CH3 | H | C4H9—CH(C2H5)— |
| C3H5 | CH3 | CH3 | CH3 | H | H3C—S—CH2— |
| C3H5 | CH3 | CH3 | CH3 | H | (CH3)2C=CH— |
| C3H5 | CH3 | CH3 | CH3 | H | phenyl |
| C3H5 | CH3 | CH3 | CH3 | H | 4-Cl-phenyl |
| C3H5 | CH3 | CH3 | CH3 | H | 4-CH3-phenyl |
| C3H5 | CH3 | CH3 | CH3 | H | 4-O2N-phenyl |
| C3H5 | CH3 | CH3 | CH3 | H | 4-H3CO-phenyl |
| C3H5 | CH3 | CH3 | CH3 | H | 4-ethyl-phenyl |
| C3H5 | CH3 | CH3 | CH3 | 6-CH3 | CH3 |
| C3H5 | CH3 | CH3 | CH3 | 6-CH3 | C2H5— |
| C3H5 | CH3 | CH3 | CH3 | 6-CH3 | C3H7— |
| C3H5 | CH3 | CH3 | CH3 | 6-CH3 | i-C3H7— |
| C3H5 | CH3 | CH3 | CH3 | 6-CH3 | C4H9— |
| C3H5 | CH3 | CH3 | CH3 | 6-CH3 | i-C4H9— |
| C3H5 | CH3 | CH3 | CH3 | 6-CH3 | t-C4H9— |
| C3H5 | CH3 | CH3 | CH3 | 6-CH3 | H5C2—C(CH3)2— |
| C3H5 | CH3 | CH3 | CH3 | 6-CH3 | i-C3H7—C(CH3)2— |
| C3H5 | CH3 | CH3 | CH3 | 6-CH3 | Cl—CH2—C(CH3)2— |
| C3H5 | CH3 | CH3 | CH3 | 6-CH3 | H3C—O—CH2—C(CH3)2— |
| C3H5 | CH3 | CH3 | CH3 | 6-CH3 | t-C4H9—CH2— |
| C3H5 | CH3 | CH3 | CH3 | 6-CH3 | C4H9—CH(C2H5)— |
| C3H5 | CH3 | CH3 | CH3 | 6-CH3 | H3C—S—CH2— |
| C3H5 | CH3 | CH3 | CH3 | 6-CH3 | (CH3)2C=CH— |
| C3H5 | CH3 | CH3 | CH3 | 6-CH3 | phenyl |
| C3H5 | CH3 | CH3 | CH3 | 6-CH3 | 4-Cl-phenyl |
| C3H5 | CH3 | CH3 | CH3 | 6-CH3 | 4-CH3-phenyl |
| C3H5 | CH3 | CH3 | CH3 | 6-CH3 | 4-O2N-phenyl |
| C3H5 | CH3 | CH3 | CH3 | 6-CH3 | 4-H3CO-phenyl |
| C3H5 | CH3 | CH3 | CH3 | 6-CH3 | 4-ethyl-phenyl |
| C5H9 | CH3 | Cl | Cl | H | CH3 |
| C5H9 | CH3 | Cl | Cl | H | C2H5— |
| C5H9 | CH3 | Cl | Cl | H | C3H7— |
| C5H9 | CH3 | Cl | Cl | H | i-C3H7— |
| C5H9 | CH3 | Cl | Cl | H | C4H9— |
| C5H9 | CH3 | Cl | Cl | H | i-C4H9— |
| C5H9 | CH3 | Cl | Cl | H | t-C4H9— |
| C5H9 | CH3 | Cl | Cl | H | H5C2—C(CH3)2— |
| C5H9 | CH3 | Cl | Cl | H | i-C3H7—C(CH3)2— |
| C5H9 | CH3 | Cl | Cl | H | Cl—CH2—C(CH3)2— |
| C5H9 | CH3 | Cl | Cl | H | H3C—O—CH2—C(CH3)2— |
| C5H9 | CH3 | Cl | Cl | H | t-C4H9—CH2— |
| C5H9 | CH3 | Cl | Cl | H | C4H9—CH(C2H5)— |
| C5H9 | CH3 | Cl | Cl | H | H3C—S—CH2— |
| C5H9 | CH3 | Cl | Cl | H | (CH3)2C=CH— |
| C5H9 | CH3 | Cl | Cl | H | phenyl |
| C5H9 | CH3 | Cl | Cl | H | 4-Cl-phenyl |
| C5H9 | CH3 | Cl | Cl | H | 4-CH3-phenyl |

TABLE 2-continued

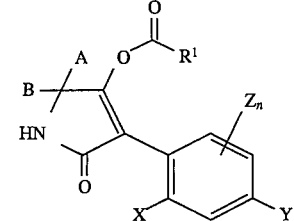

(Ib)

| A* | B | X | Y | Z$_n$ | R$^1$ |
|---|---|---|---|---|---|
| C$_5$H$_9$ | CH$_3$ | Cl | Cl | H |  O$_2$N— |
| C$_5$H$_9$ | CH$_3$ | Cl | Cl | H | 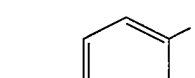 H$_3$CO— |
| C$_5$H$_9$ | CH$_3$ | Cl | Cl | H | 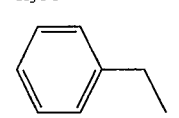 |
| C$_5$H$_9$ | CH$_3$ | CH$_3$ | CH$_3$ | H | CH$_3$ |
| C$_5$H$_9$ | CH$_3$ | CH$_3$ | CH$_3$ | H | C$_2$H$_5$— |
| C$_5$H$_9$ | CH$_3$ | CH$_3$ | CH$_3$ | H | C$_3$H$_7$— |
| C$_5$H$_9$ | CH$_3$ | CH$_3$ | CH$_3$ | H | i-C$_3$H$_7$— |
| C$_5$H$_9$ | CH$_3$ | CH$_3$ | CH$_3$ | H | C$_4$H$_9$— |
| C$_5$H$_9$ | CH$_3$ | CH$_3$ | CH$_3$ | H | i-C$_4$H$_9$— |
| C$_5$H$_9$ | CH$_3$ | CH$_3$ | CH$_3$ | H | t-C$_4$H$_9$— |
| C$_5$H$_9$ | CH$_3$ | CH$_3$ | CH$_3$ | H | H$_5$C$_2$—C(CH$_3$)$_2$— |
| C$_5$H$_9$ | CH$_3$ | CH$_3$ | CH$_3$ | H | i-C$_3$H$_7$—C(CH$_3$)$_2$— |
| C$_5$H$_9$ | CH$_3$ | CH$_3$ | CH$_3$ | H | Cl—CH$_2$—C(CH$_3$)$_2$— |
| C$_5$H$_9$ | CH$_3$ | CH$_3$ | CH$_3$ | H | H$_3$C—O—CH$_2$—C(CH$_3$)$_2$— |
| C$_5$H$_9$ | CH$_3$ | CH$_3$ | CH$_3$ | H | t-C$_4$H$_9$—CH$_2$— |
| C$_5$H$_9$ | CH$_3$ | CH$_3$ | CH$_3$ | H | C$_4$H$_9$—CH(C$_2$H$_5$)— |
| C$_5$H$_9$ | CH$_3$ | CH$_3$ | CH$_3$ | H | H$_3$C—S—CH$_2$— |
| C$_5$H$_9$ | CH$_3$ | CH$_3$ | CH$_3$ | H | (CH$_3$)$_2$C═CH— |
| C$_5$H$_9$ | CH$_3$ | CH$_3$ | CH$_3$ | H | 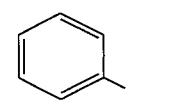 |
| C$_5$H$_9$ | CH$_3$ | CH$_3$ | CH$_3$ | H |  Cl— |
| C$_5$H$_9$ | CH$_3$ | CH$_3$ | CH$_3$ | H |  H$_3$C— |
| C$_5$H$_9$ | CH$_3$ | CH$_3$ | CH$_3$ | H |  O$_2$N— |
| C$_5$H$_9$ | CH$_3$ | CH$_3$ | CH$_3$ | H |  H$_3$CO— |
| C$_5$H$_9$ | CH$_3$ | CH$_3$ | CH$_3$ | H | 6-CH$_3$ | CH$_3$ |
| C$_5$H$_9$ | CH$_3$ | CH$_3$ | CH$_3$ | 6-CH$_3$ | CH$_3$ |
| C$_5$H$_9$ | CH$_3$ | CH$_3$ | CH$_3$ | 6-CH$_3$ | C$_2$H$_5$— |
| C$_5$H$_9$ | CH$_3$ | CH$_3$ | CH$_3$ | 6-CH$_3$ | C$_3$H$_7$— |
| C$_5$H$_9$ | CH$_3$ | CH$_3$ | CH$_3$ | 6-CH$_3$ | i-C$_3$H$_7$— |
| C$_5$H$_9$ | CH$_3$ | CH$_3$ | CH$_3$ | 6-CH$_3$ | C$_4$H$_9$— |
| C$_5$H$_9$ | CH$_3$ | CH$_3$ | CH$_3$ | 6-CH$_3$ | i-C$_4$H$_9$— |
| C$_5$H$_9$ | CH$_3$ | CH$_3$ | CH$_3$ | 6-CH$_3$ | t-C$_4$H$_9$— |
| C$_5$H$_9$ | CH$_3$ | CH$_3$ | CH$_3$ | 6-CH$_3$ | H$_5$C$_2$—C(CH$_3$)$_2$— |
| C$_5$H$_9$ | CH$_3$ | CH$_3$ | CH$_3$ | 6-CH$_3$ | i-C$_3$H$_7$—C(CH$_3$)$_2$— |
| C$_5$H$_9$ | CH$_3$ | CH$_3$ | CH$_3$ | 6-CH$_3$ | Cl—CH$_2$—C(CH$_3$)$_2$— |
| C$_5$H$_9$ | CH$_3$ | CH$_3$ | CH$_3$ | 6-CH$_3$ | H$_3$C—O—CH$_2$—C(CH$_3$)$_2$— |
| C$_5$H$_9$ | CH$_3$ | CH$_3$ | CH$_3$ | 6-CH$_3$ | t-C$_4$H$_9$—CH$_2$— |
| C$_5$H$_9$ | CH$_3$ | CH$_3$ | CH$_3$ | 6-CH$_3$ | C$_4$H$_9$—CH(C$_2$H$_5$)— |
| C$_5$H$_9$ | CH$_3$ | CH$_3$ | CH$_3$ | 6-CH$_3$ | H$_3$C—S—CH$_2$— |
| C$_5$H$_9$ | CH$_3$ | CH$_3$ | CH$_3$ | 6-CH$_3$ | (CH$_3$)$_2$C═CH— |
| C$_5$H$_9$ | CH$_3$ | CH$_3$ | CH$_3$ | 6-CH$_3$ | 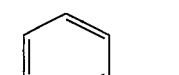 |
| C$_5$H$_9$ | CH$_3$ | CH$_3$ | CH$_3$ | 6-CH$_3$ | 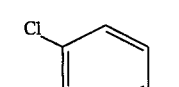 Cl— |
| C$_5$H$_9$ | CH$_3$ | CH$_3$ | CH$_3$ | 6-CH$_3$ | 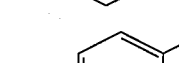 H$_3$C— |
| C$_5$H$_9$ | CH$_3$ | CH$_3$ | CH$_3$ | 6-CH$_3$ | 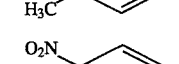 O$_2$N— |
| C$_5$H$_9$ | CH$_3$ | CH$_3$ | CH$_3$ | 6-CH$_3$ | 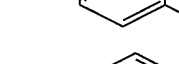 H$_3$CO— |
| C$_5$H$_9$ | CH$_3$ | CH$_3$ | CH$_3$ | 6-CH$_3$ | 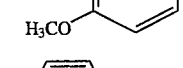 |
| C$_6$H$_{11}$ | CH$_3$ | Cl | Cl | H | CH$_3$ |
| C$_6$H$_{11}$ | CH$_3$ | Cl | Cl | H | C$_2$H$_5$— |
| C$_6$H$_{11}$ | CH$_3$ | Cl | Cl | H | C$_3$H$_7$— |
| C$_6$H$_{11}$ | CH$_3$ | Cl | Cl | H | i-C$_3$H$_7$— |
| C$_6$H$_{11}$ | CH$_3$ | Cl | Cl | H | C$_4$H$_9$— |
| C$_6$H$_{11}$ | CH$_3$ | Cl | Cl | H | i-C$_4$H$_9$— |
| C$_6$H$_{11}$ | CH$_3$ | Cl | Cl | H | t-C$_4$H$_9$— |
| C$_6$H$_{11}$ | CH$_3$ | Cl | Cl | H | H$_5$C$_2$—C(CH$_3$)$_2$— |

TABLE 2-continued

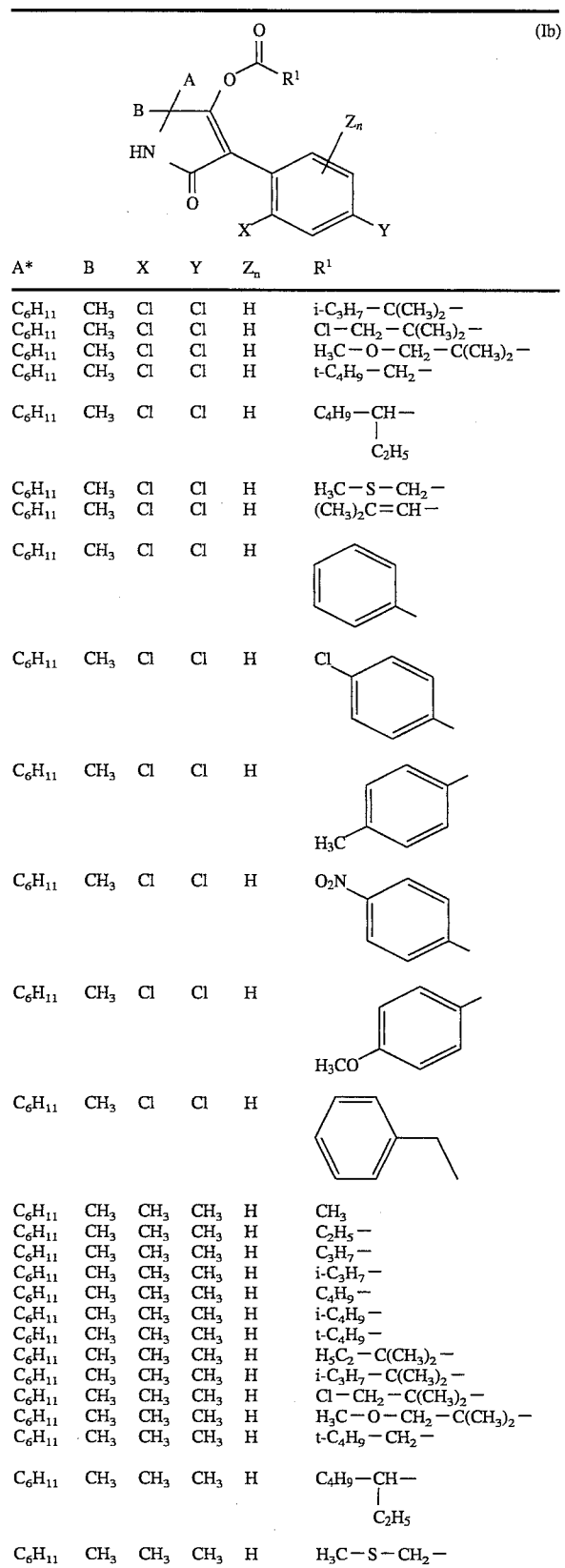

(Ib)

| A* | B | X | Y | $Z_n$ | $R^1$ |
|---|---|---|---|---|---|
| $C_6H_{11}$ | $CH_3$ | Cl | Cl | H | $i\text{-}C_3H_7\text{-}C(CH_3)_2\text{-}$ |
| $C_6H_{11}$ | $CH_3$ | Cl | Cl | H | $Cl\text{-}CH_2\text{-}C(CH_3)_2\text{-}$ |
| $C_6H_{11}$ | $CH_3$ | Cl | Cl | H | $H_3C\text{-}O\text{-}CH_2\text{-}C(CH_3)_2\text{-}$ |
| $C_6H_{11}$ | $CH_3$ | Cl | Cl | H | $t\text{-}C_4H_9\text{-}CH_2\text{-}$ |
| $C_6H_{11}$ | $CH_3$ | Cl | Cl | H | $C_4H_9\text{-}CH(C_2H_5)\text{-}$ |
| $C_6H_{11}$ | $CH_3$ | Cl | Cl | H | $H_3C\text{-}S\text{-}CH_2\text{-}$ |
| $C_6H_{11}$ | $CH_3$ | Cl | Cl | H | $(CH_3)_2C\text{=}CH\text{-}$ |
| $C_6H_{11}$ | $CH_3$ | Cl | Cl | H | phenyl-CH$_2$- |
| $C_6H_{11}$ | $CH_3$ | Cl | Cl | H | 4-Cl-phenyl-CH$_2$- |
| $C_6H_{11}$ | $CH_3$ | Cl | Cl | H | 4-CH$_3$-phenyl-CH$_2$- |
| $C_6H_{11}$ | $CH_3$ | Cl | Cl | H | 4-O$_2$N-phenyl-CH$_2$- |
| $C_6H_{11}$ | $CH_3$ | Cl | Cl | H | 4-H$_3$CO-phenyl-CH$_2$- |
| $C_6H_{11}$ | $CH_3$ | Cl | Cl | H | phenyl-CH(C$_2$H$_5$)- |
| $C_6H_{11}$ | $CH_3$ | $CH_3$ | $CH_3$ | H | $CH_3$ |
| $C_6H_{11}$ | $CH_3$ | $CH_3$ | $CH_3$ | H | $C_2H_5\text{-}$ |
| $C_6H_{11}$ | $CH_3$ | $CH_3$ | $CH_3$ | H | $C_3H_7\text{-}$ |
| $C_6H_{11}$ | $CH_3$ | $CH_3$ | $CH_3$ | H | $i\text{-}C_3H_7\text{-}$ |
| $C_6H_{11}$ | $CH_3$ | $CH_3$ | $CH_3$ | H | $C_4H_9\text{-}$ |
| $C_6H_{11}$ | $CH_3$ | $CH_3$ | $CH_3$ | H | $i\text{-}C_4H_9\text{-}$ |
| $C_6H_{11}$ | $CH_3$ | $CH_3$ | $CH_3$ | H | $t\text{-}C_4H_9\text{-}$ |
| $C_6H_{11}$ | $CH_3$ | $CH_3$ | $CH_3$ | H | $H_5C_2\text{-}C(CH_3)_2\text{-}$ |
| $C_6H_{11}$ | $CH_3$ | $CH_3$ | $CH_3$ | H | $i\text{-}C_3H_7\text{-}C(CH_3)_2\text{-}$ |
| $C_6H_{11}$ | $CH_3$ | $CH_3$ | $CH_3$ | H | $Cl\text{-}CH_2\text{-}C(CH_3)_2\text{-}$ |
| $C_6H_{11}$ | $CH_3$ | $CH_3$ | $CH_3$ | H | $H_3C\text{-}O\text{-}CH_2\text{-}C(CH_3)_2\text{-}$ |
| $C_6H_{11}$ | $CH_3$ | $CH_3$ | $CH_3$ | H | $t\text{-}C_4H_9\text{-}CH_2\text{-}$ |
| $C_6H_{11}$ | $CH_3$ | $CH_3$ | $CH_3$ | H | $C_4H_9\text{-}CH(C_2H_5)\text{-}$ |
| $C_6H_{11}$ | $CH_3$ | $CH_3$ | $CH_3$ | H | $H_3C\text{-}S\text{-}CH_2\text{-}$ |

TABLE 2-continued

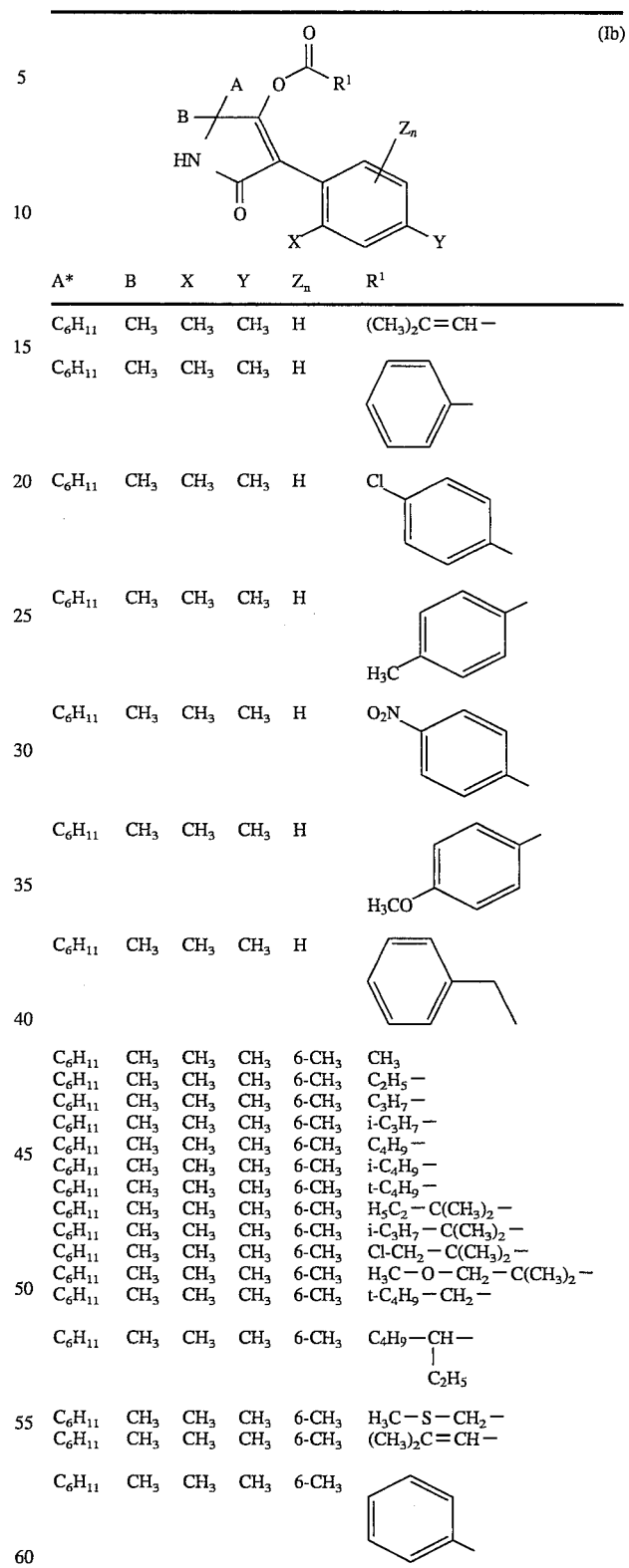

(Ib)

| A* | B | X | Y | $Z_n$ | $R^1$ |
|---|---|---|---|---|---|
| $C_6H_{11}$ | $CH_3$ | $CH_3$ | $CH_3$ | H | $(CH_3)_2C\text{=}CH\text{-}$ |
| $C_6H_{11}$ | $CH_3$ | $CH_3$ | $CH_3$ | H | phenyl-CH$_2$- |
| $C_6H_{11}$ | $CH_3$ | $CH_3$ | $CH_3$ | H | 4-Cl-phenyl-CH$_2$- |
| $C_6H_{11}$ | $CH_3$ | $CH_3$ | $CH_3$ | H | 4-CH$_3$-phenyl-CH$_2$- |
| $C_6H_{11}$ | $CH_3$ | $CH_3$ | $CH_3$ | H | 4-O$_2$N-phenyl-CH$_2$- |
| $C_6H_{11}$ | $CH_3$ | $CH_3$ | $CH_3$ | H | 4-H$_3$CO-phenyl-CH$_2$- |
| $C_6H_{11}$ | $CH_3$ | $CH_3$ | $CH_3$ | H | phenyl-CH(C$_2$H$_5$)- |
| $C_6H_{11}$ | $CH_3$ | $CH_3$ | $CH_3$ | 6-$CH_3$ | $CH_3$ |
| $C_6H_{11}$ | $CH_3$ | $CH_3$ | $CH_3$ | 6-$CH_3$ | $C_2H_5\text{-}$ |
| $C_6H_{11}$ | $CH_3$ | $CH_3$ | $CH_3$ | 6-$CH_3$ | $C_3H_7\text{-}$ |
| $C_6H_{11}$ | $CH_3$ | $CH_3$ | $CH_3$ | 6-$CH_3$ | $i\text{-}C_3H_7\text{-}$ |
| $C_6H_{11}$ | $CH_3$ | $CH_3$ | $CH_3$ | 6-$CH_3$ | $C_4H_9\text{-}$ |
| $C_6H_{11}$ | $CH_3$ | $CH_3$ | $CH_3$ | 6-$CH_3$ | $i\text{-}C_4H_9\text{-}$ |
| $C_6H_{11}$ | $CH_3$ | $CH_3$ | $CH_3$ | 6-$CH_3$ | $t\text{-}C_4H_9\text{-}$ |
| $C_6H_{11}$ | $CH_3$ | $CH_3$ | $CH_3$ | 6-$CH_3$ | $H_5C_2\text{-}C(CH_3)_2\text{-}$ |
| $C_6H_{11}$ | $CH_3$ | $CH_3$ | $CH_3$ | 6-$CH_3$ | $i\text{-}C_3H_7\text{-}C(CH_3)_2\text{-}$ |
| $C_6H_{11}$ | $CH_3$ | $CH_3$ | $CH_3$ | 6-$CH_3$ | $Cl\text{-}CH_2\text{-}C(CH_3)_2\text{-}$ |
| $C_6H_{11}$ | $CH_3$ | $CH_3$ | $CH_3$ | 6-$CH_3$ | $H_3C\text{-}O\text{-}CH_2\text{-}C(CH_3)_2\text{-}$ |
| $C_6H_{11}$ | $CH_3$ | $CH_3$ | $CH_3$ | 6-$CH_3$ | $t\text{-}C_4H_9\text{-}CH_2\text{-}$ |
| $C_6H_{11}$ | $CH_3$ | $CH_3$ | $CH_3$ | 6-$CH_3$ | $C_4H_9\text{-}CH(C_2H_5)\text{-}$ |
| $C_6H_{11}$ | $CH_3$ | $CH_3$ | $CH_3$ | 6-$CH_3$ | $H_3C\text{-}S\text{-}CH_2\text{-}$ |
| $C_6H_{11}$ | $CH_3$ | $CH_3$ | $CH_3$ | 6-$CH_3$ | $(CH_3)_2C\text{=}CH\text{-}$ |
| $C_6H_{11}$ | $CH_3$ | $CH_3$ | $CH_3$ | 6-$CH_3$ | phenyl-CH$_2$- |

TABLE 2-continued $$\text{(Ib)}$$

Structure: A and B on a carbon with O-C(=O)-R¹; HN; C=O; phenyl ring with X, Y, Z_n

| A* | B | X | Y | Z_n | R¹ |
|---|---|---|---|---|---|
| C₆H₁₁ | CH₃ | CH₃ | CH₃ | 6-CH₃ | 4-Cl-C₆H₄ |
| C₆H₁₁ | CH₃ | CH₃ | CH₃ | 6-CH₃ | 4-CH₃-C₆H₄ |
| C₆H₁₁ | CH₃ | CH₃ | CH₃ | 6-CH₃ | 4-O₂N-C₆H₄ |
| C₆H₁₁ | CH₃ | CH₃ | CH₃ | 6-CH₃ | 4-CH₃O-C₆H₄ |
| C₆H₁₁ | CH₃ | CH₃ | CH₃ | 6-CH₃ | 4-ethyl-C₆H₄ |

A* =

C₃H₅ = cyclopropyl, C₅H₉ = cyclopentyl, C₆H₁₁ = cyclohexyl

The following compounds of the formula (Ic) may be mentioned individually in addition to the compounds mentioned in the preparation Examples:

TABLE 3

$$\text{(Ic)}$$

| A* | B | X | Y | Z_n | L | M | R² |
|---|---|---|---|---|---|---|---|
| C₃H₅ | CH₃ | Cl | Cl | H | O | O | CH₃ |
| C₃H₅ | CH₃ | Cl | Cl | H | O | O | C₂H₅— |
| C₃H₅ | CH₃ | Cl | Cl | H | O | O | C₃H₇— |
| C₃H₅ | CH₃ | Cl | Cl | H | O | O | i-C₃H₇— |
| C₃H₅ | CH₃ | Cl | Cl | H | O | O | i-C₄H₉— |
| C₃H₅ | CH₃ | Cl | Cl | H | O | O | s-C₄H₉— |
| C₃H₅ | CH₃ | Cl | Cl | H | O | O | t-C₄H₉— |
| C₃H₇ | CH₃ | Cl | Cl | H | O | O | t-C₄H₉—CH₂— |

TABLE 3-continued $$\text{(Ic)}$$

| A* | B | X | Y | Z_n | L | M | R² |
|---|---|---|---|---|---|---|---|
| C₃H₅ | CH₃ | Cl | Cl | H | O | O | cyclohexyl |
| C₃H₅ | CH₃ | Cl | Cl | H | O | O | phenyl |
| C₃H₅ | CH₃ | Cl | Cl | H | O | O | benzyl (CH₂-phenyl) |
| C₃H₅ | CH₃ | Cl | Cl | H | O | S | CH₃ |
| C₃H₅ | CH₃ | Cl | Cl | H | O | S | C₂H₅— |
| C₃H₅ | CH₃ | Cl | Cl | H | O | S | C₃H₇— |
| C₃H₅ | CH₃ | Cl | Cl | H | O | S | i-C₃H₇— |
| C₃H₅ | CH₃ | Cl | Cl | H | O | S | i-C₄H₉— |
| C₃H₅ | CH₃ | Cl | Cl | H | O | S | s-C₄H₉— |
| C₃H₅ | CH₃ | Cl | Cl | H | O | S | t-C₄H₉— |
| C₃H₅ | CH₃ | Cl | Cl | H | O | S | t-C₄H₉—CH₂— |
| C₃H₅ | CH₃ | CH₃ | CH₃ | H | O | O | CH₃ |
| C₃H₅ | CH₃ | CH₃ | CH₃ | H | O | O | C₂H₅— |
| C₃H₅ | CH₃ | CH₃ | CH₃ | H | O | O | C₃H₇— |
| C₃H₅ | CH₃ | CH₃ | CH₃ | H | O | O | i-C₃H₇— |
| C₃H₅ | CH₃ | CH₃ | CH₃ | H | O | O | i-C₄H₉— |
| C₃H₅ | CH₃ | CH₃ | CH₃ | H | O | O | s-C₄H₉— |
| C₃H₅ | CH₃ | CH₃ | CH₃ | H | O | O | t-C₄H₉— |
| C₃H₅ | CH₃ | CH₃ | CH₃ | H | O | O | t-C₄H₉—CH₂— |
| C₃H₅ | CH₃ | CH₃ | CH₃ | H | O | O | cyclohexyl |
| C₃H₅ | CH₃ | CH₃ | CH₃ | H | O | O | phenyl |
| C₃H₅ | CH₃ | CH₃ | CH₃ | H | O | O | benzyl |
| C₃H₅ | CH₃ | CH₃ | CH₃ | H | O | S | CH₃ |
| C₃H₅ | CH₃ | CH₃ | CH₃ | H | O | S | C₂H₅— |
| C₃H₅ | CH₃ | CH₃ | CH₃ | H | O | S | C₃H₇— |
| C₃H₅ | CH₃ | CH₃ | CH₃ | H | O | S | i-C₃H₇— |
| C₃H₅ | CH₃ | CH₃ | CH₃ | H | O | S | i-C₄H₉— |
| C₃H₅ | CH₃ | CH₃ | CH₃ | H | O | S | s-C₄H₉— |
| C₃H₅ | CH₃ | CH₃ | CH₃ | H | O | S | t-C₄H₉— |
| C₃H₅ | CH₃ | CH₃ | CH₃ | H | O | S | t-C₄H₉—CH₂— |
| C₃H₅ | CH₃ | CH₃ | CH₃ | 6-CH₃ | O | O | CH₃ |
| C₃H₅ | CH₃ | CH₃ | CH₃ | 6-CH₃ | O | O | C₂H₅— |
| C₃H₅ | CH₃ | CH₃ | CH₃ | 6-CH₃ | O | O | C₃H₇— |
| C₃H₅ | CH₃ | CH₃ | CH₃ | 6-CH₃ | O | O | i-C₃H₇— |
| C₃H₅ | CH₃ | CH₃ | CH₃ | 6-CH₃ | O | O | i-C₄H₉— |
| C₃H₅ | CH₃ | CH₃ | CH₃ | 6-CH₃ | O | O | s-C₄H₉— |
| C₃H₅ | CH₃ | CH₃ | CH₃ | 6-CH₃ | O | O | t-C₄H₉— |
| C₃H₅ | CH₃ | CH₃ | CH₃ | 6-CH₃ | O | O | t-C₄H₉—CH₂— |

TABLE 3-continued

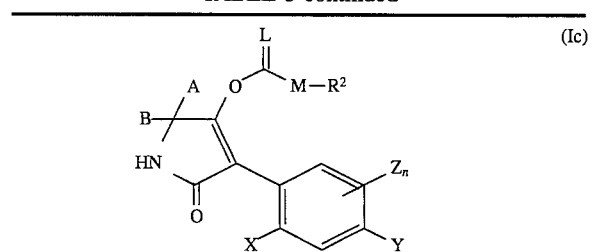

(Ic)

| A* | B | X | Y | $Z_n$ | L | M | $R^2$ |
|---|---|---|---|---|---|---|---|
| $C_3H_5$ | $CH_3$ | $CH_3$ | $CH_3$ | 6-$CH_3$ | O | O | cyclohexyl |
| $C_3H_5$ | $CH_3$ | $CH_3$ | $CH_3$ | 6-$CH_3$ | O | O | phenyl |
| $C_3H_5$ | $CH_3$ | $CH_3$ | $CH_3$ | 6-$CH_3$ | O | O | benzyl |
| $C_3H_5$ | $CH_3$ | $CH_3$ | $CH_3$ | 6-$CH_3$ | O | S | $CH_3$ |
| $C_3H_5$ | $CH_3$ | $CH_3$ | $CH_3$ | 6-$CH_3$ | O | S | $C_2H_5-$ |
| $C_3H_5$ | $CH_3$ | $CH_3$ | $CH_3$ | 6-$CH_3$ | O | S | $C_3H_7-$ |
| $C_3H_5$ | $CH_3$ | $CH_3$ | $CH_3$ | 6-$CH_3$ | O | S | $i-C_3H_7-$ |
| $C_3H_5$ | $CH_3$ | $CH_3$ | $CH_3$ | 6-$CH_3$ | O | S | $i-C_4H_9-$ |
| $C_3H_5$ | $CH_3$ | $CH_3$ | $CH_3$ | 6-$CH_3$ | O | S | $s-C_4H_9-$ |
| $C_3H_5$ | $CH_3$ | $CH_3$ | $CH_3$ | 6-$CH_3$ | O | S | $t-C_4H_9-$ |
| $C_3H_5$ | $CH_3$ | $CH_3$ | $CH_3$ | 6-$CH_3$ | O | S | $t-C_4H_9-CH_2-$ |
| $C_5H_9$ | $CH_3$ | Cl | Cl | H | O | O | $CH_3$ |
| $C_5H_9$ | $CH_3$ | Cl | Cl | H | O | O | $C_2H_5-$ |
| $C_5H_9$ | $CH_3$ | Cl | Cl | H | O | O | $C_3H_7-$ |
| $C_5H_9$ | $CH_3$ | Cl | Cl | H | O | O | $i-C_3H_7-$ |
| $C_5H_9$ | $CH_3$ | Cl | Cl | H | O | O | $i-C_4H_9-$ |
| $C_5H_9$ | $CH_3$ | Cl | Cl | H | O | O | $s-C_4H_9-$ |
| $C_5H_9$ | $C-C_5H_9$ | Cl | Cl | H | O | O | $t-C_4H_9-$ |
| $C_5H_9$ | $CH_3$ | Cl | Cl | H | O | O | $t-C_4H_9-CH_2-$ |
| $C_5H_9$ | $CH_3$ | Cl | Cl | H | O | O | cyclohexyl |
| $C_5H_9$ | $CH_3$ | Cl | Cl | H | O | O | phenyl |
| $C_5H_9$ | $CH_3$ | Cl | Cl | H | O | O | benzyl |
| $C_5H_9$ | $CH_3$ | Cl | Cl | H | O | S | $CH_3$ |
| $C_5H_9$ | $CH_3$ | Cl | Cl | H | O | S | $C_2H_5-$ |
| $C_5H_9$ | $CH_3$ | Cl | Cl | H | O | S | $C_3H_7-$ |
| $C_5H_9$ | $CH_3$ | Cl | Cl | H | O | S | $i-C_3H_7-$ |
| $C_5H_9$ | $CH_3$ | Cl | Cl | H | O | S | $i-C_4H_9-$ |
| $C_5H_9$ | $CH_3$ | Cl | Cl | H | O | S | $s-C_4H_9-$ |
| $C_5H_9$ | $CH_3$ | Cl | Cl | H | O | S | $t-C_4H_9-$ |
| $C_5H_9$ | $CH_3$ | Cl | Cl | H | O | S | $t-C_4H_9-CH_2-$ |
| $C_5H_9$ | $CH_3$ | $CH_3$ | $CH_3$ | H | O | O | $CH_3$ |
| $C_5H_9$ | $CH_3$ | $CH_3$ | $CH_3$ | H | O | O | $C_2H_5-$ |
| $C_5H_9$ | $CH_3$ | $CH_3$ | $CH_3$ | H | O | O | $C_3H_7$ |
| $C_5H_9$ | $CH_3$ | $CH_3$ | $CH_3$ | H | O | O | $i-C_3H_7-$ |
| $C_5H_9$ | $CH_3$ | $CH_3$ | $CH_3$ | H | O | O | $i-C_4H_9-$ |
| $C_5H_9$ | $CH_3$ | $CH_3$ | $CH_3$ | H | O | O | $s-C_4H_9-$ |
| $C_5H_9$ | $CH_3$ | $CH_3$ | $CH_3$ | H | O | O | $t-C_4H_9-$ |
| $C_5H_9$ | $CH_3$ | $CH_3$ | $CH_3$ | H | O | O | $t-C_4H_9-CH_2-$ |

TABLE 3-continued

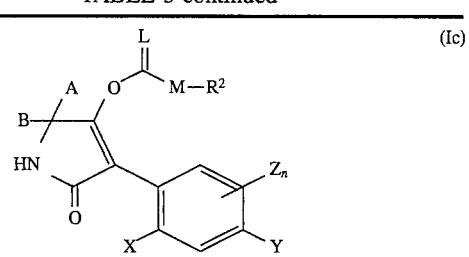

(Ic)

| A* | B | X | Y | $Z_n$ | L | M | $R^2$ |
|---|---|---|---|---|---|---|---|
| $C_5H_9$ | $CH_3$ | $CH_3$ | $CH_3$ | H | O | O | cyclohexyl |
| $C_5H_9$ | $CH_3$ | $CH_3$ | $CH_3$ | H | O | O | phenyl |
| $C_5H_9$ | $CH_3$ | $CH_3$ | $CH_3$ | H | O | O | benzyl |
| $C_5H_9$ | $CH_3$ | $CH_3$ | $CH_3$ | H | O | S | $CH_3$ |
| $C_5H_9$ | $CH_3$ | $CH_3$ | $CH_3$ | H | O | S | $C_2H_5-$ |
| $C_5H_9$ | $CH_3$ | $CH_3$ | $CH_3$ | H | O | S | $C_3H_7-$ |
| $C_5H_9$ | $CH_3$ | $CH_3$ | $CH_3$ | H | O | S | $i-C_3H_7-$ |
| $C_5H_9$ | $CH_3$ | $CH_3$ | $CH_3$ | H | O | S | $i-C_4H_9-$ |
| $C_5H_9$ | $CH_3$ | $CH_3$ | $CH_3$ | H | O | S | $s-C_4H_9-$ |
| $C_5H_9$ | $CH_3$ | $CH_3$ | $CH_3$ | H | O | S | $t-C_4H_9-$ |
| $C_5H_9$ | $CH_3$ | $CH_3$ | $CH_3$ | H | O | S | $t-C_4H_9-CH_2-$ |
| $C_5H_9$ | $CH_3$ | $CH_3$ | $CH_3$ | 6-$CH_3$ | O | O | $CH_3$ |
| $C_5H_9$ | $CH_3$ | $CH_3$ | $CH_3$ | 6-$CH_3$ | O | O | $C_2H_5-$ |
| $C_5H_9$ | $CH_3$ | $CH_3$ | $CH_3$ | 6-$CH_3$ | O | O | $C_3H_7-$ |
| $C_5H_9$ | $CH_3$ | $CH_3$ | $CH_3$ | 6-$CH_3$ | O | O | $i-C_3H_7-$ |
| $C_5H_9$ | $CH_3$ | $CH_3$ | $CH_3$ | 6-$CH_3$ | O | O | $i-C_4H_9-$ |
| $C_5H_9$ | $CH_3$ | $CH_3$ | $CH_3$ | 6-$CH_3$ | O | O | $s-C_4H_9-$ |
| $C_5H_9$ | $CH_3$ | $CH_3$ | $CH_3$ | 6-$CH_3$ | O | O | $t-C_4H_9-$ |
| $C_5H_9$ | $CH_3$ | $CH_3$ | $CH_3$ | 6-$CH_3$ | O | O | $t-C_4H_9-CH_2-$ |
| $C_5H_9$ | $CH_3$ | $CH_3$ | $CH_3$ | 6-$CH_3$ | O | O | cyclohexyl |
| $C_5H_9$ | $CH_3$ | $CH_3$ | $CH_3$ | 6-$CH_3$ | O | O | phenyl |
| $C_5H_9$ | $CH_3$ | $CH_3$ | $CH_3$ | 6-$CH_3$ | O | O | benzyl |
| $C_5H_9$ | $CH_3$ | $CH_3$ | $CH_3$ | 6-$CH_3$ | O | S | $CH_3$ |
| $C_5H_9$ | $CH_3$ | $CH_3$ | $CH_3$ | 6-$CH_3$ | O | S | $C_2H_5-$ |
| $C_5H_9$ | $CH_3$ | $CH_3$ | $CH_3$ | 6-$CH_3$ | O | S | $C_3H_7-$ |
| $C_5H_9$ | $CH_3$ | $CH_3$ | $CH_3$ | 6-$CH_3$ | O | S | $i-C_3H_7-$ |
| $C_5H_9$ | $CH_3$ | $CH_3$ | $CH_3$ | 6-$CH_3$ | O | S | $i-C_4H_9-$ |
| $C_5H_9$ | $CH_3$ | $CH_3$ | $CH_3$ | 6-$CH_3$ | O | S | $s-C_4H_9-$ |
| $C_5H_9$ | $CH_3$ | $CH_3$ | $CH_3$ | 6-$CH_3$ | O | S | $t-C_4H_9-$ |
| $C_5H_9$ | $CH_3$ | $CH_3$ | $CH_3$ | 6-$CH_3$ | O | S | $t-C_4H_9-CH_2-$ |
| $C_6H_{11}$ | $CH_3$ | Cl | Cl | H | O | O | $CH_3$ |
| $C_6H_{11}$ | $CH_3$ | Cl | Cl | H | O | O | $C_2H_5-$ |
| $C_6H_{11}$ | $CH_3$ | Cl | Cl | H | O | O | $C_3H_7-$ |
| $C_6H_{11}$ | $CH_3$ | Cl | Cl | H | O | O | $i-C_3H_7-$ |
| $C_6H_{11}$ | $CH_3$ | Cl | Cl | H | O | O | $i-C_4H_9-$ |
| $C_6H_{11}$ | $CH_3$ | Cl | Cl | H | O | O | $s-C_4H_9-$ |
| $C_6H_{11}$ | $CH_3$ | Cl | Cl | H | O | O | $t-C_4H_9-$ |
| $C_6H_{11}$ | $CH_3$ | Cl | Cl | H | O | O | $t-C_4H_9-CH_2-$ |

TABLE 3-continued

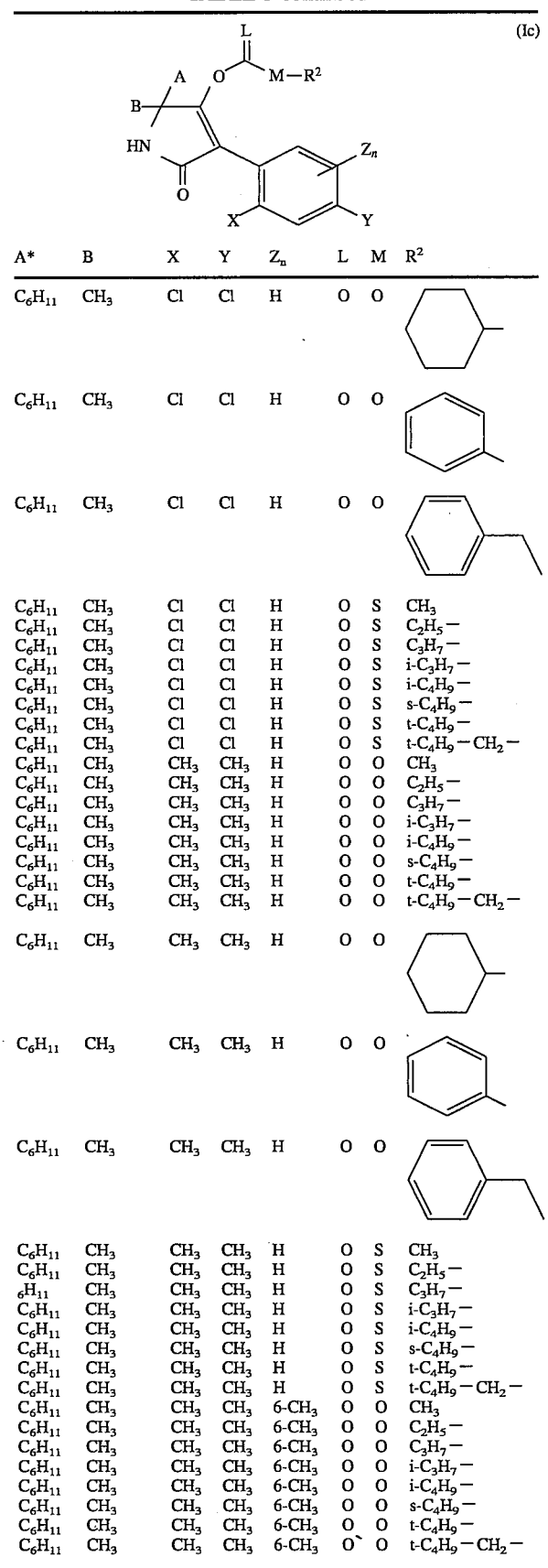

(Ic)

| A* | B | X | Y | $Z_n$ | L | M | $R^2$ |
|---|---|---|---|---|---|---|---|
| $C_6H_{11}$ | $CH_3$ | Cl | Cl | H | O | O | cyclohexyl |
| $C_6H_{11}$ | $CH_3$ | Cl | Cl | H | O | O | phenyl |
| $C_6H_{11}$ | $CH_3$ | Cl | Cl | H | O | O | benzyl (ethyl-phenyl) |
| $C_6H_{11}$ | $CH_3$ | Cl | Cl | H | O | S | $CH_3$ |
| $C_6H_{11}$ | $CH_3$ | Cl | Cl | H | O | S | $C_2H_5-$ |
| $C_6H_{11}$ | $CH_3$ | Cl | Cl | H | O | S | $C_3H_7-$ |
| $C_6H_{11}$ | $CH_3$ | Cl | Cl | H | O | S | $i$-$C_3H_7-$ |
| $C_6H_{11}$ | $CH_3$ | Cl | Cl | H | O | S | $i$-$C_4H_9-$ |
| $C_6H_{11}$ | $CH_3$ | Cl | Cl | H | O | S | $s$-$C_4H_9-$ |
| $C_6H_{11}$ | $CH_3$ | Cl | Cl | H | O | S | $t$-$C_4H_9-$ |
| $C_6H_{11}$ | $CH_3$ | Cl | Cl | H | O | S | $t$-$C_4H_9-CH_2-$ |
| $C_6H_{11}$ | $CH_3$ | $CH_3$ | $CH_3$ | H | O | O | $CH_3$ |
| $C_6H_{11}$ | $CH_3$ | $CH_3$ | $CH_3$ | H | O | O | $C_2H_5-$ |
| $C_6H_{11}$ | $CH_3$ | $CH_3$ | $CH_3$ | H | O | O | $C_3H_7-$ |
| $C_6H_{11}$ | $CH_3$ | $CH_3$ | $CH_3$ | H | O | O | $i$-$C_3H_7-$ |
| $C_6H_{11}$ | $CH_3$ | $CH_3$ | $CH_3$ | H | O | O | $i$-$C_4H_9-$ |
| $C_6H_{11}$ | $CH_3$ | $CH_3$ | $CH_3$ | H | O | O | $s$-$C_4H_9-$ |
| $C_6H_{11}$ | $CH_3$ | $CH_3$ | $CH_3$ | H | O | O | $t$-$C_4H_9-$ |
| $C_6H_{11}$ | $CH_3$ | $CH_3$ | $CH_3$ | H | O | O | $t$-$C_4H_9-CH_2-$ |
| $C_6H_{11}$ | $CH_3$ | $CH_3$ | $CH_3$ | H | O | O | cyclohexyl |
| $C_6H_{11}$ | $CH_3$ | $CH_3$ | $CH_3$ | H | O | O | phenyl |
| $C_6H_{11}$ | $CH_3$ | $CH_3$ | $CH_3$ | H | O | O | benzyl (ethyl-phenyl) |
| $C_6H_{11}$ | $CH_3$ | $CH_3$ | $CH_3$ | H | O | S | $CH_3$ |
| $C_6H_{11}$ | $CH_3$ | $CH_3$ | $CH_3$ | H | O | S | $C_2H_5-$ |
| $C_6H_{11}$ | $CH_3$ | $CH_3$ | $CH_3$ | H | O | S | $C_3H_7-$ |
| $C_6H_{11}$ | $CH_3$ | $CH_3$ | $CH_3$ | H | O | S | $i$-$C_3H_7-$ |
| $C_6H_{11}$ | $CH_3$ | $CH_3$ | $CH_3$ | H | O | S | $i$-$C_4H_9-$ |
| $C_6H_{11}$ | $CH_3$ | $CH_3$ | $CH_3$ | H | O | S | $s$-$C_4H_9-$ |
| $C_6H_{11}$ | $CH_3$ | $CH_3$ | $CH_3$ | H | O | S | $t$-$C_4H_9-$ |
| $C_6H_{11}$ | $CH_3$ | $CH_3$ | $CH_3$ | H | O | S | $t$-$C_4H_9-CH_2-$ |
| $C_6H_{11}$ | $CH_3$ | $CH_3$ | $CH_3$ | 6-$CH_3$ | O | O | $CH_3$ |
| $C_6H_{11}$ | $CH_3$ | $CH_3$ | $CH_3$ | 6-$CH_3$ | O | O | $C_2H_5-$ |
| $C_6H_{11}$ | $CH_3$ | $CH_3$ | $CH_3$ | 6-$CH_3$ | O | O | $C_3H_7-$ |
| $C_6H_{11}$ | $CH_3$ | $CH_3$ | $CH_3$ | 6-$CH_3$ | O | O | $i$-$C_3H_7-$ |
| $C_6H_{11}$ | $CH_3$ | $CH_3$ | $CH_3$ | 6-$CH_3$ | O | O | $i$-$C_4H_9-$ |
| $C_6H_{11}$ | $CH_3$ | $CH_3$ | $CH_3$ | 6-$CH_3$ | O | O | $s$-$C_4H_9-$ |
| $C_6H_{11}$ | $CH_3$ | $CH_3$ | $CH_3$ | 6-$CH_3$ | O | O | $t$-$C_4H_9-$ |
| $C_6H_{11}$ | $CH_3$ | $CH_3$ | $CH_3$ | 6-$CH_3$ | O | O | $t$-$C_4H_9-CH_2-$ |
| $C_6H_{11}$ | $CH_3$ | $CH_3$ | $CH_3$ | 6-$CH_3$ | O | O | cyclohexyl |
| $C_6H_{11}$ | $CH_3$ | $CH_3$ | $CH_3$ | 6-$CH_3$ | O | O | phenyl |
| $C_6H_{11}$ | $CH_3$ | $CH_3$ | $CH_3$ | 6-$CH_3$ | O | O | benzyl (ethyl-phenyl) |
| $C_6H_{11}$ | $CH_3$ | $CH_3$ | $CH_3$ | 6-$CH_3$ | O | S | $CH_3$ |
| $C_6H_{11}$ | $CH_3$ | $CH_3$ | $CH_3$ | 6-$CH_3$ | O | S | $C_2H_5-$ |
| $C_6H_{11}$ | $CH_3$ | $CH_3$ | $CH_3$ | 6-$CH_3$ | O | S | $C_3H_7-$ |
| $C_6H_{11}$ | $CH_3$ | $CH_3$ | $CH_3$ | 6-$CH_3$ | O | S | $i$-$C_3H_7-$ |
| $C_6H_{11}$ | $CH_3$ | $CH_3$ | $CH_3$ | 6-$CH_3$ | O | S | $i$-$C_4H_9-$ |
| $C_6H_{11}$ | $CH_3$ | $CH_3$ | $CH_3$ | 6-$CH_3$ | O | S | $s$-$C_4H_9-$ |
| $C_6H_{11}$ | $CH_3$ | $CH_3$ | $CH_3$ | 6-$CH_3$ | O | S | $t$-$C_4H_9-$ |
| $C_6H_{11}$ | $CH_3$ | $CH_3$ | $CH_3$ | 6-$CH_3$ | O | S | $t$-$C_4H_9-CH_2-$ |

A* =

$C_3H_5 =$ cyclopropyl, $C_5H_9 =$ cyclopentyl, $C_6H_{11} =$ cyclohexyl

The following compounds of the formula (Id) may be mentioned individually in addition to the compounds mentioned in the Preparation Examples:

TABLE 4

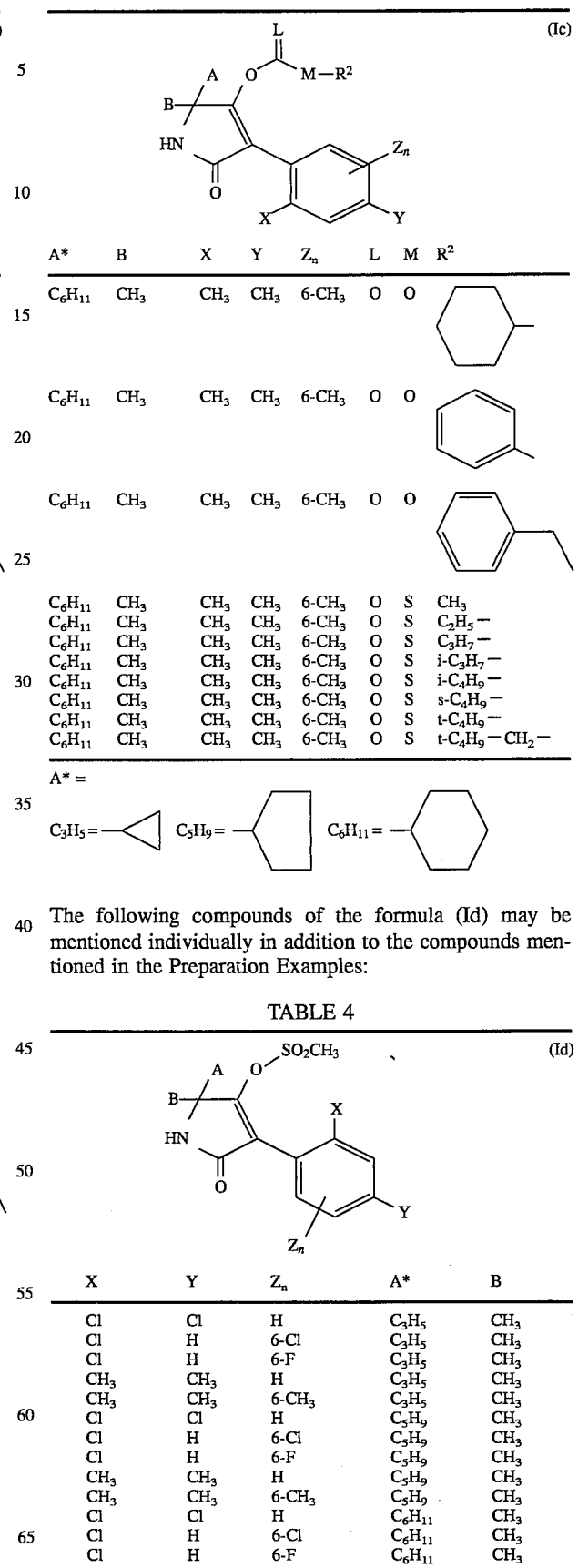

(Id)

| X | Y | $Z_n$ | A* | B |
|---|---|---|---|---|
| Cl | Cl | H | $C_3H_5$ | $CH_3$ |
| Cl | H | 6-Cl | $C_3H_5$ | $CH_3$ |
| Cl | H | 6-F | $C_3H_5$ | $CH_3$ |
| $CH_3$ | $CH_3$ | H | $C_3H_5$ | $CH_3$ |
| $CH_3$ | $CH_3$ | 6-$CH_3$ | $C_3H_5$ | $CH_3$ |
| Cl | Cl | H | $C_5H_9$ | $CH_3$ |
| Cl | H | 6-Cl | $C_5H_9$ | $CH_3$ |
| Cl | H | 6-F | $C_5H_9$ | $CH_3$ |
| $CH_3$ | $CH_3$ | H | $C_5H_9$ | $CH_3$ |
| $CH_3$ | $CH_3$ | 6-$CH_3$ | $C_5H_9$ | $CH_3$ |
| Cl | Cl | H | $C_6H_{11}$ | $CH_3$ |
| Cl | H | 6-Cl | $C_6H_{11}$ | $CH_3$ |
| Cl | H | 6-F | $C_6H_{11}$ | $CH_3$ |

TABLE 4-continued (Id)

[Structure: cyclic compound with A, B substituents, O-SO2CH3 group, HN, C=O, and phenyl ring with X, Y, Zn substituents]

| X | Y | Z_n | A* | B |
|---|---|---|---|---|
| CH_3 | CH_3 | H | C_6H_11 | CH_3 |
| CH_3 | CH_3 | 6-CH_3 | C_6H_11 | CH_3 |

A* =

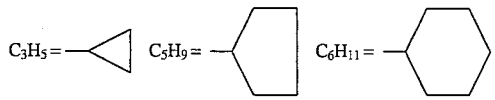

$C_3H_5 =$ cyclopropyl, $C_5H_9 =$ cyclopentyl, $C_6H_{11} =$ cyclohexyl

The following compounds of the formula (Ie) may be mentioned individually in addition to the compounds mentioned in the Preparation Examples:

TABLE 5

(Ie)

[Structure: cyclic compound with A, B substituents, O-P(=L)(R^4)(R^5) group, HN, C=O, and phenyl ring with X, Y, Zn substituents]

| A* | B | X | Y | Z_n | L | R^4 | R^5 |
|---|---|---|---|---|---|---|---|
| C_3H_5 | CH_3 | Cl | Cl | H | O | CH_3 | CH_3—O— |
| C_3H_5 | CH_3 | Cl | Cl | H | O | CH_3 | C_2H_5—O— |
| C_3H_5 | CH_3 | Cl | Cl | H | O | CH_3 | C_3H_7—O— |
| C_3H_5 | CH_3 | Cl | Cl | H | O | CH_3 | i-C_3H_7—O |
| C_3H_5 | CH_3 | Cl | Cl | H | O | CH_3 | i-C_4H_9—O |
| C_3H_5 | CH_3 | Cl | Cl | H | O | CH_3 | s-C_4H_9—O |
| C_3H_5 | CH_3 | Cl | Cl | H | O | CH_3 | t-C_4H_9—O |
| C_3H_5 | CH_3 | Cl | Cl | H | O | CH_3 | t-C_4H_9—CH_2—O |
| C_3H_5 | CH_3 | Cl | Cl | H | O | CH_3 | cyclohexyl-O— |
| C_3H_5 | CH_3 | Cl | Cl | H | O | CH_3 | phenyl-O— |
| C_3H_5 | CH_3 | Cl | Cl | H | O | CH_3 | benzyl-O— |
| C_3H_5 | CH_3 | Cl | Cl | H | O | CH_3 | CH_3—S— |
| C_3H_5 | CH_3 | Cl | Cl | H | O | CH_3 | C_2H_5—S— |
| C_3H_5 | CH_3 | Cl | Cl | H | O | CH_3 | C_3H_7—S— |
| C_3H_5 | CH_3 | Cl | Cl | H | O | CH_3 | i-C_3H_7—S— |
| C_3H_5 | CH_3 | Cl | Cl | H | O | CH_3 | i-C_4H_9—S— |
| C_3H_5 | CH_3 | Cl | Cl | H | O | CH_3 | s-C_4H_9—S— |
| C_3H_5 | CH_3 | Cl | Cl | H | O | CH_3 | t-C_4H_9—S— |
| C_3H_5 | CH_3 | Cl | Cl | H | O | CH_3 | t-C_4H_9—CH_2—S— |
| C_3H_5 | CH_3 | CH_3 | CH_3 | H | O | CH_3 | CH_3—O— |
| C_3H_5 | CH_3 | CH_3 | CH_3 | H | O | CH_3 | C_2H_5—O— |
| C_3H_5 | CH_3 | CH_3 | CH_3 | H | O | CH_3 | C_3H_7—O— |
| C_3H_5 | CH_3 | CH_3 | CH_3 | H | O | CH_3 | i-C_3H_7—O |

TABLE 5-continued

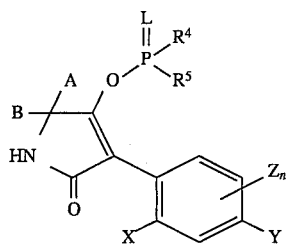

(Ie)

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | H | O | $CH_3$ | $i\text{-}C_4H_9\text{—}O$ |
| $C_3H_5$ | $CH_3$ | $CH_3$ | $CH_3$ | H | O | $CH_3$ | $s\text{-}C_4H_9\text{—}O$ |
| $C_3H_5$ | $CH_3$ | $CH_3$ | $CH_3$ | H | O | $CH_3$ | $t\text{-}C_4H_9\text{—}O$ |
| $C_3H_5$ | $CH_3$ | $CH_3$ | $CH_3$ | H | O | $CH_3$ | $t\text{-}C_4H_9\text{—}CH_2\text{—}O$ |
| $C_3H_5$ | $CH_3$ | $CH_3$ | $CH_3$ | H | O | $CH_3$ | cyclohexyl-O— |
| $C_3H_5$ | $CH_3$ | $CH_3$ | $CH_3$ | H | O | $CH_3$ | phenyl-O— |
| $C_3H_5$ | $CH_3$ | $CH_3$ | $CH_3$ | H | O | $CH_3$ | benzyl-O— |
| $C_3H_5$ | $CH_3$ | $CH_3$ | $CH_3$ | H | O | $CH_3$ | $CH_3\text{—}S\text{—}$ |
| $C_3H_5$ | $CH_3$ | $CH_3$ | $CH_3$ | H | O | $CH_3$ | $C_2H_5\text{—}S\text{—}$ |
| $C_3H_5$ | $CH_3$ | $CH_3$ | $CH_3$ | H | O | $CH_3$ | $C_3H_7\text{—}S\text{—}$ |
| $C_3H_5$ | $CH_3$ | $CH_3$ | $CH_3$ | H | O | $CH_3$ | $i\text{-}C_3H_7\text{—}S\text{—}$ |
| $C_3H_5$ | $CH_3$ | $CH_3$ | $CH_3$ | H | O | $CH_3$ | $i\text{-}C_4H_9\text{—}S\text{—}$ |
| $C_3H_5$ | $CH_3$ | $CH_3$ | $CH_3$ | H | O | $CH_3$ | $s\text{-}C_4H_9\text{—}S\text{—}$ |
| $C_3H_5$ | $CH_3$ | $CH_3$ | $CH_3$ | H | O | $CH_3$ | $t\text{-}C_4H_9\text{—}S\text{—}$ |
| $C_3H_5$ | $CH_3$ | $CH_3$ | $CH_3$ | H | O | $CH_3$ | $t\text{-}C_4H_9\text{—}CH_2\text{—}S\text{—}$ |
| $C_3H_5$ | $CH_3$ | $CH_3$ | $CH_3$ | 6-$CH_3$ | O | $CH_3$ | $CH_3\text{—}O\text{—}$ |
| $C_3H_5$ | $CH_3$ | $CH_3$ | $CH_3$ | 6-$CH_3$ | O | $CH_3$ | $C_2H_5\text{—}O\text{—}$ |
| $C_3H_5$ | $CH_3$ | $CH_3$ | $CH_3$ | 6-$CH_3$ | O | $CH_3$ | $C_3H_7\text{—}O\text{—}$ |
| $C_3H_5$ | $CH_3$ | $CH_3$ | $CH_3$ | 6-$CH_3$ | O | $CH_3$ | $i\text{-}C_3H_7\text{—}O$ |
| $C_3H_5$ | $CH_3$ | $CH_3$ | $CH_3$ | 6-$CH_3$ | O | $CH_3$ | $i\text{-}C_4H_9\text{—}O$ |
| $C_3H_5$ | $CH_3$ | $CH_3$ | $CH_3$ | 6-$CH_3$ | O | $CH_3$ | $s\text{-}C_4H_9\text{—}O$ |
| $C_3H_5$ | $CH_3$ | $CH_3$ | $CH_3$ | 6-$CH_3$ | O | $CH_3$ | $t\text{-}C_4H_9\text{—}O$ |
| $C_3H_5$ | $CH_3$ | $CH_3$ | $CH_3$ | 6-$CH_3$ | O | $CH_3$ | $t\text{-}C_4H_9\text{—}CH_2\text{—}O$ |
| $C_3H_5$ | $CH_3$ | $CH_3$ | $CH_3$ | 6-$CH_3$ | O | $CH_3$ | cyclohexyl-O— |
| $C_3H_5$ | $CH_3$ | $CH_3$ | $CH_3$ | 6-$CH_3$ | O | $CH_3$ | phenyl-O— |
| $C_3H_5$ | $CH_3$ | $CH_3$ | $CH_3$ | 6-$CH_3$ | O | $CH_3$ | benzyl-O— |
| $C_3H_5$ | $CH_3$ | $CH_3$ | $CH_3$ | 6-$CH_3$ | O | $CH_3$ | $CH_3\text{—}S\text{—}$ |
| $C_3H_5$ | $CH_3$ | $CH_3$ | $CH_3$ | 6-$CH_3$ | O | $CH_3$ | $C_2H_5\text{—}S\text{—}$ |
| $C_3H_5$ | $CH_3$ | $CH_3$ | $CH_3$ | 6-$CH_3$ | O | $CH_3$ | $C_3H_7\text{—}S\text{—}$ |
| $C_3H_5$ | $CH_3$ | $CH_3$ | $CH_3$ | 6-$CH_3$ | O | $CH_3$ | $i\text{-}C_3H_7\text{—}S\text{—}$ |
| $C_3H_5$ | $CH_3$ | $CH_3$ | $CH_3$ | 6-$CH_3$ | O | $CH_3$ | $i\text{-}C_4H_9\text{—}S\text{—}$ |
| $C_3H_5$ | $CH_3$ | $CH_3$ | $CH_3$ | 6-$CH_3$ | O | $CH_3$ | $s\text{-}C_4H_9\text{—}S\text{—}$ |
| $C_3H_5$ | $CH_3$ | $CH_3$ | $CH_3$ | 6-$CH_3$ | O | $CH_3$ | $t\text{-}C_4H_9\text{—}S\text{—}$ |
| $C_3H_5$ | $CH_3$ | $CH_3$ | $CH_3$ | 6-$CH_3$ | O | $CH_3$ | $t\text{-}C_4H_9\text{—}CH_2\text{—}S\text{—}$ |
| $C_6H_{11}$ | $CH_3$ | Cl | Cl | H | O | $CH_3$ | $CH_3\text{—}O\text{—}$ |
| $C_6H_{11}$ | $CH_3$ | Cl | Cl | H | O | $CH_3$ | $C_2H_5\text{—}O\text{—}$ |
| $C_6H_{11}$ | $CH_3$ | Cl | Cl | H | O | $CH_3$ | $C_3H_7\text{—}O\text{—}$ |

TABLE 5-continued (Ie)

$$\underset{\underset{O}{\overset{HN}{\mid}}}{\overset{B}{\mid}}\overset{A}{\underset{}{C}}=\overset{}{\underset{}{C}}\overset{O-P(=L)(R^4)(R^5)}{\underset{\text{aryl}(X,Y,Z_n)}{}}$$

| A* | B | X | Y | $Z_n$ | L | $R^4$ | $R^5$ |
|---|---|---|---|---|---|---|---|
| $C_6H_{11}$ | $CH_3$ | Cl | Cl | H | O | $CH_3$ | $i\text{-}C_3H_7\text{-}O$ |
| $C_6H_{11}$ | $CH_3$ | Cl | Cl | H | O | $CH_3$ | $i\text{-}C_4H_9\text{-}O$ |
| $C_6H_{11}$ | $CH_3$ | Cl | Cl | H | O | $CH_3$ | $s\text{-}C_4H_9\text{-}O$ |
| $C_6H_{11}$ | $CH_3$ | Cl | Cl | H | O | $CH_3$ | $t\text{-}C_4H_9\text{-}O$ |
| $C_6H_{11}$ | $CH_3$ | Cl | Cl | H | O | $CH_3$ | $t\text{-}C_4H_9\text{-}CH_2\text{-}O$ |
| $C_6H_{11}$ | $CH_3$ | Cl | Cl | H | O | $CH_3$ | cyclohexyl-O- |
| $C_6H_{11}$ | $CH_3$ | Cl | Cl | H | O | $CH_3$ | phenyl-O- |
| $C_6H_{11}$ | $CH_3$ | Cl | Cl | H | O | $CH_3$ | benzyl-O- |
| $C_6H_{11}$ | $CH_3$ | Cl | Cl | H | O | $CH_3$ | $CH_3\text{-}S\text{-}$ |
| $C_6H_{11}$ | $CH_3$ | Cl | Cl | H | O | $CH_3$ | $C_2H_5\text{-}S\text{-}$ |
| $C_6H_{11}$ | $CH_3$ | Cl | Cl | H | O | $CH_3$ | $C_3H_7\text{-}S\text{-}$ |
| $C_6H_{11}$ | $CH_3$ | Cl | Cl | H | O | $CH_3$ | $i\text{-}C_3H_7\text{-}S\text{-}$ |
| $C_6H_{11}$ | $CH_3$ | Cl | Cl | H | O | $CH_3$ | $i\text{-}C_4H_9\text{-}S\text{-}$ |
| $C_6H_{11}$ | $CH_3$ | Cl | Cl | H | O | $CH_3$ | $s\text{-}C_4H_9\text{-}S\text{-}$ |
| $C_6H_{11}$ | $CH_3$ | Cl | Cl | H | O | $CH_3$ | $t\text{-}C_4H_9\text{-}S\text{-}$ |
| $C_6H_{11}$ | $CH_3$ | Cl | Cl | H | O | $CH_3$ | $t\text{-}C_4H_9\text{-}CH_2\text{-}S\text{-}$ |
| $C_6H_{11}$ | $CH_3$ | $CH_3$ | $CH_3$ | H | O | $CH_3$ | $CH_3\text{-}O\text{-}$ |
| $C_6H_{11}$ | $CH_3$ | $CH_3$ | $CH_3$ | H | O | $CH_3$ | $C_2H_5\text{-}O\text{-}$ |
| $C_6H_{11}$ | $CH_3$ | $CH_3$ | $CH_3$ | H | O | $CH_3$ | $C_3H_7\text{-}O\text{-}$ |
| $C_6H_{11}$ | $CH_3$ | $CH_3$ | $CH_3$ | H | O | $CH_3$ | $i\text{-}C_3H_7\text{-}O$ |
| $C_6H_{11}$ | $CH_3$ | $CH_3$ | $CH_3$ | H | O | $CH_3$ | $i\text{-}C_4H_9\text{-}O$ |
| $C_6H_{11}$ | $CH_3$ | $CH_3$ | $CH_3$ | H | O | $CH_3$ | $s\text{-}C_4H_9\text{-}O$ |
| $C_6H_{11}$ | $CH_3$ | $CH_3$ | $CH_3$ | H | O | $CH_3$ | $t\text{-}C_4H_9\text{-}O$ |
| $C_6H_{11}$ | $CH_3$ | $CH_3$ | $CH_3$ | H | O | $CH_3$ | $t\text{-}C_4H_9\text{-}CH_2\text{-}O$ |
| $C_6H_{11}$ | $CH_3$ | $CH_3$ | $CH_3$ | H | O | $CH_3$ | cyclohexyl-O- |
| $C_6H_{11}$ | $CH_3$ | $CH_3$ | $CH_3$ | H | O | $CH_3$ | phenyl-O- |
| $C_6H_{11}$ | $CH_3$ | $CH_3$ | $CH_3$ | H | O | $CH_3$ | benzyl-O- |
| $C_6H_{11}$ | $CH_3$ | $CH_3$ | $CH_3$ | H | O | $CH_3$ | $CH_3\text{-}S\text{-}$ |
| $C_6H_{11}$ | $CH_3$ | $CH_3$ | $CH_3$ | H | O | $CH_3$ | $C_2H_5\text{-}S\text{-}$ |
| $C_6H_{11}$ | $CH_3$ | $CH_3$ | $CH_3$ | H | O | $CH_3$ | $C_3H_7\text{-}S\text{-}$ |
| $C_6H_{11}$ | $CH_3$ | $CH_3$ | $CH_3$ | H | O | $CH_3$ | $i\text{-}C_3H_7\text{-}S\text{-}$ |
| $C_6H_{11}$ | $CH_3$ | $CH_3$ | $CH_3$ | H | O | $CH_3$ | $i\text{-}C_4H_9\text{-}S\text{-}$ |
| $C_6H_{11}$ | $CH_3$ | $CH_3$ | $CH_3$ | H | O | $CH_3$ | $s\text{-}C_4H_9\text{-}S\text{-}$ |
| $C_6H_{11}$ | $CH_3$ | $CH_3$ | $CH_3$ | H | O | $CH_3$ | $t\text{-}C_4H_9\text{-}S\text{-}$ |
| $C_6H_{11}$ | $CH_3$ | $CH_3$ | $CH_3$ | H | O | $CH_3$ | $t\text{-}C_4H_9\text{-}CH_2\text{-}S\text{-}$ |
| $C_6H_{11}$ | $CH_3$ | $CH_3$ | $CH_3$ | $6\text{-}CH_3$ | O | $CH_3$ | $CH_3\text{-}O\text{-}$ |
| $C_6H_{11}$ | $CH_3$ | $CH_3$ | $CH_3$ | $6\text{-}CH_3$ | O | $CH_3$ | $C_2H_5\text{-}O\text{-}$ |

TABLE 5-continued (Ie)

$$\begin{array}{c} \text{structure (Ie) with substituents A, B, HN, O, X, Y, Z}_n\text{, L, P, R}^4\text{, R}^5 \end{array}$$

| A* | B | X | Y | $Z_n$ | L | $R^4$ | $R^5$ |
|---|---|---|---|---|---|---|---|
| $C_6H_{11}$ | $CH_3$ | $CH_3$ | $CH_3$ | 6-$CH_3$ | O | $CH_3$ | $C_3H_7$—O— |
| $C_6H_{11}$ | $CH_3$ | $CH_3$ | $CH_3$ | 6-$CH_3$ | O | $CH_3$ | i-$C_3H_7$—O |
| $C_6H_{11}$ | $CH_3$ | $CH_3$ | $CH_3$ | 6-$CH_3$ | O | $CH_3$ | i-$C_4H_9$—O |
| $C_6H_{11}$ | $CH_3$ | $CH_3$ | $CH_3$ | 6-$CH_3$ | O | $CH_3$ | s-$C_4H_9$—O |
| $C_6H_{11}$ | $CH_3$ | $CH_3$ | $CH_3$ | 6-$CH_3$ | O | $CH_3$ | t-$C_4H_9$—O |
| $C_6H_{11}$ | $CH_3$ | $CH_3$ | $CH_3$ | 6-$CH_3$ | O | $CH_3$ | t-$C_4H_9$—$CH_2$—O |
| $C_6H_{11}$ | $CH_3$ | $CH_3$ | $CH_3$ | 6-$CH_3$ | O | $CH_3$ | cyclohexyl-O— |
| $C_6H_{11}$ | $CH_3$ | $CH_3$ | $CH_3$ | 6-$CH_3$ | O | $CH_3$ | phenyl-O— |
| $C_6H_{11}$ | $CH_3$ | $CH_3$ | $CH_3$ | 6-$CH_3$ | O | $CH_3$ | benzyl-O— |
| $C_6H_{11}$ | $CH_3$ | $CH_3$ | $CH_3$ | 6-$CH_3$ | O | $CH_3$ | $CH_3$—S— |
| $C_6H_{11}$ | $CH_3$ | $CH_3$ | $CH_3$ | 6-$CH_3$ | O | $CH_3$ | $C_2H_5$—S— |
| $C_6H_{11}$ | $CH_3$ | $CH_3$ | $CH_3$ | 6-$CH_3$ | O | $CH_3$ | $C_3H_7$—S— |
| $C_6H_{11}$ | $CH_3$ | $CH_3$ | $CH_3$ | 6-$CH_3$ | O | $CH_3$ | i-$C_3H_7$—S— |
| $C_6H_{11}$ | $CH_3$ | $CH_3$ | $CH_3$ | 6-$CH_3$ | O | $CH_3$ | i-$C_4H_9$—S— |
| $C_6H_{11}$ | $CH_3$ | $CH_3$ | $CH_3$ | 6-$CH_3$ | O | $CH_3$ | s-$C_4H_9$—S— |
| $C_6H_{11}$ | $CH_3$ | $CH_3$ | $CH_3$ | 6-$CH_3$ | O | $CH_3$ | t-$C_4H_9$—S— |
| $C_6H_{11}$ | $CH_3$ | $CH_3$ | $CH_3$ | 6-$CH_3$ | O | $CH_3$ | t-$C_4H_9$—$CH_2$—S— |
| $C_3H_5$ | $CH_3$ | Cl | Cl | H | O | $C_2H_5$ | $CH_3$—O— |
| $C_3H_5$ | $CH_3$ | Cl | Cl | H | O | $C_2H_5$ | $C_2H_5$—O— |
| $C_3H_5$ | $CH_3$ | Cl | Cl | H | O | $C_2H_5$ | $C_3H_7$—O— |
| $C_3H_5$ | $CH_3$ | Cl | Cl | H | O | $C_2H_5$ | i-$C_3H_7$—O |
| $C_3H_5$ | $CH_3$ | Cl | Cl | H | O | $C_2H_5$ | i-$C_4H_9$—O |
| $C_3H_5$ | $CH_3$ | Cl | Cl | H | O | $C_2H_5$ | s-$C_4H_9$—O |
| $C_3H_5$ | $CH_3$ | Cl | Cl | H | O | $C_2H_5$ | t-$C_4H_9$—O |
| $C_3H_5$ | $CH_3$ | Cl | Cl | H | O | $C_2H_5$ | t-$C_4H_9$—$CH_2$—O |
| $C_3H_5$ | $CH_3$ | Cl | Cl | H | O | $C_2H_5$ | cyclohexyl-O— |
| $C_3H_5$ | $CH_3$ | Cl | Cl | H | O | $C_2H_5$ | phenyl-O— |
| $C_3H_5$ | $CH_3$ | Cl | Cl | H | O | $C_2H_5$ | benzyl-O— |
| $C_3H_5$ | $CH_3$ | Cl | Cl | H | O | $C_2H_5$ | $CH_3$—S— |
| $C_3H_5$ | $CH_3$ | Cl | Cl | H | O | $C_2H_5$ | $C_2H_5$—S— |
| $C_3H_5$ | $CH_3$ | Cl | Cl | H | O | $C_2H_5$ | $C_3H_7$—S— |
| $C_3H_5$ | $CH_3$ | Cl | Cl | H | O | $C_2H_5$ | i-$C_3H_7$—S— |
| $C_3H_5$ | $CH_3$ | Cl | Cl | H | O | $C_2H_5$ | i-$C_4H_9$—S— |
| $C_3H_5$ | $CH_3$ | Cl | Cl | H | O | $C_2H_5$ | s-$C_4H_9$—S— |
| $C_3H_5$ | $CH_3$ | Cl | Cl | H | O | $C_2H_5$ | t-$C_4H_9$—S— |
| $C_3H_5$ | $CH_3$ | Cl | Cl | H | O | $C_2H_5$ | it$C_4H_9$—$CH_2$—S— |
| $C_3H_5$ | $CH_3$ | $CH_3$ | $CH_3$ | H | O | $C_2H_5$ | $CH_3$—O— |

TABLE 5-continued

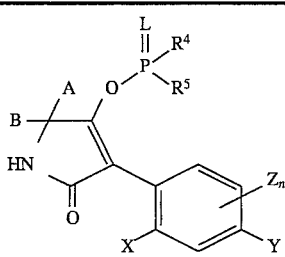

(Ie)

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | H | O | $C_2H_5$ | $C_2H_5-O-$ |
| $C_3H_5$ | $CH_3$ | $CH_3$ | $CH_3$ | H | O | $C_2H_5$ | $C_3H_7-O-$ |
| $C_3H_5$ | $CH_3$ | $CH_3$ | $CH_3$ | H | O | $C_2H_5$ | $i\text{-}C_3H_7-O$ |
| $C_3H_5$ | $CH_3$ | $CH_3$ | $CH_3$ | H | O | $C_2H_5$ | $i\text{-}C_4H_9-O$ |
| $C_3H_5$ | $CH_3$ | $CH_3$ | $CH_3$ | H | O | $C_2H_5$ | $s\text{-}C_4H_9-O$ |
| $C_3H_5$ | $CH_3$ | $CH_3$ | $CH_3$ | H | O | $C_2H_5$ | $t\text{-}C_4H_9-O$ |
| $C_3H_5$ | $CH_3$ | $CH_3$ | $CH_3$ | H | O | $C_2H_5$ | $t\text{-}C_4H_9-CH_2-O$ |
| $C_3H_5$ | $CH_3$ | $CH_3$ | $CH_3$ | H | O | $C_2H_5$ | 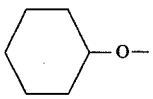 |
| $C_3H_5$ | $CH_3$ | $CH_3$ | $CH_3$ | H | O | $C_2H_5$ | 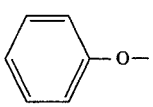 |
| $C_3H_5$ | $CH_3$ | $CH_3$ | $CH_3$ | H | O | $C_2H_5$ | 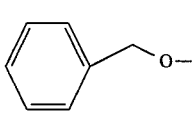 |
| $C_3H_5$ | $CH_3$ | $CH_3$ | $CH_3$ | H | O | $C_2H_5$ | $CH_3-S-$ |
| $C_3H_5$ | $CH_3$ | $CH_3$ | $CH_3$ | H | O | $C_2H_5$ | $C_2H_5-S-$ |
| $C_3H_5$ | $CH_3$ | $CH_3$ | $CH_3$ | H | O | $C_2H_5$ | $C_3H_7-S-$ |
| $C_3H_5$ | $CH_3$ | $CH_3$ | $CH_3$ | H | O | $C_2H_5$ | $i\text{-}C_3H_7-S-$ |
| $C_3H_5$ | $CH_3$ | $CH_3$ | $CH_3$ | H | O | $C_2H_5$ | $i\text{-}C_4H_9-S-$ |
| $C_3H_5$ | $CH_3$ | $CH_3$ | $CH_3$ | H | O | $C_2H_5$ | $s\text{-}C_4H_9-S-$ |
| $C_3H_5$ | $CH_3$ | $CH_3$ | $CH_3$ | H | O | $C_2H_5$ | $t\text{-}C_4H_9-S-$ |
| $C_3H_5$ | $CH_3$ | $CH_3$ | $CH_3$ | H | O | $C_2H_5$ | $t\text{-}C_4H_9-CH_2-S-$ |
| $C_3H_5$ | $CH_3$ | $CH_3$ | $CH_3$ | 6-$CH_3$ | O | $C_2H_5$ | $CH_3-O-$ |
| $C_3H_5$ | $CH_3$ | $CH_3$ | $CH_3$ | 6-$CH_3$ | O | $C_2H_5$ | $C_2H_5-O-$ |
| $C_3H_5$ | $CH_3$ | $CH_3$ | $CH_3$ | 6-$CH_3$ | O | $C_2H_5$ | $C_3H_7-O-$ |
| $C_3H_5$ | $CH_3$ | $CH_3$ | $CH_3$ | 6-$CH_3$ | O | $C_2H_5$ | $i\text{-}C_3H_7-O$ |
| $C_3H_5$ | $CH_3$ | $CH_3$ | $CH_3$ | 6-$CH_3$ | O | $C_2H_5$ | $i\text{-}C_4H_9-O$ |
| $C_3H_5$ | $CH_3$ | $CH_3$ | $CH_3$ | 6-$CH_3$ | O | $C_2H_5$ | $s\text{-}C_4H_9-O$ |
| $C_3H_5$ | $CH_3$ | $CH_3$ | $CH_3$ | 6-$CH_3$ | O | $C_2H_5$ | $t\text{-}C_4H_9-O$ |
| $C_3H_5$ | $CH_3$ | $CH_3$ | $CH_3$ | 6-$CH_3$ | O | $C_2H_5$ | $t\text{-}C_4H_9-CH_2-O$ |
| $C_3H_5$ | $CH_3$ | $CH_3$ | $CH_3$ | 6-$CH_3$ | O | $C_2H_5$ | 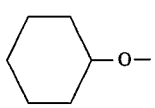 |
| $C_3H_5$ | $CH_3$ | $CH_3$ | $CH_3$ | 6-$CH_3$ | O | $C_2H_5$ | 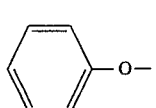 |
| $C_3H_5$ | $CH_3$ | $CH_3$ | $CH_3$ | 6-$CH_3$ | O | $C_2H_5$ | 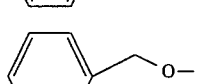 |
| $C_3H_5$ | $CH_3$ | $CH_3$ | $CH_3$ | 6-$CH_3$ | O | $C_2H_5$ | $CH_3-S-$ |
| $C_3H_5$ | $CH_3$ | $CH_3$ | $CH_3$ | 6-$CH_3$ | O | $C_2H_5$ | $C_2H_5-S-$ |
| $C_3H_5$ | $CH_3$ | $CH_3$ | $CH_3$ | 6-$CH_3$ | O | $C_2H_5$ | $C_3H_7-S-$ |
| $C_3H_5$ | $CH_3$ | $CH_3$ | $CH_3$ | 6-$CH_3$ | O | $C_2H_5$ | $i\text{-}C_3H_7-S-$ |
| $C_3H_5$ | $CH_3$ | $CH_3$ | $CH_3$ | 6-$CH_3$ | O | $C_2H_5$ | $i\text{-}C_4H_9-S-$ |
| $C_3H_5$ | $CH_3$ | $CH_3$ | $CH_3$ | 6-$CH_3$ | O | $C_2H_5$ | $s\text{-}C_4H_9-S-$ |
| $C_3H_5$ | $CH_3$ | $CH_3$ | $CH_3$ | 6-$CH_3$ | O | $C_2H_5$ | $t\text{-}C_4H_9-S-$ |
| $C_3H_5$ | $CH_3$ | $CH_3$ | $CH_3$ | 6-$CH_3$ | O | $C_2H_5$ | $t\text{-}C_4H_9-CH_2-S-$ |

TABLE 5-continued (Ie)
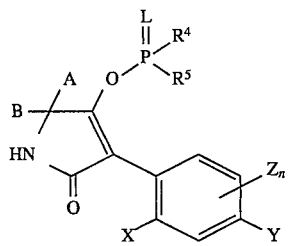

| A* | B | X | Y | $Z_n$ | L | $R^4$ | $R^5$ |
|---|---|---|---|---|---|---|---|
| $C_6H_{11}$ | $CH_3$ | Cl | Cl | H | O | $C_2H_5$ | $CH_3-O-$ |
| $C_6H_{11}$ | $CH_3$ | Cl | Cl | H | O | $C_2H_5$ | $C_2H_5-O-$ |
| $C_6H_{11}$ | $CH_3$ | Cl | Cl | H | O | $C_2H_5$ | $C_3H_7-O-$ |
| $C_6H_{11}$ | $CH_3$ | Cl | Cl | H | O | $C_2H_5$ | $i\text{-}C_3H_7-O$ |
| $C_6H_{11}$ | $CH_3$ | Cl | Cl | H | O | $C_2H_5$ | $i\text{-}C_4H_9-O$ |
| $C_6H_{11}$ | $CH_3$ | Cl | Cl | H | O | $C_2H_5$ | $s\text{-}C_4H_9-O$ |
| $C_6H_{11}$ | $CH_3$ | Cl | Cl | H | O | $C_2H_5$ | $t\text{-}C_4H_9-O$ |
| $C_6H_{11}$ | $CH_3$ | Cl | Cl | H | O | $C_2H_5$ | $t\text{-}C_4H_9-CH_2-O$ |
| $C_6H_{11}$ | $CH_3$ | Cl | Cl | H | O | $C_2H_5$ | 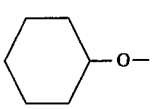 |
| $C_6H_{11}$ | $CH_3$ | Cl | Cl | H | O | $C_2H_5$ | 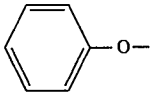 |
| $C_6H_{11}$ | $CH_3$ | Cl | Cl | H | O | $C_2H_5$ | 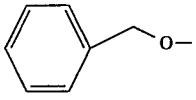 |
| $C_6H_{11}$ | $CH_3$ | Cl | Cl | H | O | $C_2H_5$ | $CH_3-S-$ |
| $C_6H_{11}$ | $CH_3$ | Cl | Cl | H | O | $C_2H_5$ | $C_2H_5-S-$ |
| $C_6H_{11}$ | $CH_3$ | Cl | Cl | H | O | $C_2H_5$ | $C_3H_7-S-$ |
| $C_6H_{11}$ | $CH_3$ | Cl | Cl | H | O | $C_2H_5$ | $i\text{-}C_3H_7-S-$ |
| $C_6H_{11}$ | $CH_3$ | Cl | Cl | H | O | $C_2H_5$ | $i\text{-}C_4H_9-S-$ |
| $C_6H_{11}$ | $CH_3$ | Cl | Cl | H | O | $C_2H_5$ | $s\text{-}C_4H_9-S-$ |
| $C_6H_{11}$ | $CH_3$ | Cl | Cl | H | O | $C_2H_5$ | $t\text{-}C_4H_9-S-$ |
| $C_6H_{11}$ | $CH_3$ | Cl | Cl | H | O | $C_2H_5$ | $t\text{-}C_4H_9-CH_2-S-$ |
| $C_6H_{11}$ | $CH_3$ | $CH_3$ | $CH_3$ | H | O | $C_2H_5$ | $CH_3-O-$ |
| $C_6H_{11}$ | $CH_3$ | $CH_3$ | $CH_3$ | H | O | $C_2H_5$ | $C_2H_5-O-$ |
| $C_6H_{11}$ | $CH_3$ | $CH_3$ | $CH_3$ | H | O | $C_2H_5$ | $C_3H_7-O-$ |
| $C_6H_{11}$ | $CH_3$ | $CH_3$ | $CH_3$ | H | O | $C_2H_5$ | $i\text{-}C_3H_7-O$ |
| $C_6H_{11}$ | $CH_3$ | $CH_3$ | $CH_3$ | H | O | $C_2H_5$ | $i\text{-}C_4H_9-O$ |
| $C_6H_{11}$ | $CH_3$ | $CH_3$ | $CH_3$ | H | O | $C_2H_5$ | $s\text{-}C_4H_9-O$ |
| $C_6H_{11}$ | $CH_3$ | $CH_3$ | $CH_3$ | H | O | $C_2H_5$ | $t\text{-}C_4H_9-O$ |
| $C_6H_{11}$ | $CH_3$ | $CH_3$ | $CH_3$ | H | O | $C_2H_5$ | $t\text{-}C_4H_9-CH_2-O$ |
| $C_6H_{11}$ | $CH_3$ | $CH_3$ | $CH_3$ | H | O | $C_2H_5$ | 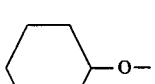 |
| $C_6H_{11}$ | $CH_3$ | $CH_3$ | $CH_3$ | H | O | $C_2H_5$ | 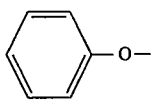 |
| $C_6H_{11}$ | $CH_3$ | $CH_3$ | $CH_3$ | H | O | $C_2H_5$ | 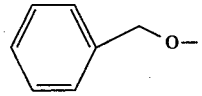 |
| $C_6H_{11}$ | $CH_3$ | $CH_3$ | $CH_3$ | H | O | $C_2H_5$ | $CH_3-S-$ |
| $C_6H_{11}$ | $CH_3$ | $CH_3$ | $CH_3$ | H | O | $C_2H_5$ | $C_2H_5-S-$ |
| $C_6H_{11}$ | $CH_3$ | $CH_3$ | $CH_3$ | H | O | $C_2H_5$ | $C_3H_7-S-$ |
| $C_6H_{11}$ | $CH_3$ | $CH_3$ | $CH_3$ | H | O | $C_2H_5$ | $i\text{-}C_3H_7-S-$ |
| $C_6H_{11}$ | $CH_3$ | $CH_3$ | $CH_3$ | H | O | $C_2H_5$ | $i\text{-}C_4H_9-S-$ |
| $C_6H_{11}$ | $CH_3$ | $CH_3$ | $CH_3$ | H | O | $C_2H_5$ | $s\text{-}C_4H_9-S-$ |
| $C_6H_{11}$ | $CH_3$ | $CH_3$ | $CH_3$ | H | O | $C_2H_5$ | $t\text{-}C_4H_9-S-$ |

TABLE 5-continued

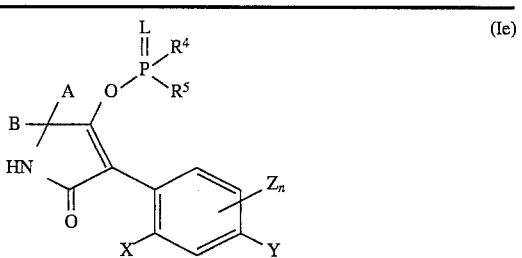

(Ie)

| A* | B | X | Y | $Z_n$ | L | $R^4$ | $R^5$ |
|---|---|---|---|---|---|---|---|
| $C_6H_{11}$ | $CH_3$ | $CH_3$ | $CH_3$ | H | O | $C_2H_5$ | $t\text{-}C_4H_9\text{—}CH_2\text{—}S\text{—}$ |
| $C_6H_{11}$ | $CH_3$ | $CH_3$ | $CH_3$ | 6-$CH_3$ | O | $C_2H_5$ | $CH_3\text{—}O\text{—}$ |
| $C_6H_{11}$ | $CH_3$ | $CH_3$ | $CH_3$ | 6-$CH_3$ | O | $C_2H_5$ | $C_2H_5\text{—}O\text{—}$ |
| $C_6H_{11}$ | $CH_3$ | $CH_3$ | $CH_3$ | 6-$CH_3$ | O | $C_2H_5$ | $C_3H_7\text{—}O\text{—}$ |
| $C_6H_{11}$ | $CH_3$ | $CH_3$ | $CH_3$ | 6-$CH_3$ | O | $C_2H_5$ | $i\text{-}C_3H_7\text{—}O$ |
| $C_6H_{11}$ | $CH_3$ | $CH_3$ | $CH_3$ | 6-$CH_3$ | O | $C_2H_5$ | $i\text{-}C_4H_9\text{—}O$ |
| $C_6H_{11}$ | $CH_3$ | $CH_3$ | $CH_3$ | 6-$CH_3$ | O | $C_2H_5$ | $s\text{-}C_4H_9\text{—}O$ |
| $C_6H_{11}$ | $CH_3$ | $CH_3$ | $CH_3$ | 6-$CH_3$ | O | $C_2H_5$ | $t\text{-}C_4H_9\text{—}O$ |
| $C_6H_{11}$ | $CH_3$ | $CH_3$ | $CH_3$ | 6-$CH_3$ | O | $C_2H_5$ | $t\text{-}C_4H_9\text{—}CH_2\text{—}O$ |
| $C_6H_{11}$ | $CH_3$ | $CH_3$ | $CH_3$ | 6-$CH_3$ | O | $C_2H_5$ | 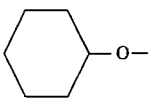 |
| $C_6H_{11}$ | $CH_3$ | $CH_3$ | $CH_3$ | 6-$CH_3$ | O | $C_2H_5$ | 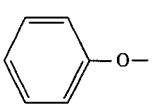 |
| $C_6H_{11}$ | $CH_3$ | $CH_3$ | $CH_3$ | 6-$CH_3$ | O | $C_2H_5$ | 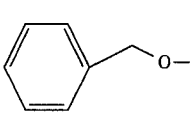 |
| $C_6H_{11}$ | $CH_3$ | $CH_3$ | $CH_3$ | 6-$CH_3$ | O | $C_2H_5$ | $CH_3\text{—}S\text{—}$ |
| $C_6H_{11}$ | $CH_3$ | $CH_3$ | $CH_3$ | 6-$CH_3$ | O | $C_2H_5$ | $C_2H_5\text{—}S\text{—}$ |
| $C_6H_{11}$ | $CH_3$ | $CH_3$ | $CH_3$ | 6-$CH_3$ | O | $C_2H_5$ | $C_3H_7\text{—}S\text{—}$ |
| $C_6H_{11}$ | $CH_3$ | $CH_3$ | $CH_3$ | 6-$CH_3$ | O | $C_2H_5$ | $i\text{-}C_3H_7\text{—}S\text{—}$ |
| $C_6H_{11}$ | $CH_3$ | $CH_3$ | $CH_3$ | 6-$CH_3$ | O | $C_2H_5$ | $i\text{-}C_4H_9\text{—}S\text{—}$ |
| $C_6H_{11}$ | $CH_3$ | $CH_3$ | $CH_3$ | 6-$CH_3$ | O | $C_2H_5$ | $s\text{-}C_4H_9\text{—}S\text{—}$ |
| $C_6H_{11}$ | $CH_3$ | $CH_3$ | $CH_3$ | 6-$CH_3$ | O | $C_2H_5$ | $t\text{-}C_4H_9\text{—}S\text{—}$ |
| $C_6H_{11}$ | $CH_3$ | $CH_3$ | $CH_3$ | 6-$CH_3$ | O | $C_2H_5$ | $t\text{-}C_4H_9\text{—}CH_2\text{—}S\text{—}$ |
| $C_3H_5$ | $CH_3$ | Cl | Cl | H | O | $O\text{—}CH_3$ | $CH_3\text{—}O\text{—}$ |
| $C_3H_5$ | $CH_3$ | Cl | Cl | H | O | $O\text{—}CH_3$ | $C_2H_5\text{—}O\text{—}$ |
| $C_3H_5$ | $CH_3$ | Cl | Cl | H | O | $O\text{—}CH_3$ | $C_3H_7\text{—}O\text{—}$ |
| $C_3H_5$ | $CH_3$ | Cl | Cl | H | O | $O\text{—}CH_3$ | $i\text{-}C_3H_7\text{—}O$ |
| $C_3H_5$ | $CH_3$ | Cl | Cl | H | O | $O\text{—}CH_3$ | $i\text{-}C_4H_9\text{—}O$ |
| $C_3H_5$ | $CH_3$ | Cl | Cl | H | O | $O\text{—}CH_3$ | $s\text{-}C_4H_9\text{—}O$ |
| $C_3H_5$ | $CH_3$ | Cl | Cl | H | O | $O\text{—}CH_3$ | $t\text{-}C_4H_9\text{—}O$ |
| $C_3H_5$ | $CH_3$ | Cl | Cl | H | O | $O\text{—}CH_3$ | $t\text{-}C_4H_9\text{—}CH_2\text{—}O$ |
| $C_3H_5$ | $CH_3$ | Cl | Cl | H | O | $O\text{—}CH_3$ | 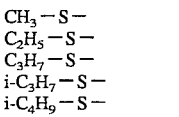 |
| $C_3H_5$ | $CH_3$ | Cl | Cl | H | O | $O\text{—}CH_3$ | 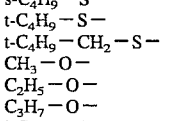 |
| $C_3H_5$ | $CH_3$ | Cl | Cl | H | O | $O\text{—}CH_3$ | 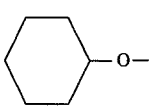 |
| $C_3H_5$ | $CH_3$ | Cl | Cl | H | O | $O\text{—}CH_3$ | $CH_3\text{—}S\text{—}$ |
| $C_3H_5$ | $CH_3$ | Cl | Cl | H | O | $O\text{—}CH_3$ | $C_2H_5\text{—}S\text{—}$ |
| $C_3H_5$ | $CH_3$ | Cl | Cl | H | O | $O\text{—}CH_3$ | $C_3H_7\text{—}S\text{—}$ |
| $C_3H_5$ | $CH_3$ | Cl | Cl | H | O | $O\text{—}CH_3$ | $i\text{-}C_3H_7\text{—}S\text{—}$ |
| $C_3H_5$ | $CH_3$ | Cl | Cl | H | O | $O\text{—}CH_3$ | $i\text{-}C_4H_9\text{—}S\text{—}$ |
| $C_3H_5$ | $CH_3$ | Cl | Cl | H | O | $O\text{—}CH_3$ | $s\text{-}C_4H_9\text{—}S\text{—}$ |

TABLE 5-continued (Ie)

$$\begin{array}{c} \text{structure with substituents A, B, HN, O, X, Y, } Z_n, \text{ and } -O-P(=L)(R^4)(R^5) \end{array}$$

| A* | B | X | Y | $Z_n$ | L | $R^4$ | $R^5$ |
|---|---|---|---|---|---|---|---|
| $C_3H_5$ | $CH_3$ | Cl | Cl | H | O | $O-CH_3$ | $t-C_4H_9-S-$ |
| $C_3H_5$ | $CH_3$ | Cl | Cl | H | O | $O-CH_3$ | $t-C_4H_9-CH_2-S-$ |
| $C_3H_5$ | $CH_3$ | $CH_3$ | $CH_3$ | H | O | $O-CH_3$ | $CH_3-O-$ |
| $C_3H_5$ | $CH_3$ | $CH_3$ | $CH_3$ | H | O | $O-CH_3$ | $C_2H_5-O-$ |
| $C_3H_5$ | $CH_3$ | $CH_3$ | $CH_3$ | H | O | $O-CH_3$ | $C_3H_7-O-$ |
| $C_3H_5$ | $CH_3$ | $CH_3$ | $CH_3$ | H | O | $O-CH_3$ | $i-C_3H_7-O$ |
| $C_3H_5$ | $CH_3$ | $CH_3$ | $CH_3$ | H | O | $O-CH_3$ | $i-C_4H_9-O$ |
| $C_3H_5$ | $CH_3$ | $CH_3$ | $CH_3$ | H | O | $O-CH_3$ | $s-C_4H_9-O$ |
| $C_3H_5$ | $CH_3$ | $CH_3$ | $CH_3$ | H | O | $O-CH_3$ | $t-C_4H_9-O$ |
| $C_3H_5$ | $CH_3$ | $CH_3$ | $CH_3$ | H | O | $O-CH_3$ | $t-C_4H_9-CH_2-O$ |
| $C_3H_5$ | $CH_3$ | $CH_3$ | $CH_3$ | H | O | $O-CH_3$ | cyclohexyl-O- |
| $C_3H_5$ | $CH_3$ | $CH_3$ | $CH_3$ | H | O | $O-CH_3$ | phenyl-O- |
| $C_3H_5$ | $CH_3$ | $CH_3$ | $CH_3$ | H | O | $O-CH_3$ | benzyl-O- |
| $C_3H_5$ | $CH_3$ | $CH_3$ | $CH_3$ | H | O | $O-CH_3$ | $CH_3-S-$ |
| $C_3H_5$ | $CH_3$ | $CH_3$ | $CH_3$ | H | O | $O-CH_3$ | $C_2H_5-S-$ |
| $C_3H_5$ | $CH_3$ | $CH_3$ | $CH_3$ | H | O | $O-CH_3$ | $C_3H_7-S-$ |
| $C_3H_5$ | $CH_3$ | $CH_3$ | $CH_3$ | H | O | $O-CH_3$ | $i-C_3H_7-S-$ |
| $C_3H_5$ | $CH_3$ | $CH_3$ | $CH_3$ | H | O | $O-CH_3$ | $i-C_4H_9-S-$ |
| $C_3H_5$ | $CH_3$ | $CH_3$ | $CH_3$ | H | O | $O-CH_3$ | $s-C_4H_9-S-$ |
| $C_3H_5$ | $CH_3$ | $CH_3$ | $CH_3$ | H | O | $O-CH_3$ | $t-C_4H_9-S-$ |
| $C_3H_5$ | $CH_3$ | $CH_3$ | $CH_3$ | H | O | $O-CH_3$ | $t-C_4H_9-CH_2-S-$ |
| $C_3H_5$ | $CH_3$ | $CH_3$ | $CH_3$ | $6-CH_3$ | O | $O-CH_3$ | $CH_3-O-$ |
| $C_3H_5$ | $CH_3$ | $CH_3$ | $CH_3$ | $6-CH_3$ | O | $O-CH_3$ | $C_2H_5-O-$ |
| $C_3H_5$ | $CH_3$ | $CH_3$ | $CH_3$ | $6-CH_3$ | O | $O-CH_3$ | $C_3H_7-O-$ |
| $C_3H_5$ | $CH_3$ | $CH_3$ | $CH_3$ | $6-CH_3$ | O | $O-CH_3$ | $i-C_3H_7-O$ |
| $C_3H_5$ | $CH_3$ | $CH_3$ | $CH_3$ | $6-CH_3$ | O | $O-CH_3$ | $i-C_4H_9-O$ |
| $C_3H_5$ | $CH_3$ | $CH_3$ | $CH_3$ | $6-CH_3$ | O | $O-CH_3$ | $s-C_4H_9-O$ |
| $C_3H_5$ | $CH_3$ | $CH_3$ | $CH_3$ | $6-CH_3$ | O | $O-CH_3$ | $t-C_4H_9-O$ |
| $C_3H_5$ | $CH_3$ | $CH_3$ | $CH_3$ | $6-CH_3$ | O | $O-CH_3$ | $t-C_4H_9-CH_2-O$ |
| $C_3H_5$ | $CH_3$ | $CH_3$ | $CH_3$ | $6-CH_3$ | O | $O-CH_3$ | cyclohexyl-O- |
| $C_3H_5$ | $CH_3$ | $CH_3$ | $CH_3$ | $6-CH_3$ | O | $O-CH_3$ | phenyl-O- |
| $C_3H_5$ | $CH_3$ | $CH_3$ | $CH_3$ | $6-CH_3$ | O | $O-CH_3$ | benzyl-O- |
| $C_3H_5$ | $CH_3$ | $CH_3$ | $CH_3$ | $6-CH_3$ | O | $O-CH_3$ | $CH_3-S-$ |
| $C_3H_5$ | $CH_3$ | $CH_3$ | $CH_3$ | $6-CH_3$ | O | $O-CH_3$ | $C_2H_5-S-$ |
| $C_3H_5$ | $CH_3$ | $CH_3$ | $CH_3$ | $6-CH_3$ | O | $O-CH_3$ | $C_3H_7-S-$ |
| $C_3H_5$ | $CH_3$ | $CH_3$ | $CH_3$ | $6-CH_3$ | O | $O-CH_3$ | $i-C_3H_7-S-$ |
| $C_3H_5$ | $CH_3$ | $CH_3$ | $CH_3$ | $6-CH_3$ | O | $O-CH_3$ | $i-C_4H_9-S-$ |

TABLE 5-continued

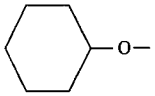
(Ie)

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | 6-$CH_3$ | O | O—$CH_3$ | s-$C_4H_9$—S— |
| $C_3H_5$ | $CH_3$ | $CH_3$ | $CH_3$ | 6-$CH_3$ | O | O—$CH_3$ | t-$C_4H_9$—S— |
| $C_3H_5$ | $CH_3$ | $CH_3$ | $CH_3$ | 6-$CH_3$ | O | O—$CH_3$ | t-$C_4H_9$—$CH_2$—S— |
| $C_6H_{11}$ | $CH_3$ | Cl | Cl | H | O | O—$CH_3$ | $CH_3$—O— |
| $C_6H_{11}$ | $CH_3$ | Cl | Cl | H | O | O—$CH_3$ | $C_2H_5$—O— |
| $C_6H_{11}$ | $CH_3$ | Cl | Cl | H | O | O—$CH_3$ | $C_3H_7$—O— |
| $C_6H_{11}$ | $CH_3$ | Cl | Cl | H | O | O—$CH_3$ | i-$C_3H_7$—O |
| $C_6H_{11}$ | $CH_3$ | Cl | Cl | H | O | O—$CH_3$ | i-$C_4H_9$—O |
| $C_6H_{11}$ | $CH_3$ | Cl | Cl | H | O | O—$CH_3$ | s-$C_4H_9$—O |
| $C_6H_{11}$ | $CH_3$ | Cl | Cl | H | O | O—$CH_3$ | t-$C_4H_9$—O |
| $C_6H_{11}$ | $CH_3$ | Cl | Cl | H | O | O—$CH_3$ | t-$C_4H_9$—$CH_2$—O |
| $C_6H_{11}$ | $CH_3$ | Cl | Cl | H | O | O—$CH_3$ | 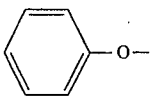 |
| $C_6H_{11}$ | $CH_3$ | Cl | Cl | H | O | O—$CH_3$ | 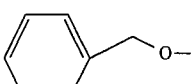 |
| $C_6H_{11}$ | $CH_3$ | Cl | Cl | H | O | O—$CH_3$ | 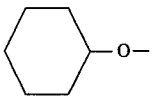 |
| $C_6H_{11}$ | $CH_3$ | Cl | Cl | H | O | O—$CH_3$ | $CH_3$—S— |
| $C_6H_{11}$ | $CH_3$ | Cl | Cl | H | O | O—$CH_3$ | $C_2H_5$—S— |
| $C_6H_{11}$ | $CH_3$ | Cl | Cl | H | O | O—$CH_3$ | $C_3H_7$—S— |
| $C_6H_{11}$ | $CH_3$ | Cl | Cl | H | O | O—$CH_3$ | i-$C_3H_7$—S— |
| $C_6H_{11}$ | $CH_3$ | Cl | Cl | H | O | O—$CH_3$ | i-$C_4H_9$—S— |
| $C_6H_{11}$ | $CH_3$ | Cl | Cl | H | O | O—$CH_3$ | s-$C_4H_9$—S— |
| $C_6H_{11}$ | $CH_3$ | Cl | Cl | H | O | O—$CH_3$ | t-$C_4H_9$—S— |
| $C_6H_{11}$ | $CH_3$ | Cl | Cl | H | O | O—$CH_3$ | t-$C_4H_9$—$CH_2$—S— |
| $C_6H_{11}$ | $CH_3$ | $CH_3$ | $CH_3$ | H | O | O—$CH_3$ | $CH_3$—O— |
| $C_6H_{11}$ | $CH_3$ | $CH_3$ | $CH_3$ | H | O | O—$CH_3$ | $C_2H_5$—O— |
| $C_6H_{11}$ | $CH_3$ | $CH_3$ | $CH_3$ | H | O | O—$CH_3$ | $C_3H_7$—O— |
| $C_6H_{11}$ | $CH_3$ | $CH_3$ | $CH_3$ | H | O | O—$CH_3$ | i-$C_3H_7$—O |
| $C_6H_{11}$ | $CH_3$ | $CH_3$ | $CH_3$ | H | O | O—$CH_3$ | i-$C_4H_9$—O |
| $C_6H_{11}$ | $CH_3$ | $CH_3$ | $CH_3$ | H | O | O—$CH_3$ | s-$C_4H_9$—O |
| $C_6H_{11}$ | $CH_3$ | $CH_3$ | $CH_3$ | H | O | O—$CH_3$ | t-$C_4H_9$—O |
| $C_6H_{11}$ | $CH_3$ | $CH_3$ | $CH_3$ | H | O | O—$CH_3$ | t-$C_4H_9$—$CH_2$—O |
| $C_6H_{11}$ | $CH_3$ | $CH_3$ | $CH_3$ | H | O | O—$CH_3$ | 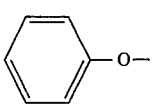 |
| $C_6H_{11}$ | $CH_3$ | $CH_3$ | $CH_3$ | H | O | O—$CH_3$ | 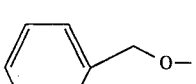 |
| $C_6H_{11}$ | $CH_3$ | $CH_3$ | $CH_3$ | H | O | O—$CH_3$ |  |
| $C_6H_{11}$ | $CH_3$ | $CH_3$ | $CH_3$ | H | O | O—$CH_3$ | $CH_3$—S— |
| $C_6H_{11}$ | $CH_3$ | $CH_3$ | $CH_3$ | H | O | O—$CH_3$ | $C_2H_5$—S— |
| $C_6H_{11}$ | $CH_3$ | $CH_3$ | $CH_3$ | H | O | O—$CH_3$ | $C_3H_7$—S— |
| $C_6H_{11}$ | $CH_3$ | $CH_3$ | $CH_3$ | H | O | O—$CH_3$ | i-$C_3H_7$—S— |

TABLE 5-continued (Ie)

[Structure: phosphorus-containing compound with substituents A, B, L, R⁴, R⁵, X, Y, Zₙ, HN, and carbonyl group]

| A* | B | X | Y | Zₙ | L | R⁴ | R⁵ |
|---|---|---|---|---|---|---|---|
| $C_6H_{11}$ | $CH_3$ | $CH_3$ | $CH_3$ | H | O | O—$CH_3$ | i-$C_4H_9$—S— |
| $C_6H_{11}$ | $CH_3$ | $CH_3$ | $CH_3$ | H | O | O—$CH_3$ | s-$C_4H_9$—S— |
| $C_6H_{11}$ | $CH_3$ | $CH_3$ | $CH_3$ | H | O | O—$CH_3$ | t-$C_4H_9$—S— |
| $C_6H_{11}$ | $CH_3$ | $CH_3$ | $CH_3$ | H | O | O—$CH_3$ | t-$C_4H_9$—$CH_2$—S— |
| $C_6H_{11}$ | $CH_3$ | $CH_3$ | $CH_3$ | 6-$CH_3$ | O | O—$CH_3$ | $CH_3$—O— |
| $C_6H_{11}$ | $CH_3$ | $CH_3$ | $CH_3$ | 6-$CH_3$ | O | O—$CH_3$ | $C_2H_5$—O— |
| $C_6H_{11}$ | $CH_3$ | $CH_3$ | $CH_3$ | 6-$CH_3$ | O | O—$CH_3$ | $C_3H_7$—O— |
| $C_6H_{11}$ | $CH_3$ | $CH_3$ | $CH_3$ | 6-$CH_3$ | O | O—$CH_3$ | i-$C_3H_7$—O |
| $C_6H_{11}$ | $CH_3$ | $CH_3$ | $CH_3$ | 6-$CH_3$ | O | O—$CH_3$ | i-$C_4H_9$—O |
| $C_6H_{11}$ | $CH_3$ | $CH_3$ | $CH_3$ | 6-$CH_3$ | O | O—$CH_3$ | s-$C_4H_9$—O |
| $C_6H_{11}$ | $CH_3$ | $CH_3$ | $CH_3$ | 6-$CH_3$ | O | O—$CH_3$ | t-$C_4H_9$—O |
| $C_6H_{11}$ | $CH_3$ | $CH_3$ | $CH_3$ | 6-$CH_3$ | O | O—$CH_3$ | t-$C_4H_9$—$CH_2$—O |
| $C_6H_{11}$ | $CH_3$ | $CH_3$ | $CH_3$ | 6-$CH_3$ | O | O—$CH_3$ | cyclohexyl-O— |
| $C_6H_{11}$ | $CH_3$ | $CH_3$ | $CH_3$ | 6-$CH_3$ | O | O—$CH_3$ | phenyl-O— |
| $C_6H_{11}$ | $CH_3$ | $CH_3$ | $CH_3$ | 6-$CH_3$ | O | O—$CH_3$ | benzyl-O— |
| $C_6H_{11}$ | $CH_3$ | $CH_3$ | $CH_3$ | 6-$CH_3$ | O | O—$CH_3$ | $CH_3$—S— |
| $C_6H_{11}$ | $CH_3$ | $CH_3$ | $CH_3$ | 6-$CH_3$ | O | O—$CH_3$ | $C_2H_5$—S— |
| $C_6H_{11}$ | $CH_3$ | $CH_3$ | $CH_3$ | 6-$CH_3$ | O | O—$CH_3$ | $C_3H_7$—S— |
| $C_6H_{11}$ | $CH_3$ | $CH_3$ | $CH_3$ | 6-$CH_3$ | O | O—$CH_3$ | i-$C_3H_7$—S— |
| $C_6H_{11}$ | $CH_3$ | $CH_3$ | $CH_3$ | 6-$CH_3$ | O | O—$CH_3$ | i-$C_4H_9$—S— |
| $C_6H_{11}$ | $CH_3$ | $CH_3$ | $CH_3$ | 6-$CH_3$ | O | O—$CH_3$ | s-$C_4H_9$—S— |
| $C_6H_{11}$ | $CH_3$ | $CH_3$ | $CH_3$ | 6-$CH_3$ | O | O—$CH_3$ | t-$C_4H_9$—S— |
| $C_6H_{11}$ | $CH_3$ | $CH_3$ | $CH_3$ | 6-$CH_3$ | O | O—$CH_3$ | t-$C_4H_9$—$CH_2$—S— |
| $C_3H_5$ | $CH_3$ | Cl | Cl | H | O | O—$C_2H_5$ | $CH_3$—O— |
| $C_3H_5$ | $CH_3$ | Cl | Cl | H | O | O—$C_2H_5$ | $C_2H_5$—O— |
| $C_3H_5$ | $CH_3$ | Cl | Cl | H | O | O—$C_2H_5$ | $C_3H_7$—O— |
| $C_3H_5$ | $CH_3$ | Cl | Cl | H | O | O—$C_2H_5$ | i-$C_3H_7$—O |
| $C_3H_5$ | $CH_3$ | Cl | Cl | H | O | O—$C_2H_5$ | i-$C_4H_9$—O |
| $C_3H_5$ | $CH_3$ | Cl | Cl | H | O | O—$C_2H_5$ | s-$C_4H_9$—O |
| $C_3H_5$ | $CH_3$ | Cl | Cl | H | O | O—$C_2H_5$ | t-$C_4H_9$—O |
| $C_3H_5$ | $CH_3$ | Cl | Cl | H | O | O—$C_2H_5$ | t-$C_4H_9$—$CH_2$—O |
| $C_3H_5$ | $CH_3$ | Cl | Cl | H | O | O—$C_2H_5$ | cyclohexyl-O— |
| $C_3H_5$ | $CH_3$ | Cl | Cl | H | O | O—$C_2H_5$ | phenyl-O— |
| $C_3H_5$ | $CH_3$ | Cl | Cl | H | O | O—$C_2H_5$ | benzyl-O— |
| $C_3H_5$ | $CH_3$ | Cl | Cl | H | O | O—$C_2H_5$ | $CH_3$—S— |
| $C_3H_5$ | $CH_3$ | Cl | Cl | H | O | O—$C_2H_5$ | $C_2H_5$—S— |
| $C_3H_5$ | $CH_3$ | Cl | Cl | H | O | O—$C_2H_5$ | $C_3H_7$—S— |

TABLE 5-continued

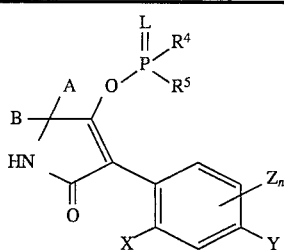

(Ie)

| A* | B | X | Y | $Z_n$ | L | $R^4$ | $R^5$ |
|---|---|---|---|---|---|---|---|
| $C_3H_5$ | $CH_3$ | Cl | Cl | H | O | $O-C_2H_5$ | $i-C_3H_7-S-$ |
| $C_3H_5$ | $CH_3$ | Cl | Cl | H | O | $O-C_2H_5$ | $i-C_4H_9-S-$ |
| $C_3H_5$ | $CH_3$ | Cl | Cl | H | O | $O-C_2H_5$ | $s-C_4H_9-S-$ |
| $C_3H_5$ | $CH_3$ | Cl | Cl | H | O | $O-C_2H_5$ | $t-C_4H_9-S-$ |
| $C_3H_5$ | $CH_3$ | Cl | Cl | H | O | $O-C_2H_5$ | $t-C_4H_9-CH_2-S-$ |
| $C_3H_5$ | $CH_3$ | $CH_3$ | $CH_3$ | H | O | $O-C_2H_5$ | $CH_3-O-$ |
| $C_3H_5$ | $CH_3$ | $CH_3$ | $CH_3$ | H | O | $O-C_2H_5$ | $C_2H_5-O-$ |
| $C_3H_5$ | $CH_3$ | $CH_3$ | $CH_3$ | H | O | $O-C_2H_5$ | $C_3H_7-O-$ |
| $C_3H_5$ | $CH_3$ | $CH_3$ | $CH_3$ | H | O | $O-C_2H_5$ | $i-C_3H_7-O$ |
| $C_3H_5$ | $CH_3$ | $CH_3$ | $CH_3$ | H | O | $O-C_2H_5$ | $i-C_4H_9-O$ |
| $C_3H_5$ | $CH_3$ | $CH_3$ | $CH_3$ | H | O | $O-C_2H_5$ | $s-C_4H_9-O$ |
| $C_3H_5$ | $CH_3$ | $CH_3$ | $CH_3$ | H | O | $O-C_2H_5$ | $t-C_4H_9-O$ |
| $C_3H_5$ | $CH_3$ | $CH_3$ | $CH_3$ | H | O | $O-C_2H_5$ | $t-C_4H_9-CH_2-O$ |
| $C_3H_5$ | $CH_3$ | $CH_3$ | $CH_3$ | H | O | $O-C_2H_5$ | 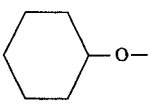 |
| $C_3H_5$ | $CH_3$ | $CH_3$ | $CH_3$ | H | O | $O-C_2H_5$ | 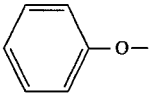 |
| $C_3H_5$ | $CH_3$ | $CH_3$ | $CH_3$ | H | O | $O-C_2H_5$ |  |
| $C_3H_5$ | $CH_3$ | $CH_3$ | $CH_3$ | H | O | $O-C_2H_5$ | $CH_3-S-$ |
| $C_3H_5$ | $CH_3$ | $CH_3$ | $CH_3$ | H | O | $O-C_2H_5$ | $C_2H_5-S-$ |
| $C_3H_5$ | $CH_3$ | $CH_3$ | $CH_3$ | H | O | $O-C_2H_5$ | $C_3H_7-S-$ |
| $C_3H_5$ | $CH_3$ | $CH_3$ | $CH_3$ | H | O | $O-C_2H_5$ | $i-C_3H_7-S-$ |
| $C_3H_5$ | $CH_3$ | $CH_3$ | $CH_3$ | H | O | $O-C_2H_5$ | $i-C_4H_9-S-$ |
| $C_3H_5$ | $CH_3$ | $CH_3$ | $CH_3$ | H | O | $O-C_2H_5$ | $s-C_4H_9-S-$ |
| $C_3H_5$ | $CH_3$ | $CH_3$ | $CH_3$ | H | O | $O-C_2H_5$ | $t-C_4H_9-S-$ |
| $C_3H_5$ | $CH_3$ | $CH_3$ | $CH_3$ | H | O | $O-C_2H_5$ | $t-C_4H_9-CH_2-S-$ |
| $C_3H_5$ | $CH_3$ | $CH_3$ | $CH_3$ | $6-CH_3$ | O | $O-C_2H_5$ | $CH_3-O-$ |
| $C_3H_5$ | $CH_3$ | $CH_3$ | $CH_3$ | $6-CH_3$ | O | $O-C_2H_5$ | $C_2H_5-O-$ |
| $C_3H_5$ | $CH_3$ | $CH_3$ | $CH_3$ | $6-CH_3$ | O | $O-C_2H_5$ | $C_3H_7-O-$ |
| $C_3H_5$ | $CH_3$ | $CH_3$ | $CH_3$ | $6-CH_3$ | O | $O-C_2H_5$ | $i-C_3H_7-O$ |
| $C_3H_5$ | $CH_3$ | $CH_3$ | $CH_3$ | $6-CH_3$ | O | $O-C_2H_5$ | $i-C_4H_9-O$ |
| $C_3H_5$ | $CH_3$ | $CH_3$ | $CH_3$ | $6-CH_3$ | O | $O-C_2H_5$ | $s-C_4H_9-O$ |
| $C_3H_5$ | $CH_3$ | $CH_3$ | $CH_3$ | $6-CH_3$ | O | $O-C_2H_5$ | $t-C_4H_9-O$ |
| $C_3H_5$ | $CH_3$ | $CH_3$ | $CH_3$ | $6-CH_3$ | O | $O-C_2H_5$ | $t-C_4H_9-CH_2-O$ |
| $C_3H_5$ | $CH_3$ | $CH_3$ | $CH_3$ | $6-CH_3$ | O | $O-C_2H_5$ | 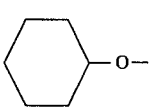 |
| $C_3H_5$ | $CH_3$ | $CH_3$ | $CH_3$ | $6-CH_3$ | O | $O-C_2H_5$ | 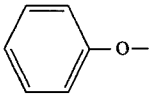 |
| $C_3H_5$ | $CH_3$ | $CH_3$ | $CH_3$ | $6-CH_3$ | O | $O-C_2H_5$ |  |
| $C_3H_5$ | $CH_3$ | $CH_3$ | $CH_3$ | $6-CH_3$ | O | $O-C_2H_5$ | $CH_3-S-$ |
| $C_3H_5$ | $CH_3$ | $CH_3$ | $CH_3$ | $6-CH_3$ | O | $O-C_2H_5$ | $C_2H_5-S-$ |

TABLE 5-continued (Ie)

$$\text{structure: } \begin{array}{c} \text{B} \\ \text{A} \end{array} \text{C=C} \begin{array}{c} \text{O-P(=L)(R}^4\text{)R}^5 \\ \text{phenyl(X,Y,Z}_n\text{)} \end{array} \text{ with HN-C(=O) ring}$$

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | 6-$CH_3$ | O | O—$C_2H_5$ | $C_3H_7$—S— |
| $C_3H_5$ | $CH_3$ | $CH_3$ | $CH_3$ | 6-$CH_3$ | O | O—$C_2H_5$ | i-$C_3H_7$—S— |
| $C_3H_5$ | $CH_3$ | $CH_3$ | $CH_3$ | 6-$CH_3$ | O | O—$C_2H_5$ | i-$C_4H_9$—S— |
| $C_3H_5$ | $CH_3$ | $CH_3$ | $CH_3$ | 6-$CH_3$ | O | O—$C_2H_5$ | s-$C_4H_9$—S— |
| $C_3H_5$ | $CH_3$ | $CH_3$ | $CH_3$ | 6-$CH_3$ | O | O—$C_2H_5$ | t-$C_4H_9$—S— |
| $C_3H_5$ | $CH_3$ | $CH_3$ | $CH_3$ | 6-$CH_3$ | O | O—$C_2H_5$ | t-$C_4H_9$—$CH_2$—S— |
| $C_6H_{11}$ | $CH_3$ | Cl | Cl | H | O | O—C2H5 | $CH_3$—O— |
| $C_6H_{11}$ | $CH_3$ | Cl | Cl | H | O | O—$C_2H_5$ | $C_2H_5$—O— |
| $C_6H_{11}$ | $CH_3$ | Cl | Cl | H | O | O—$C_2H_5$ | $C_3H_7$—O— |
| $C_6H_{11}$ | $CH_3$ | Cl | Cl | H | O | O—$C_2H_5$ | i-$C_3H_7$—O |
| $C_6H_{11}$ | $CH_3$ | Cl | Cl | H | O | O—$C_2H_5$ | i-$C_4H_9$—O |
| $C_6H_{11}$ | $CH_3$ | Cl | Cl | H | O | O—$C_2H_5$ | s-$C_4H_9$—O |
| $C_6H_{11}$ | $CH_3$ | Cl | Cl | H | O | O—$C_2H_5$ | t-$C_4H_9$—O |
| $C_6H_{11}$ | $CH_3$ | Cl | Cl | H | O | O—$C_2H_5$ | t-$C_4H_9$—$CH_2$—O |
| $C_6H_{11}$ | $CH_3$ | Cl | Cl | H | O | O—$C_2H_5$ | cyclohexyl-O— |
| $C_6H_{11}$ | $CH_3$ | Cl | Cl | H | O | O—$C_2H_5$ | phenyl-O— |
| $C_6H_{11}$ | $CH_3$ | Cl | Cl | H | O | O—$C_2H_5$ | benzyl-O— |
| $C_6H_{11}$ | $CH_3$ | Cl | Cl | H | O | O—$C_2H_5$ | $CH_3$—S— |
| $C_6H_{11}$ | $CH_3$ | Cl | Cl | H | O | O—$C_2H_5$ | $C_2H_5$—S— |
| $C_6H_{11}$ | $CH_3$ | Cl | Cl | H | O | O—$C_2H_5$ | $C_3H_7$—S— |
| $C_6H_{11}$ | $CH_3$ | Cl | Cl | H | O | O—$C_2H_5$ | i-$C_3H_7$—S— |
| $C_6H_{11}$ | $CH_3$ | Cl | Cl | H | O | O—$C_2H_5$ | i-$C_4H_9$—S— |
| $C_6H_{11}$ | $CH_3$ | Cl | Cl | H | O | O—$C_2H_5$ | s-$C_4H_9$—S— |
| $C_6H_{11}$ | $CH_3$ | Cl | Cl | H | O | O—$C_2H_5$ | t-$C_4H_9$—S— |
| $C_6H_{11}$ | $CH_3$ | Cl | Cl | H | O | O—$C_2H_5$ | t-$C_4H_9$—$CH_2$—S— |
| $C_6H_{11}$ | $CH_3$ | $CH_3$ | $CH_3$ | H | O | O—$C_2H_5$ | $CH_3$—O— |
| $C_6H_{11}$ | $CH_3$ | $CH_3$ | $CH_3$ | H | O | O—$C_2H_5$ | $C_2H_5$—O— |
| $C_6H_{11}$ | $CH_3$ | $CH_3$ | $CH_3$ | H | O | O—$C_2H_5$ | $C_3H_7$—O— |
| $C_6H_{11}$ | $CH_3$ | $CH_3$ | $CH_3$ | H | O | O—$C_2H_5$ | i-$C_3H_7$—O |
| $C_6H_{11}$ | $CH_3$ | $CH_3$ | $CH_3$ | H | O | O—$C_2H_5$ | i-$C_4H_9$—O |
| $C_6H_{11}$ | $CH_3$ | $CH_3$ | $CH_3$ | H | O | O—$C_2H_5$ | s-$C_4H_9$—O |
| $C_6H_{11}$ | $CH_3$ | $CH_3$ | $CH_3$ | H | O | O—$C_2H_5$ | t-$C_4H_9$—O |
| $C_6H_{11}$ | $CH_3$ | $CH_3$ | $CH_3$ | H | O | O—$C_2H_5$ | t-$C_4H_9$—$CH_2$—O |
| $C_6H_{11}$ | $CH_3$ | $CH_3$ | $CH_3$ | H | O | O—$C_2H_5$ | cyclohexyl-O— |
| $C_6H_{11}$ | $CH_3$ | $CH_3$ | $CH_3$ | H | O | O—$C_2H_5$ | phenyl-O— |
| $C_6H_{11}$ | $CH_3$ | $CH_3$ | $CH_3$ | H | O | O—$C_2H_5$ | benzyl-O— |
| $C_6H_{11}$ | $CH_3$ | $CH_3$ | $CH_3$ | H | O | O—$C_2H_5$ | $CH_3$—S— |

TABLE 5-continued

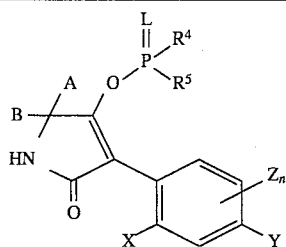

(Ie)

| A* | B | X | Y | $Z_n$ | L | $R^4$ | $R^5$ |
|---|---|---|---|---|---|---|---|
| $C_6H_{11}$ | $CH_3$ | $CH_3$ | $CH_3$ | H | O | $O-C_2H_5$ | $C_2H_5-S-$ |
| $C_6H_{11}$ | $CH_3$ | $CH_3$ | $CH_3$ | H | O | $O-C_2H_5$ | $C_3H_7-S-$ |
| $C_6H_{11}$ | $CH_3$ | $CH_3$ | $CH_3$ | H | O | $O-C_2H_5$ | $i-C_3H_7-S-$ |
| $C_6H_{11}$ | $CH_3$ | $CH_3$ | $CH_3$ | H | O | $O-C_2H_5$ | $i-C_4H_9-S-$ |
| $C_6H_{11}$ | $CH_3$ | $CH_3$ | $CH_3$ | H | O | $O-C_2H_5$ | $s-C_4H_9-S-$ |
| $C_6H_{11}$ | $CH_3$ | $CH_3$ | $CH_3$ | H | O | $O-C_2H_5$ | $t-C_4H_9-S-$ |
| $C_6H_{11}$ | $CH_3$ | $CH_3$ | $CH_3$ | H | O | $O-C_2H_5$ | $t-C_4H_9-CH_2-S-$ |
| $C_6H_{11}$ | $CH_3$ | $CH_3$ | $CH_3$ | $6-CH_3$ | O | $O-C_2H_5$ | $CH_3-O-$ |
| $C_6H_{11}$ | $CH_3$ | $CH_3$ | $CH_3$ | $6-CH_3$ | O | $O-C_2H_5$ | $C_2H_5-O-$ |
| $C_6H_{11}$ | $CH_3$ | $CH_3$ | $CH_3$ | $6-CH_3$ | O | $O-C_2H_5$ | $C_3H_7-O-$ |
| $C_6H_{11}$ | $CH_3$ | $CH_3$ | $CH_3$ | $6-CH_3$ | O | $O-C_2H_5$ | $i-C_3H_7-O$ |
| $C_6H_{11}$ | $CH_3$ | $CH_3$ | $CH_3$ | $6-CH_3$ | O | $O-C_2H_5$ | $i-C_4H_9-O$ |
| $C_6H_{11}$ | $CH_3$ | $CH_3$ | $CH_3$ | $6-CH_3$ | O | $O-C_2H_5$ | $s-C_4H_9-O$ |
| $C_6H_{11}$ | $CH_3$ | $CH_3$ | $CH_3$ | $6-CH_3$ | O | $O-C_2H_5$ | $t-C_4H_9-O$ |
| $C_6H_{11}$ | $CH_3$ | $CH_3$ | $CH_3$ | $6-CH_3$ | O | $O-C_2H_5$ | $t-C_4H_9-CH_2-O$ |
| $C_6H_{11}$ | $CH_3$ | $CH_3$ | $CH_3$ | $6-CH_3$ | O | $O-C_2H_5$ | 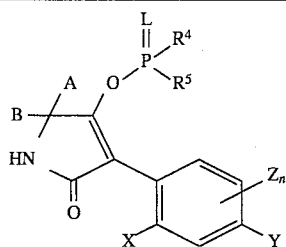 |
| $C_6H_{11}$ | $CH_3$ | $CH_3$ | $CH_3$ | $6-CH_3$ | O | $O-C_2H_5$ | 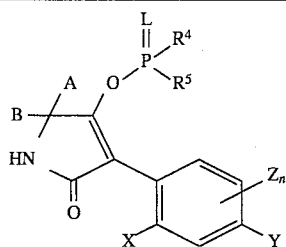 |
| $C_6H_{11}$ | $CH_3$ | $CH_3$ | $CH_3$ | $6-CH_3$ | O | $O-C_2H_5$ | 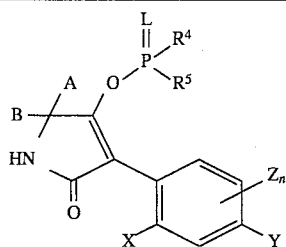 |
| $C_6H_{11}$ | $CH_3$ | $CH_3$ | $CH_3$ | $6-CH_3$ | O | $O-C_2H_5$ | $CH_3-S-$ |
| $C_6H_{11}$ | $CH_3$ | $CH_3$ | $CH_3$ | $6-CH_3$ | O | $O-C_2H_5$ | $C_2H_5-S-$ |
| $C_6H_{11}$ | $CH_3$ | $CH_3$ | $CH_3$ | $6-CH_3$ | O | $O-C_2H_5$ | $C_3H_7-S-$ |
| $C_6H_{11}$ | $CH_3$ | $CH_3$ | $CH_3$ | $6-CH_3$ | O | $O-C_2H_5$ | $i-C_3H_7-S-$ |
| $C_6H_{11}$ | $CH_3$ | $CH_3$ | $CH_3$ | $6-CH_3$ | O | $O-C_2H_5$ | $i-C_4H_9-S-$ |
| $C_6H_{11}$ | $CH_3$ | $CH_3$ | $CH_3$ | $6-CH_3$ | O | $O-C_2H_5$ | $s-C_4H_9-S-$ |
| $C_6H_{11}$ | $CH_3$ | $CH_3$ | $CH_3$ | $6-CH_3$ | O | $O-C_2H_5$ | $t-C_4H_9-S-$ |
| $C_6H_{11}$ | $CH_3$ | $CH_3$ | $CH_3$ | $6-CH_3$ | O | $O-C_2H_5$ | $t-C_4H_9-CH_2-S-$ |
| $C_3H_5$ | $CH_3$ | Cl | Cl | H | S | $C_2H_5$ | $CH_3-O-$ |
| $C_3H_5$ | $CH_3$ | Cl | Cl | H | S | $C_2H_5$ | $C_2H_5-O-$ |
| $C_3H_5$ | $CH_3$ | Cl | Cl | H | S | $C_2H_5$ | $C_3H_7-O-$ |
| $C_3H_5$ | $CH_3$ | Cl | Cl | H | S | $C_2H_5$ | $i-C_3H_7-O$ |
| $C_3H_5$ | $CH_3$ | Cl | Cl | H | S | $C_2H_5$ | $i-C_4H_9-O$ |
| $C_3H_5$ | $CH_3$ | Cl | Cl | H | S | $C_2H_5$ | $s-C_4H_9-O$ |
| $C_3H_5$ | $CH_3$ | Cl | Cl | H | S | $C_2H_5$ | $t-C_4H_9-O$ |
| $C_3H_5$ | $CH_3$ | Cl | Cl | H | S | $C_2H_5$ | $t-C_4H_9-CH_2-O$ |
| $C_3H_5$ | $CH_3$ | Cl | Cl | H | S | $C_2H_5$ | 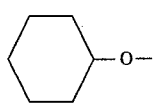 |
| $C_3H_5$ | $CH_3$ | Cl | Cl | H | S | $C_2H_5$ | 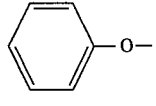 |
| $C_3H_5$ | $CH_3$ | Cl | Cl | H | S | $C_2H_5$ | 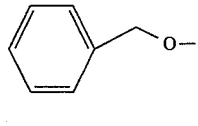 |

TABLE 5-continued

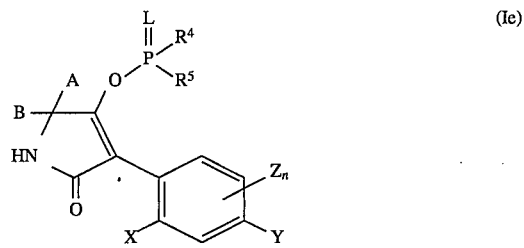

(Ie)

| A* | B | X | Y | $Z_n$ | L | $R^4$ | $R^5$ |
|---|---|---|---|---|---|---|---|
| $C_3H_5$ | $CH_3$ | Cl | Cl | H | S | $C_2H_5$ | $CH_3-S-$ |
| $C_3H_5$ | $CH_3$ | Cl | Cl | H | S | $C_2H_5$ | $C_2H_5-S-$ |
| $C_3H_5$ | $CH_3$ | Cl | Cl | H | S | $C_2H_5$ | $C_3H_7-S-$ |
| $C_3H_5$ | $CH_3$ | Cl | Cl | H | S | $C_2H_5$ | $i-C_3H_7-S-$ |
| $C_3H_5$ | $CH_3$ | Cl | Cl | H | S | $C_2H_5$ | $i-C_4H_9-S-$ |
| $C_3H_5$ | $CH_3$ | Cl | Cl | H | S | $C_2H_5$ | $s-C_4H_9-S-$ |
| $C_3H_5$ | $CH_3$ | Cl | Cl | H | S | $C_2H_5$ | $t-C_4H_9-S-$ |
| $C_3H_5$ | $CH_3$ | Cl | Cl | H | S | $C_2H_5$ | $t-C_4H_9-CH_2-S-$ |
| $C_3H_5$ | $CH_3$ | $CH_3$ | $CH_3$ | H | S | $C_2H_5$ | $CH_3-O-$ |
| $C_3H_5$ | $CH_3$ | $CH_3$ | $CH_3$ | H | S | $C_2H_5$ | $C_2H_5-O-$ |
| $C_3H_5$ | $CH_3$ | $CH_3$ | $CH_3$ | H | S | $C_2H_5$ | $C_3H_7-O-$ |
| $C_3H_5$ | $CH_3$ | $CH_3$ | $CH_3$ | H | S | $C_2H_5$ | $i-C_3H_7-O$ |
| $C_3H_5$ | $CH_3$ | $CH_3$ | $CH_3$ | H | S | $C_2H_5$ | $i-C_4H_9-O$ |
| $C_3H_5$ | $CH_3$ | $CH_3$ | $CH_3$ | H | S | $C_2H_5$ | $s-C_4H_9-O$ |
| $C_3H_5$ | $CH_3$ | $CH_3$ | $CH_3$ | H | S | $C_2H_5$ | $t-C_4H_9-O$ |
| $C_3H_5$ | $CH_3$ | $CH_3$ | $CH_3$ | H | S | $C_2H_5$ | $t-C_4H_9-CH_2-O$ |
| $C_3H_5$ | $CH_3$ | $CH_3$ | $CH_3$ | H | S | $C_2H_5$ | cyclohexyl-O- |
| $C_3H_5$ | $CH_3$ | $CH_3$ | $CH_3$ | H | S | $C_2H_5$ | phenyl-O- |
| $C_3H_5$ | $CH_3$ | $CH_3$ | $CH_3$ | H | S | $C_2H_5$ | benzyl-O- |
| $C_3H_5$ | $CH_3$ | $CH_3$ | $CH_3$ | H | S | $C_2H_5$ | $CH_3-S-$ |
| $C_3H_5$ | $CH_3$ | $CH_3$ | $CH_3$ | H | S | $C_2H_5$ | $C_2H_5-S-$ |
| $C_3H_5$ | $CH_3$ | $CH_3$ | $CH_3$ | H | S | $C_2H_5$ | $C_3H_7-S-$ |
| $C_3H_5$ | $CH_3$ | $CH_3$ | $CH_3$ | H | S | $C_2H_5$ | $i-C_3H_7-S-$ |
| $C_3H_5$ | $CH_3$ | $CH_3$ | $CH_3$ | H | S | $C_2H_5$ | $i-C_4H_9-S-$ |
| $C_3H_5$ | $CH_3$ | $CH_3$ | $CH_3$ | H | S | $C_2H_5$ | $s-C_4H_9-S-$ |
| $C_3H_5$ | $CH_3$ | $CH_3$ | $CH_3$ | H | S | $C_2H_5$ | $t-C_4H_9-S-$ |
| $C_3H_5$ | $CH_3$ | $CH_3$ | $CH_3$ | H | S | $C_2H_5$ | $t-C_4H_9-CH_2-S-$ |
| $C_3H_5$ | $CH_3$ | $CH_3$ | $CH_3$ | $6-CH_3$ | S | $C_2H_5$ | $CH_3-O-$ |
| $C_3H_5$ | $CH_3$ | $CH_3$ | $CH_3$ | $6-CH_3$ | S | $C_2H_5$ | $C_2H_5-O-$ |
| $C_3H_5$ | $CH_3$ | $CH_3$ | $CH_3$ | $6-CH_3$ | S | $C_2H_5$ | $C_3H_7-O-$ |
| $C_3H_5$ | $CH_3$ | $CH_3$ | $CH_3$ | $6-CH_3$ | S | $C_2H_5$ | $i-C_3H_7-O$ |
| $C_3H_5$ | $CH_3$ | $CH_3$ | $CH_3$ | $6-CH_3$ | S | $C_2H_5$ | $i-C_4H_9-O$ |
| $C_3H_5$ | $CH_3$ | $CH_3$ | $CH_3$ | $6-CH_3$ | S | $C_2H_5$ | $s-C_4H_9-O$ |
| $C_3H_5$ | $CH_3$ | $CH_3$ | $CH_3$ | $6-CH_3$ | S | $C_2H_5$ | $t-C_4H_9-O$ |
| $C_3H_5$ | $CH_3$ | $CH_3$ | $CH_3$ | $6-CH_3$ | S | $C_2H_5$ | $t-C_4H_9-CH_2-O$ |
| $C_3H_5$ | $CH_3$ | $CH_3$ | $CH_3$ | $6-CH_3$ | S | $C_2H_5$ | cyclohexyl-O- |
| $C_3H_5$ | $CH_3$ | $CH_3$ | $CH_3$ | $6-CH_3$ | S | $C_2H_5$ | phenyl-O- |
| $C_3H_5$ | $CH_3$ | $CH_3$ | $CH_3$ | $6-CH_3$ | S | $C_2H_5$ | benzyl-O- |

TABLE 5-continued (Ie)

[Structure: phosphorus compound with formula showing P(=L)(R⁴)(R⁵) attached via O to a cyclic structure with A, B, HN, C=O groups, and substituted phenyl ring with X, Y, Z_n]

| A* | B | X | Y | Z_n | L | R⁴ | R⁵ |
|---|---|---|---|---|---|---|---|
| $C_3H_5$ | $CH_3$ | $CH_3$ | $CH_3$ | 6-$CH_3$ | S | $C_2H_5$ | $CH_3-S-$ |
| $C_3H_5$ | $CH_3$ | $CH_3$ | $CH_3$ | 6-$CH_3$ | S | $C_2H_5$ | $C_2H_5-S-$ |
| $C_3H_5$ | $CH_3$ | $CH_3$ | $CH_3$ | 6-$CH_3$ | S | $C_2H_5$ | $C_3H_7-S-$ |
| $C_3H_5$ | $CH_3$ | $CH_3$ | $CH_3$ | 6-$CH_3$ | S | $C_2H_5$ | $i-C_3H_7-S-$ |
| $C_3H_5$ | $CH_3$ | $CH_3$ | $CH_3$ | 6-$CH_3$ | S | $C_2H_5$ | $i-C_4H_9-S-$ |
| $C_3H_5$ | $CH_3$ | $CH_3$ | $CH_3$ | 6-$CH_3$ | S | $C_2H_5$ | $s-C_4H_9-S-$ |
| $C_3H_5$ | $CH_3$ | $CH_3$ | $CH_3$ | 6-$CH_3$ | S | $C_2H_5$ | $t-C_4H_9-S-$ |
| $C_3H_5$ | $CH_3$ | $CH_3$ | $CH_3$ | 6-$CH_3$ | S | $C_2H_5$ | $t-C_4H_9-CH_2-S-$ |
| $C_6H_{11}$ | $CH_3$ | Cl | Cl | H | S | $C_2H_5$ | $CH_3-O-$ |
| $C_6H_{11}$ | $CH_3$ | Cl | Cl | H | S | $C_2H_5$ | $C_2H_5-O-$ |
| $C_6H_{11}$ | $CH_3$ | Cl | Cl | H | S | $C_2H_5$ | $C_3H_7-O-$ |
| $C_6H_{11}$ | $CH_3$ | Cl | Cl | H | S | $C_2H_5$ | $i-C_3H_7-O$ |
| $C_6H_{11}$ | $CH_3$ | Cl | Cl | H | S | $C_2H_5$ | $i-C_4H_9-O$ |
| $C_6H_{11}$ | $CH_3$ | Cl | Cl | H | S | $C_2H_5$ | $s-C_4H_9-O$ |
| $C_6H_{11}$ | $CH_3$ | Cl | Cl | H | S | $C_2H_5$ | $t-C_4H_9-O$ |
| $C_6H_{11}$ | $CH_3$ | Cl | Cl | H | S | $C_2H_5$ | $t-C_4H_9-CH_2-O$ |
| $C_6H_{11}$ | $CH_3$ | Cl | Cl | H | S | $C_2H_5$ | cyclohexyl-O— |
| $C_6H_{11}$ | $CH_3$ | Cl | Cl | H | S | $C_2H_5$ | phenyl-O— |
| $C_6H_{11}$ | $CH_3$ | Cl | Cl | H | S | $C_2H_5$ | benzyl-O— |
| $C_6H_{11}$ | $CH_3$ | Cl | Cl | H | S | $C_2H_5$ | $CH_3-S-$ |
| $C_6H_{11}$ | $CH_3$ | Cl | Cl | H | S | $C_2H_5$ | $C_2H_5-S-$ |
| $C_6H_{11}$ | $CH_3$ | Cl | Cl | H | S | $C_2H_5$ | $C_3H_7-S-$ |
| $C_6H_{11}$ | $CH_3$ | Cl | Cl | H | S | $C_2H_5$ | $i-C_3H_7-S-$ |
| $C_6H_{11}$ | $CH_3$ | Cl | Cl | H | S | $C_2H_5$ | $i-C_4H_9-S-$ |
| $C_6H_{11}$ | $CH_3$ | Cl | Cl | H | S | $C_2H_5$ | $s-C_4H_9-S-$ |
| $C_6H_{11}$ | $CH_3$ | Cl | Cl | H | S | $C_2H_5$ | $t-C_4H_9-S-$ |
| $C_6H_{11}$ | $CH_3$ | Cl | Cl | H | S | $C_2H_5$ | $t-C_4H_9-CH_2-S-$ |
| $C_6H_{11}$ | $CH_3$ | $CH_3$ | $CH_3$ | H | S | $C_2H_5$ | $CH_3-O-$ |
| $C_6H_{11}$ | $CH_3$ | $CH_3$ | $CH_3$ | H | S | $C_2H_5$ | $C_2H_5-O-$ |
| $C_6H_{11}$ | $CH_3$ | $CH_3$ | $CH_3$ | H | S | $C_2H_5$ | $C_3H_7-O-$ |
| $C_6H_{11}$ | $CH_3$ | $CH_3$ | $CH_3$ | H | S | $C_2H_5$ | $i-C_3H_7-O$ |
| $C_6H_{11}$ | $CH_3$ | $CH_3$ | $CH_3$ | H | S | $C_2H_5$ | $i-C_4H_9-O$ |
| $C_6H_{11}$ | $CH_3$ | $CH_3$ | $CH_3$ | H | S | $C_2H_5$ | $s-C_4H_9-O$ |
| $C_6H_{11}$ | $CH_3$ | $CH_3$ | $CH_3$ | H | S | $C_2H_5$ | $t-C_4H_9-O$ |
| $C_6H_{11}$ | $CH_3$ | $CH_3$ | $CH_3$ | H | S | $C_2H_5$ | $t-C_4H_9-CH_2-O$ |
| $C_6H_{11}$ | $CH_3$ | $CH_3$ | $CH_3$ | H | S | $C_2H_5$ | cyclohexyl-O— |
| $C_6H_{11}$ | $CH_3$ | $CH_3$ | $CH_3$ | H | S | $C_2H_5$ | phenyl-O— |

TABLE 5-continued $$\text{(Ie)}$$

Structure (Ie): a ring system with substituents A, B, HN–C(=O)–, attached to a phenyl ring bearing X, Y, $Z_n$ substituents, and an O–P(=L)(R⁴)(R⁵) phosphorus group.

| A* | B | X | Y | $Z_n$ | L | R⁴ | R⁵ |
|---|---|---|---|---|---|---|---|
| $C_6H_{11}$ | $CH_3$ | $CH_3$ | $CH_3$ | H | S | $C_2H_5$ | benzyl-O– (C₆H₅–CH₂–O–) |
| $C_6H_{11}$ | $CH_3$ | $CH_3$ | $CH_3$ | H | S | $C_2H_5$ | $CH_3-S-$ |
| $C_6H_{11}$ | $CH_3$ | $CH_3$ | $CH_3$ | H | S | $C_2H_5$ | $C_2H_5-S-$ |
| $C_6H_{11}$ | $CH_3$ | $CH_3$ | $CH_3$ | H | S | $C_2H_5$ | $C_3H_7-S-$ |
| $C_6H_{11}$ | $CH_3$ | $CH_3$ | $CH_3$ | H | S | $C_2H_5$ | $i\text{-}C_3H_7-S-$ |
| $C_6H_{11}$ | $CH_3$ | $CH_3$ | $CH_3$ | H | S | $C_2H_5$ | $i\text{-}C_4H_9-S-$ |
| $C_6H_{11}$ | $CH_3$ | $CH_3$ | $CH_3$ | H | S | $C_2H_5$ | $s\text{-}C_4H_9-S-$ |
| $C_6H_{11}$ | $CH_3$ | $CH_3$ | $CH_3$ | H | S | $C_2H_5$ | $t\text{-}C_4H_9-S-$ |
| $C_6H_{11}$ | $CH_3$ | $CH_3$ | $CH_3$ | H | S | $C_2H_5$ | $t\text{-}C_4H_9-CH_2-S-$ |
| $C_6H_{11}$ | $CH_3$ | $CH_3$ | $CH_3$ | 6-$CH_3$ | S | $C_2H_5$ | $CH_3-O-$ |
| $C_6H_{11}$ | $CH_3$ | $CH_3$ | $CH_3$ | 6-$CH_3$ | S | $C_2H_5$ | $C_2H_5-O-$ |
| $C_6H_{11}$ | $CH_3$ | $CH_3$ | $CH_3$ | 6-$CH_3$ | S | $C_2H_5$ | $C_3H_7-O-$ |
| $C_6H_{11}$ | $CH_3$ | $CH_3$ | $CH_3$ | 6-$CH_3$ | S | $C_2H_5$ | $i\text{-}C_3H_7-O$ |
| $C_6H_{11}$ | $CH_3$ | $CH_3$ | $CH_3$ | 6-$CH_3$ | S | $C_2H_5$ | $i\text{-}C_4H_9-O$ |
| $C_6H_{11}$ | $CH_3$ | $CH_3$ | $CH_3$ | 6-$CH_3$ | S | $C_2H_5$ | $s\text{-}C_4H_9-O$ |
| $C_6H_{11}$ | $CH_3$ | $CH_3$ | $CH_3$ | 6-$CH_3$ | S | $C_2H_5$ | $t\text{-}C_4H_9-O$ |
| $C_6H_{11}$ | $CH_3$ | $CH_3$ | $CH_3$ | 6-$CH_3$ | S | $C_2H_5$ | $t\text{-}C_4H_9-CH_2-O$ |
| $C_6H_{11}$ | $CH_3$ | $CH_3$ | $CH_3$ | 6-$CH_3$ | S | $C_2H_5$ | cyclohexyl-O– |
| $C_6H_{11}$ | $CH_3$ | $CH_3$ | $CH_3$ | 6-$CH_3$ | S | $C_2H_5$ | phenyl-O– |
| $C_6H_{11}$ | $CH_3$ | $CH_3$ | $CH_3$ | 6-$CH_3$ | S | $C_2H_5$ | benzyl-O– (C₆H₅–CH₂–O–) |
| $C_6H_{11}$ | $CH_3$ | $CH_3$ | $CH_3$ | 6-$CH_3$ | S | $C_2H_5$ | $CH_3-S-$ |
| $C_6H_{11}$ | $CH_3$ | $CH_3$ | $CH_3$ | 6-$CH_3$ | S | $C_2H_5$ | $C_2H_5-S-$ |
| $C_6H_{11}$ | $CH_3$ | $CH_3$ | $CH_3$ | 6-$CH_3$ | S | $C_2H_5$ | $C_3H_7-S-$ |
| $C_6H_{11}$ | $CH_3$ | $CH_3$ | $CH_3$ | 6-$CH_3$ | S | $C_2H_5$ | $i\text{-}C_3H_7-S-$ |
| $C_6H_{11}$ | $CH_3$ | $CH_3$ | $CH_3$ | 6-$CH_3$ | S | $C_2H_5$ | $i\text{-}C_4H_9-S-$ |
| $C_6H_{11}$ | $CH_3$ | $CH_3$ | $CH_3$ | 6-$CH_3$ | S | $C_2H_5$ | $s\text{-}C_4H_9-S-$ |
| $C_6H_{11}$ | $CH_3$ | $CH_3$ | $CH_3$ | 6-$CH_3$ | S | $C_2H_5$ | $t\text{-}C_4H_9-S-$ |
| $C_6H_{11}$ | $CH_3$ | $CH_3$ | $CH_3$ | 6-$CH_3$ | S | $C_2H_5$ | $t\text{-}C_4H_9-CH_2-S-$ |
| $C_3H_5$ | $CH_3$ | Cl | Cl | H | S | $CH_3$ | $CH_3-O-$ |
| $C_3H_5$ | $CH_3$ | Cl | Cl | H | S | $CH_3$ | $C_2H_5-O-$ |
| $C_3H_5$ | $CH_3$ | Cl | Cl | H | S | $CH_3$ | $C_3H_7-O-$ |
| $C_3H_5$ | $CH_3$ | Cl | Cl | H | S | $CH_3$ | $i\text{-}C_3H_7-O$ |
| $C_3H_5$ | $CH_3$ | Cl | Cl | H | S | $CH_3$ | $i\text{-}C_4H_9-O$ |
| $C_3H_5$ | $CH_3$ | Cl | Cl | H | S | $CH_3$ | $s\text{-}C_4H_9-O$ |
| $C_3H_5$ | $CH_3$ | Cl | Cl | H | S | $CH_3$ | $t\text{-}C_4H_9-O$ |
| $C_3H_5$ | $CH_3$ | Cl | Cl | H | S | $CH_3$ | $t\text{-}C_4H_9-CH_2-O$ |
| $C_3H_5$ | $CH_3$ | Cl | Cl | H | S | $CH_3$ | cyclohexyl-O– |
| $C_3H_5$ | $CH_3$ | Cl | Cl | H | S | $CH_3$ | phenyl-O– |

TABLE 5-continued

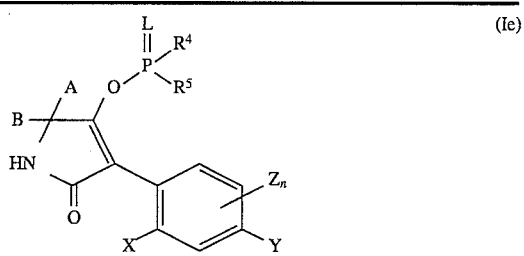

(Ie)

| A* | B | X | Y | $Z_n$ | L | $R^4$ | $R^5$ |
|---|---|---|---|---|---|---|---|
| $C_3H_5$ | $CH_3$ | Cl | Cl | H | S | $CH_3$ | benzyl-$O-$ |
| $C_3H_5$ | $CH_3$ | Cl | Cl | H | S | $CH_3$ | $CH_3-S-$ |
| $C_3H_5$ | $CH_3$ | Cl | Cl | H | S | $CH_3$ | $C_2H_5-S-$ |
| $C_3H_5$ | $CH_3$ | Cl | Cl | H | S | $CH_3$ | $C_3H_7-S-$ |
| $C_3H_5$ | $CH_3$ | Cl | Cl | H | S | $CH_3$ | $i-C_3H_7-S-$ |
| $C_3H_5$ | $CH_3$ | Cl | Cl | H | S | $CH_3$ | $i-C_4H_9-S-$ |
| $C_3H_5$ | $CH_3$ | Cl | Cl | H | S | $CH_3$ | $s-C_4H_9-S-$ |
| $C_3H_5$ | $CH_3$ | Cl | Cl | H | S | $CH_3$ | $t-C_4H_9-S-$ |
| $C_3H_5$ | $CH_3$ | Cl | Cl | H | S | $CH_3$ | $t-C_4H_9-CH_2-S-$ |
| $C_3H_5$ | $CH_3$ | $CH_3$ | $CH_3$ | H | S | $CH_3$ | $CH_3-O-$ |
| $C_3H_5$ | $CH_3$ | $CH_3$ | $CH_3$ | H | S | $CH_3$ | $C_2H_5-O-$ |
| $C_3H_5$ | $CH_3$ | $CH_3$ | $CH_3$ | H | S | $CH_3$ | $C_3H_7-O-$ |
| $C_3H_5$ | $CH_3$ | $CH_3$ | $CH_3$ | H | S | $CH_3$ | $i-C_3H_7-O$ |
| $C_3H_5$ | $CH_3$ | $CH_3$ | $CH_3$ | H | S | $CH_3$ | $i-C_4H_9-O$ |
| $C_3H_5$ | $CH_3$ | $CH_3$ | $CH_3$ | H | S | $CH_3$ | $s-C_4H_9-O$ |
| $C_3H_5$ | $CH_3$ | $CH_3$ | $CH_3$ | H | S | $CH_3$ | $t-C_4H_9-O$ |
| $C_3H_5$ | $CH_3$ | $CH_3$ | $CH_3$ | H | S | $CH_3$ | $t-C_4H_9-CH_2-O$ |
| $C_3H_5$ | $CH_3$ | $CH_3$ | $CH_3$ | H | S | $CH_3$ | cyclohexyl-$O-$ |
| $C_3H_5$ | $CH_3$ | $CH_3$ | $CH_3$ | H | S | $CH_3$ | phenyl-$O-$ |
| $C_3H_5$ | $CH_3$ | $CH_3$ | $CH_3$ | H | S | $CH_3$ | benzyl-$O-$ |
| $C_3H_5$ | $CH_3$ | $CH_3$ | $CH_3$ | H | S | $CH_3$ | $CH_3-S-$ |
| $C_3H_5$ | $CH_3$ | $CH_3$ | $CH_3$ | H | S | $CH_3$ | $C_2H_5-S-$ |
| $C_3H_5$ | $CH_3$ | $CH_3$ | $CH_3$ | H | S | $CH_3$ | $C_3H_7-S-$ |
| $C_3H_5$ | $CH_3$ | $CH_3$ | $CH_3$ | H | S | $CH_3$ | $i-C_3H_7-S-$ |
| $C_3H_5$ | $CH_3$ | $CH_3$ | $CH_3$ | H | S | $CH_3$ | $i-C_4H_9-S-$ |
| $C_3H_5$ | $CH_3$ | $CH_3$ | $CH_3$ | H | S | $CH_3$ | $s-C_4H_9-S-$ |
| $C_3H_5$ | $CH_3$ | $CH_3$ | $CH_3$ | H | S | $CH_3$ | $t-C_4H_9-S-$ |
| $C_3H_5$ | $CH_3$ | $CH_3$ | $CH_3$ | H | S | $CH_3$ | $t-C_4H_9-CH_2-S-$ |
| $C_3H_5$ | $CH_3$ | $CH_3$ | $CH_3$ | $6-CH_3$ | S | $CH_3$ | $CH_3-O-$ |
| $C_3H_5$ | $CH_3$ | $CH_3$ | $CH_3$ | $6-CH_3$ | S | $CH_3$ | $C_2H_5-O-$ |
| $C_3H_5$ | $CH_3$ | $CH_3$ | $CH_3$ | $6-CH_3$ | S | $CH_3$ | $C_3H_7-O-$ |
| $C_3H_5$ | $CH_3$ | $CH_3$ | $CH_3$ | $6-CH_3$ | S | $CH_3$ | $i-C_3H_7-O$ |
| $C_3H_5$ | $CH_3$ | $CH_3$ | $CH_3$ | $6-CH_3$ | S | $CH_3$ | $i-C_4H_9-O$ |
| $C_3H_5$ | $CH_3$ | $CH_3$ | $CH_3$ | $6-CH_3$ | S | $CH_3$ | $s-C_4H_9-O$ |
| $C_3H_5$ | $CH_3$ | $CH_3$ | $CH_3$ | $6-CH_3$ | S | $CH_3$ | $t-C_4H_9-O$ |
| $C_3H_5$ | $CH_3$ | $CH_3$ | $CH_3$ | $6-CH_3$ | S | $CH_3$ | $t-C_4H_9-CH_2-O$ |
| $C_3H_5$ | $CH_3$ | $CH_3$ | $CH_3$ | $6-CH_3$ | S | $CH_3$ | cyclohexyl-$O-$ |

TABLE 5-continued (Ie) Structure: phosphorus compound with substituents A, B, L, R⁴, R⁵, X, Y, Z_n on a cyclic framework containing HN and C=O groups.

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | 6-$CH_3$ | S | $CH_3$ | phenyl-O— |
| $C_3H_5$ | $CH_3$ | $CH_3$ | $CH_3$ | 6-$CH_3$ | S | $CH_3$ | benzyl-O— |
| $C_3H_5$ | $CH_3$ | $CH_3$ | $CH_3$ | 6-$CH_3$ | S | $CH_3$ | $CH_3$—S— |
| $C_3H_5$ | $CH_3$ | $CH_3$ | $CH_3$ | 6-$CH_3$ | S | $CH_3$ | $C_2H_5$—S— |
| $C_3H_5$ | $CH_3$ | $CH_3$ | $CH_3$ | 6-$CH_3$ | S | $CH_3$ | $C_3H_7$—S— |
| $C_3H_5$ | $CH_3$ | $CH_3$ | $CH_3$ | 6-$CH_3$ | S | $CH_3$ | i-$C_3H_7$—S— |
| $C_3H_5$ | $CH_3$ | $CH_3$ | $CH_3$ | 6-$CH_3$ | S | $CH_3$ | i-$C_4H_9$—S— |
| $C_3H_5$ | $CH_3$ | $CH_3$ | $CH_3$ | 6-$CH_3$ | S | $CH_3$ | s-$C_4H_9$—S— |
| $C_3H_5$ | $CH_3$ | $CH_3$ | $CH_3$ | 6-$CH_3$ | S | $CH_3$ | t-$C_4H_9$—S— |
| $C_3H_5$ | $CH_3$ | $CH_3$ | $CH_3$ | 6-$CH_3$ | S | $CH_3$ | t-$C_4H_9$—$CH_2$—S— |
| $C_6H_{11}$ | $CH_3$ | Cl | Cl | H | S | $CH_3$ | $CH_3$—O— |
| $C_6H_{11}$ | $CH_3$ | Cl | Cl | H | S | $CH_3$ | $C_2H_5$—O— |
| $C_6H_{11}$ | $CH_3$ | Cl | Cl | H | S | $CH_3$ | $C_3H_7$—O— |
| $C_6H_{11}$ | $CH_3$ | Cl | Cl | H | S | $CH_3$ | i-$C_3H_7$—O |
| $C_6H_{11}$ | $CH_3$ | Cl | Cl | H | S | $CH_3$ | i-$C_4H_9$—O |
| $C_6H_{11}$ | $CH_3$ | Cl | Cl | H | S | $CH_3$ | s-$C_4H_9$—O |
| $C_6H_{11}$ | $CH_3$ | Cl | Cl | H | S | $CH_3$ | t-$C_4H_9$—O |
| $C_6H_{11}$ | $CH_3$ | Cl | Cl | H | S | $CH_3$ | t-$C_4H_9$—$CH_2$—O |
| $C_6H_{11}$ | $CH_3$ | Cl | Cl | H | S | $CH_3$ | cyclohexyl-O— |
| $C_6H_{11}$ | $CH_3$ | Cl | Cl | H | S | $CH_3$ | phenyl-O— |
| $C_6H_{11}$ | $CH_3$ | Cl | Cl | H | S | $CH_3$ | benzyl-O— |
| $C_6H_{11}$ | $CH_3$ | Cl | Cl | H | S | $CH_3$ | $CH_3$—S— |
| $C_6H_{11}$ | $CH_3$ | Cl | Cl | H | S | $CH_3$ | $C_2H_5$—S— |
| $C_6H_{11}$ | $CH_3$ | Cl | Cl | H | S | $CH_3$ | $C_3H_7$—S— |
| $C_6H_{11}$ | $CH_3$ | Cl | Cl | H | S | $CH_3$ | i-$C_3H_7$—S— |
| $C_6H_{11}$ | $CH_3$ | Cl | Cl | H | S | $CH_3$ | i-$C_4H_9$—S— |
| $C_6H_{11}$ | $CH_3$ | Cl | Cl | H | S | $CH_3$ | s-$C_4H_9$—S— |
| $C_6H_{11}$ | $CH_3$ | Cl | Cl | H | S | $CH_3$ | t-$C_4H_9$—S— |
| $C_6H_{11}$ | $CH_3$ | Cl | Cl | H | S | $CH_3$ | t-$C_4H_9$—$CH_2$—S— |
| $C_6H_{11}$ | $CH_3$ | $CH_3$ | $CH_3$ | H | S | $CH_3$ | $CH_3$—O— |
| $C_6H_{11}$ | $CH_3$ | $CH_3$ | $CH_3$ | H | S | $CH_3$ | $C_2H_5$—O— |
| $C_6H_{11}$ | $CH_3$ | $CH_3$ | $CH_3$ | H | S | $C_2H_5$ | $C_3H_7$—O— |
| $C_6H_{11}$ | $CH_3$ | $CH_3$ | $CH_3$ | H | S | $CH_3$ | i-$C_3H_7$—O |
| $C_6H_{11}$ | $CH_3$ | $CH_3$ | $CH_3$ | H | S | $CH_3$ | i-$C_4H_9$—O |
| $C_6H_{11}$ | $CH_3$ | $CH_3$ | $CH_3$ | H | S | $CH_3$ | s-$C_4H_9$—O |
| $C_6H_{11}$ | $CH_3$ | $CH_3$ | $CH_3$ | H | S | $CH_3$ | t-$C_4H_9$—O |
| $C_6H_{11}$ | $CH_3$ | $CH_3$ | $CH_3$ | H | S | $CH_3$ | t-$C_4H_9$—$CH_2$—O |
| $C_6H_{11}$ | $CH_3$ | $CH_3$ | $CH_3$ | H | S | $CH_3$ | cyclohexyl-O— |

TABLE 5-continued

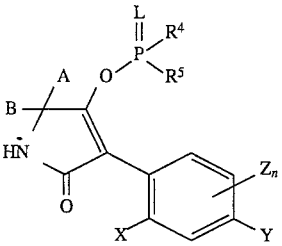
(Ie)

| A* | B | X | Y | $Z_n$ | L | $R^4$ | $R^5$ |
|---|---|---|---|---|---|---|---|
| $C_6H_{11}$ | $CH_3$ | $CH_3$ | $CH_3$ | H | S | $CH_3$ | 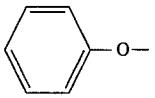 |
| $C_6H_{11}$ | $CH_3$ | $CH_3$ | $CH_3$ | H | S | $CH_3$ | 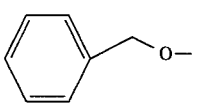 |
| $C_6H_{11}$ | $CH_3$ | $CH_3$ | $CH_3$ | H | S | $CH_3$ | $CH_3-S-$ |
| $C_6H_{11}$ | $CH_3$ | $CH_3$ | $CH_3$ | H | S | $CH_3$ | $C_2H_5-S-$ |
| $C_6H_{11}$ | $CH_3$ | $CH_3$ | $CH_3$ | H | S | $CH_3$ | $C_3H_7-S-$ |
| $C_6H_{11}$ | $CH_3$ | $CH_3$ | $CH_3$ | H | S | $CH_3$ | $i-C_3H_7-S-$ |
| $C_6H_{11}$ | $CH_3$ | $CH_3$ | $CH_3$ | H | S | $CH_3$ | $i-C_4H_9-S-$ |
| $C_6H_{11}$ | $CH_3$ | $CH_3$ | $CH_3$ | H | S | $CH_3$ | $s-C_4H_9-S-$ |
| $C_6H_{11}$ | $CH_3$ | $CH_3$ | $CH_3$ | H | S | $CH_3$ | $t-C_4H_9-S-$ |
| $C_6H_{11}$ | $CH_3$ | $CH_3$ | $CH_3$ | H | S | $CH_3$ | $t-C_4H_9-CH_2-S-$ |
| $C_6H_{11}$ | $CH_3$ | $CH_3$ | $CH_3$ | 6-$CH_3$ | S | $CH_3$ | $CH_3-O-$ |
| $C_6H_{11}$ | $CH_3$ | $CH_3$ | $CH_3$ | 6-$CH_3$ | S | $CH_3$ | $C_2H_5-O-$ |
| $C_6H_{11}$ | $CH_3$ | $CH_3$ | $CH_3$ | 6-$CH_3$ | S | $CH_3$ | $C_3H_7-O-$ |
| $C_6H_{11}$ | $CH_3$ | $CH_3$ | $CH_3$ | 6-$CH_3$ | S | $CH_3$ | $i-C_3H_7-O$ |
| $C_6H_{11}$ | $CH_3$ | $CH_3$ | $CH_3$ | 6-$CH_3$ | S | $CH_3$ | $i-C_4H_9-O$ |
| $C_6H_{11}$ | $CH_3$ | $CH_3$ | $CH_3$ | 6-$CH_3$ | S | $CH_3$ | $s-C_4H_9-O$ |
| $C_6H_{11}$ | $CH_3$ | $CH_3$ | $CH_3$ | 6-$CH_3$ | S | $CH_3$ | $t-C_4H_9-O$ |
| $C_6H_{11}$ | $CH_3$ | $CH_3$ | $CH_3$ | 6-$CH_3$ | S | $CH_3$ | $t-C_4H_9-CH_2-O$ |
| $C_6H_{11}$ | $CH_3$ | $CH_3$ | $CH_3$ | 6-$CH_3$ | S | $CH_3$ | 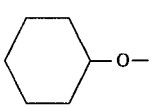 |
| $C_6H_{11}$ | $CH_3$ | $CH_3$ | $CH_3$ | 6-$CH_3$ | S | $CH_3$ | 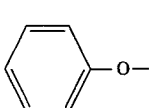 |
| $C_6H_{11}$ | $CH_3$ | $CH_3$ | $CH_3$ | 6-$CH_3$ | S | $CH_3$ | 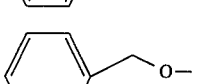 |
| $C_6H_{11}$ | $CH_3$ | $CH_3$ | $CH_3$ | 6-$CH_3$ | S | $CH_3$ | $CH_3-S-$ |
| $C_6H_{11}$ | $CH_3$ | $CH_3$ | $CH_3$ | 6-$CH_3$ | S | $CH_3$ | $C_2H_5-S-$ |
| $C_6H_{11}$ | $CH_3$ | $CH_3$ | $CH_3$ | 6-$CH_3$ | S | $CH_3$ | $C_3H_7-S-$ |
| $C_6H_{11}$ | $CH_3$ | $CH_3$ | $CH_3$ | 6-$CH_3$ | S | $CH_3$ | $i-C_3H_7-S-$ |
| $C_6H_{11}$ | $CH_3$ | $CH_3$ | $CH_3$ | 6-$CH_3$ | S | $CH_3$ | $i-C_4H_9-S-$ |
| $C_6H_{11}$ | $CH_3$ | $CH_3$ | $CH_3$ | 6-$CH_3$ | S | $CH_3$ | $s-C_4H_9-S-$ |
| $C_6H_{11}$ | $CH_3$ | $CH_3$ | $CH_3$ | 6-$CH_3$ | S | $CH_3$ | $t-C_4H_9-S-$ |
| $C_6H_{11}$ | $CH_3$ | $CH_3$ | $CH_3$ | 6-$CH_3$ | S | $CH_3$ | $t-C_4H_9-CH_2-S-$ |
| $C_3H_5$ | $CH_3$ | Cl | Cl | H | S | $O-CH_3$ | $CH_3-O-$ |
| $C_3H_5$ | $CH_3$ | Cl | Cl | H | S | $O-CH_3$ | $C_2H_5-O-$ |
| $C_3H_5$ | $CH_3$ | Cl | Cl | H | S | $O-CH_3$ | $C_3H_7-O-$ |
| $C_3H_5$ | $CH_3$ | Cl | Cl | H | S | $O-CH_3$ | $i-C_3H_7-O$ |
| $C_3H_5$ | $CH_3$ | Cl | Cl | H | S | $O-CH_3$ | $i-C_4H_9-O$ |
| $C_3H_5$ | $CH_3$ | Cl | Cl | H | S | $O-CH_3$ | $s-C_4H_9-O$ |
| $C_3H_5$ | $CH_3$ | Cl | Cl | H | S | $O-CH_3$ | $t-C_4H_9-O$ |
| $C_3H_5$ | $CH_3$ | Cl | Cl | H | S | $O-CH_3$ | $t-C_4H_9-CH_2-O$ |

TABLE 5-continued

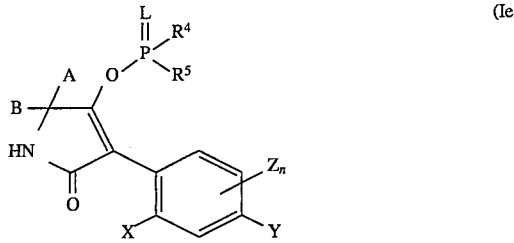

| A* | B | X | Y | $Z_n$ | L | $R^4$ | $R^5$ |
|---|---|---|---|---|---|---|---|
| $C_3H_5$ | $CH_3$ | Cl | Cl | H | S | $O-CH_3$ | 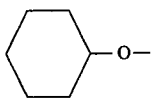 |
| $C_3H_5$ | $CH_3$ | Cl | Cl | H | S | $O-CH_3$ | 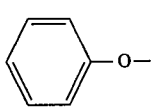 |
| $C_3H_5$ | $CH_3$ | Cl | Cl | H | S | $O-CH_3$ | 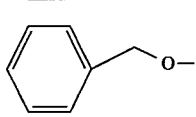 |
| $C_3H_5$ | $CH_3$ | Cl | Cl | H | S | $O-CH_3$ | $CH_3-S-$ |
| $C_3H_5$ | $CH_3$ | Cl | Cl | H | S | $O-CH_3$ | $C_2H_5-S-$ |
| $C_3H_5$ | $CH_3$ | Cl | Cl | H | S | $O-CH_3$ | $C_3H_7-S-$ |
| $C_3H_5$ | $CH_3$ | Cl | Cl | H | S | $O-CH_3$ | $i-C_3H_7-S-$ |
| $C_3H_5$ | $CH_3$ | Cl | Cl | H | S | $O-CH_3$ | $i-C_4H_9-S-$ |
| $C_3H_5$ | $CH_3$ | Cl | Cl | H | S | $O-CH_3$ | $s-C_4H_9-S-$ |
| $C_3H_5$ | $CH_3$ | Cl | Cl | H | S | $O-CH_3$ | $t-C_4H_9-S-$ |
| $C_3H_5$ | $CH_3$ | Cl | Cl | H | S | $O-CH_3$ | $t-C_4H_9-CH_2-S-$ |
| $C_3H_5$ | $CH_3$ | $CH_3$ | $CH_3$ | H | S | $O-CH_3$ | $CH_3-O-$ |
| $C_3H_5$ | $CH_3$ | $CH_3$ | $CH_3$ | H | S | $O-CH_3$ | $C_2H_5-O-$ |
| $C_3H_5$ | $CH_3$ | $CH_3$ | $CH_3$ | H | S | $O-CH_3$ | $C_3H_7-O-$ |
| $C_3H_5$ | $CH_3$ | $CH_3$ | $CH_3$ | H | S | $O-CH_3$ | $i-C_3H_7-O$ |
| $C_3H_5$ | $CH_3$ | $CH_3$ | $CH_3$ | H | S | $O-CH_3$ | $i-C_4H_9-O$ |
| $C_3H_5$ | $CH_3$ | $CH_3$ | $CH_3$ | H | S | $O-CH_3$ | $s-C_4H_9-O$ |
| $C_3H_5$ | $CH_3$ | $CH_3$ | $CH_3$ | H | S | $O-CH_3$ | $t-C_4H_9-O$ |
| $C_3H_5$ | $CH_3$ | $CH_3$ | $CH_3$ | H | S | $O-CH_3$ | $t-C_4H_9-CH_2-O$ |
| $C_3H_5$ | $CH_3$ | $CH_3$ | $CH_3$ | H | S | $O-CH_3$ | 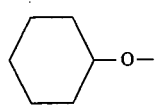 |
| $C_3H_5$ | $CH_3$ | $CH_3$ | $CH_3$ | H | S | $O-CH_3$ | 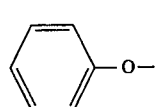 |
| $C_3H_5$ | $CH_3$ | $CH_3$ | $CH_3$ | H | S | $O-CH_3$ | 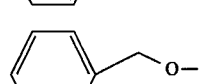 |
| $C_3H_5$ | $CH_3$ | $CH_3$ | $CH_3$ | H | S | $O-CH_3$ | $CH_3-S-$ |
| $C_3H_5$ | $CH_3$ | $CH_3$ | $CH_3$ | H | S | $O-CH_3$ | $C_2H_5-S-$ |
| $C_3H_5$ | $CH_3$ | $CH_3$ | $CH_3$ | H | S | $O-CH_3$ | $C_3H_7-S-$ |
| $C_3H_5$ | $CH_3$ | $CH_3$ | $CH_3$ | H | S | $O-CH_3$ | $i-C_3H_7-S-$ |
| $C_3H_5$ | $CH_3$ | $CH_3$ | $CH_3$ | H | S | $O-CH_3$ | $i-C_4H_9-S-$ |
| $C_3H_5$ | $CH_3$ | $CH_3$ | $CH_3$ | H | S | $O-CH_3$ | $s-C_4H_9-S-$ |
| $C_3H_5$ | $CH_3$ | $CH_3$ | $CH_3$ | H | S | $O-CH_3$ | $t-C_4H_9-S-$ |
| $C_3H_5$ | $CH_3$ | $CH_3$ | $CH_3$ | H | S | $O-CH_3$ | $t-C_4H_9-CH_2-S-$ |
| $C_3H_5$ | $CH_3$ | $CH_3$ | $CH_3$ | $6-CH_3$ | S | $O-CH_3$ | $CH_3-O-$ |
| $C_3H_5$ | $CH_3$ | $CH_3$ | $CH_3$ | $6-CH_3$ | S | $O-CH_3$ | $C_2H_5-O-$ |
| $C_3H_5$ | $CH_3$ | $CH_3$ | $CH_3$ | $6-CH_3$ | S | $O-CH_3$ | $C_3H_7-O-$ |
| $C_3H_5$ | $CH_3$ | $CH_3$ | $CH_3$ | $6-CH_3$ | S | $O-CH_3$ | $i-C_3H_7-O$ |
| $C_3H_5$ | $CH_3$ | $CH_3$ | $CH_3$ | $6-CH_3$ | S | $O-CH_3$ | $i-C_4H_9-O$ |
| $C_3H_5$ | $CH_3$ | $CH_3$ | $CH_3$ | $6-CH_3$ | S | $O-CH_3$ | $s-C_4H_9-O$ |
| $C_3H_5$ | $CH_3$ | $CH_3$ | $CH_3$ | $6-CH_3$ | S | $O-CH_3$ | $t-C_4H_9-O$ |
| $C_3H_5$ | $CH_3$ | $CH_3$ | $CH_3$ | $6-CH_3$ | S | $O-CH_3$ | $t-C_4H_9-CH_2-O$ |

TABLE 5-continued

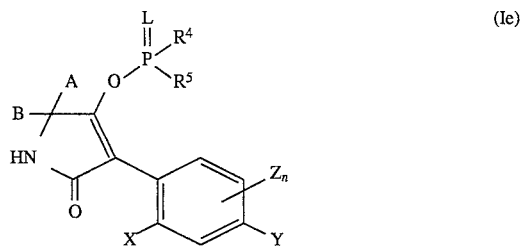
(Ie)

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | 6-$CH_3$ | S | $O-CH_3$ | cyclohexyl-O— |
| $C_3H_5$ | $CH_3$ | $CH_3$ | $CH_3$ | 6-$CH_3$ | S | $O-CH_3$ | phenyl-O— |
| $C_3H_5$ | $CH_3$ | $CH_3$ | $CH_3$ | 6-$CH_3$ | S | $O-CH_3$ | benzyl-O— |
| $C_3H_5$ | $CH_3$ | $CH_3$ | $CH_3$ | 6-$CH_3$ | S | $O-CH_3$ | $CH_3-S-$ |
| $C_3H_5$ | $CH_3$ | $CH_3$ | $CH_3$ | 6-$CH_3$ | S | $O-CH_3$ | $C_2H_5-S-$ |
| $C_3H_5$ | $CH_3$ | $CH_3$ | $CH_3$ | 6-$CH_3$ | S | $O-CH_3$ | $C_3H_7-S-$ |
| $C_3H_5$ | $CH_3$ | $CH_3$ | $CH_3$ | 6-$CH_3$ | S | $O-CH_3$ | i-$C_3H_7-S-$ |
| $C_3H_5$ | $CH_3$ | $CH_3$ | $CH_3$ | 6-$CH_3$ | S | $O-CH_3$ | i-$C_4H_9-S-$ |
| $C_3H_5$ | $CH_3$ | $CH_3$ | $CH_3$ | 6-$CH_3$ | S | $O-CH_3$ | s-$C_4H_9-S-$ |
| $C_3H_5$ | $CH_3$ | $CH_3$ | $CH_3$ | 6-$CH_3$ | S | $O-CH_3$ | t-$C_4H_9-S-$ |
| $C_3H_5$ | $CH_3$ | $CH_3$ | $CH_3$ | 6-$CH_3$ | S | $O-CH_3$ | t-$C_4H_9CH_2-S-$ |
| $C_6H_{11}$ | $CH_3$ | Cl | Cl | H | S | $O-CH_3$ | $CH_3-O-$ |
| $C_6H_{11}$ | $CH_3$ | Cl | Cl | H | S | $O-CH_3$ | $C_2H_5-O-$ |
| $C_6H_{11}$ | $CH_3$ | Cl | Cl | H | S | $O-CH_3$ | $C_3H_7-O-$ |
| $C_6H_{11}$ | $CH_3$ | Cl | Cl | H | S | $O-CH_3$ | i-$C_3H_7-O$ |
| $C_6H_{11}$ | $CH_3$ | Cl | Cl | H | S | $O-CH_3$ | i-$C_4H_9-O$ |
| $C_6H_{11}$ | $CH_3$ | Cl | Cl | H | S | $O-CH_3$ | s-$C_4H_9-O$ |
| $C_6H_{11}$ | $CH_3$ | Cl | Cl | H | S | $O-CH_3$ | t-$C_4H_9-O$ |
| $C_6H_{11}$ | $CH_3$ | Cl | Cl | H | S | $O-CH_3$ | t-$C_4H_9-CH_2-O$ |
| $C_6H_{11}$ | $CH_3$ | Cl | Cl | H | S | $O-CH_3$ | cyclohexyl-O— |
| $C_6H_{11}$ | $CH_3$ | Cl | Cl | H | S | $O-CH_3$ | phenyl-O— |
| $C_6H_{11}$ | $CH_3$ | Cl | Cl | H | S | $O-CH_3$ | benzyl-O— |
| $C_6H_{11}$ | $CH_3$ | Cl | Cl | H | S | $O-CH_3$ | $CH_3-S-$ |
| $C_6H_{11}$ | $CH_3$ | Cl | Cl | H | S | $O-CH_3$ | $C_2H_5-S-$ |
| $C_6H_{11}$ | $CH_3$ | Cl | Cl | H | S | $O-CH_3$ | $C_3H_7-S-$ |
| $C_6H_{11}$ | $CH_3$ | Cl | Cl | H | S | $O-CH_3$ | i-$C_3H_7-S-$ |
| $C_6H_{11}$ | $CH_3$ | Cl | Cl | H | S | $O-CH_3$ | i-$C_4H_9-S-$ |
| $C_6H_{11}$ | $CH_3$ | Cl | Cl | H | S | $O-CH_3$ | s-$C_4H_9-S-$ |
| $C_6H_{11}$ | $CH_3$ | Cl | Cl | H | S | $O-CH_3$ | t-$C_4H_9-S-$ |
| $C_6H_{11}$ | $CH_3$ | Cl | Cl | H | S | $O-CH_3$ | t-$C_4H_9-CH_2-S-$ |
| $C_6H_{11}$ | $CH_3$ | $CH_3$ | $CH_3$ | H | S | $O-CH_3$ | $CH_3-O-$ |
| $C_6H_{11}$ | $CH_3$ | $CH_3$ | $CH_3$ | H | S | $O-CH_3$ | $C_2H_5-O-$ |
| $C_6H_{11}$ | $CH_3$ | $CH_3$ | $CH_3$ | H | S | $O-CH_3$ | $C_3H_7-O-$ |
| $C_6H_{11}$ | $CH_3$ | $CH_3$ | $CH_3$ | H | S | $O-CH_3$ | i-$C_3H_7-O$ |
| $C_6H_{11}$ | $CH_3$ | $CH_3$ | $CH_3$ | H | S | $O-CH_3$ | i-$C_4H_9-O$ |
| $C_6H_{11}$ | $CH_3$ | $CH_3$ | $CH_3$ | H | S | $O-CH_3$ | s-$C_4H_9-O$ |
| $C_6H_{11}$ | $CH_3$ | $CH_3$ | $CH_3$ | H | S | $O-CH_3$ | t-$C_4H_9-O$ |

TABLE 5-continued (Ie)

[Structure: phosphate ester with L=P double bond, R⁴, R⁵ substituents, A and B groups on carbon, HN-C(=O) ring, phenyl with X, Y, Zn substituents]

| A* | B | X | Y | Z_n | L | R⁴ | R⁵ |
|---|---|---|---|---|---|---|---|
| $C_6H_{11}$ | $CH_3$ | $CH_3$ | $CH_3$ | H | S | $O-CH_3$ | $t-C_4H_9-CH_2-O-$ |
| $C_6H_{11}$ | $CH_3$ | $CH_3$ | $CH_3$ | H | S | $O-CH_3$ | cyclohexyl-O− |
| $C_6H_{11}$ | $CH_3$ | $CH_3$ | $CH_3$ | H | S | $O-CH_3$ | phenyl-O− |
| $C_6H_{11}$ | $CH_3$ | $CH_3$ | $CH_3$ | H | S | $O-CH_3$ | benzyl-O− |
| $C_6H_{11}$ | $CH_3$ | $CH_3$ | $CH_3$ | H | S | $O-CH_3$ | $CH_3-S-$ |
| $C_6H_{11}$ | $CH_3$ | $CH_3$ | $CH_3$ | H | S | $O-CH_3$ | $C_2H_5-S-$ |
| $C_6H_{11}$ | $CH_3$ | $CH_3$ | $CH_3$ | H | S | $O-CH_3$ | $C_3H_7-S-$ |
| $C_6H_{11}$ | $CH_3$ | $CH_3$ | $CH_3$ | H | S | $O-CH_3$ | $i-C_3H_7-S-$ |
| $C_6H_{11}$ | $CH_3$ | $CH_3$ | $CH_3$ | H | S | $O-CH_3$ | $i-C_4H_9-S-$ |
| $C_6H_{11}$ | $CH_3$ | $CH_3$ | $CH_3$ | H | S | $O-CH_3$ | $s-C_4H_9-S-$ |
| $C_6H_{11}$ | $CH_3$ | $CH_3$ | $CH_3$ | H | S | $O-CH_3$ | $t-C_4H_9-S-$ |
| $C_6H_{11}$ | $CH_3$ | $CH_3$ | $CH_3$ | H | S | $O-CH_3$ | $t-C_4H_9-CH_2-S-$ |
| $C_6H_{11}$ | $CH_3$ | $CH_3$ | $CH_3$ | 6-$CH_3$ | S | $O-CH_3$ | $CH_3-O-$ |
| $C_6H_{11}$ | $CH_3$ | $CH_3$ | $CH_3$ | 6-$CH_3$ | S | $O-CH_3$ | $C_2H_5-O-$ |
| $C_6H_{11}$ | $CH_3$ | $CH_3$ | $CH_3$ | 6-$CH_3$ | S | $O-CH_3$ | $C_3H_7-O-$ |
| $C_6H_{11}$ | $CH_3$ | $CH_3$ | $CH_3$ | 6-$CH_3$ | S | $O-CH_3$ | $i-C_3H_7-O$ |
| $C_6H_{11}$ | $CH_3$ | $CH_3$ | $CH_3$ | 6-$CH_3$ | S | $O-CH_3$ | $i-C_4H_9-O$ |
| $C_6H_{11}$ | $CH_3$ | $CH_3$ | $CH_3$ | 6-$CH_3$ | S | $O-CH_3$ | $s-C_4H_9-O$ |
| $C_6H_{11}$ | $CH_3$ | $CH_3$ | $CH_3$ | 6-$CH_3$ | S | $O-CH_3$ | $t-C_4H_9-O$ |
| $C_6H_{11}$ | $CH_3$ | $CH_3$ | $CH_3$ | 6-$CH_3$ | S | $O-CH_3$ | $t-C_4H_9-CH_2-O$ |
| $C_6H_{11}$ | $CH_3$ | $CH_3$ | $CH_3$ | 6-$CH_3$ | S | $O-CH_3$ | cyclohexyl-O− |
| $C_6H_{11}$ | $CH_3$ | $CH_3$ | $CH_3$ | 6-$CH_3$ | S | $O-CH_3$ | phenyl-O− |
| $C_6H_{11}$ | $CH_3$ | $CH_3$ | $CH_3$ | 6-$CH_3$ | S | $O-CH_3$ | benzyl-O− |
| $C_6H_{11}$ | $CH_3$ | $CH_3$ | $CH_3$ | 6-$CH_3$ | S | $O-CH_3$ | $CH_3-S-$ |
| $C_6H_{11}$ | $CH_3$ | $CH_3$ | $CH_3$ | 6-$CH_3$ | S | $O-CH_3$ | $C_2H_5-S-$ |
| $C_6H_{11}$ | $CH_3$ | $CH_3$ | $CH_3$ | 6-$CH_3$ | S | $O-CH_3$ | $C_3H_7-S-$ |
| $C_6H_{11}$ | $CH_3$ | $CH_3$ | $CH_3$ | 6-$CH_3$ | S | $O-CH_3$ | $i-C_3H_7-S-$ |
| $C_6H_{11}$ | $CH_3$ | $CH_3$ | $CH_3$ | 6-$CH_3$ | S | $O-CH_3$ | $i-C_4H_9-S-$ |
| $C_6H_{11}$ | $CH_3$ | $CH_3$ | $CH_3$ | 6-$CH_3$ | S | $O-CH_3$ | $s-C_4H_9-S-$ |
| $C_6H_{11}$ | $CH_3$ | $CH_3$ | $CH_3$ | 6-$CH_3$ | S | $O-CH_3$ | $t-C_4H_9-S-$ |
| $C_6H_{11}$ | $CH_3$ | $CH_3$ | $CH_3$ | 6-$CH_3$ | S | $O-CH_3$ | $t-C_4H_9CH_2-S-$ |
| $C_3H_5$ | $CH_3$ | Cl | Cl | H | S | $O-C_2H_5$ | $CH_3-O-$ |
| $C_3H_5$ | $CH_3$ | Cl | Cl | H | S | $O-C_2H_5$ | $C_2H_5-O-$ |
| $C_3H_5$ | $CH_3$ | Cl | Cl | H | S | $O-C_2H_5$ | $C_3H_7-O-$ |
| $C_3H_5$ | $CH_3$ | Cl | Cl | H | S | $O-C_2H_5$ | $i-C_3H_7-O$ |
| $C_3H_5$ | $CH_3$ | Cl | Cl | H | S | $O-C_2H_5$ | $i-C_4H_9-O$ |
| $C_3H_5$ | $CH_3$ | Cl | Cl | H | S | $O-C_2H_5$ | $s-C_4H_9-O$ |

TABLE 5-continued

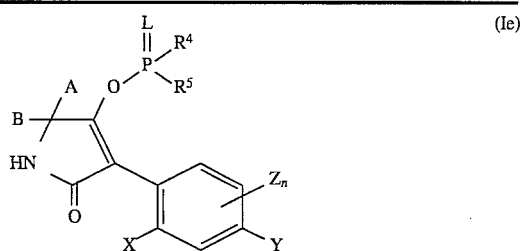

(Ie)

| A* | B | X | Y | $Z_n$ | L | $R^4$ | $R^5$ |
|---|---|---|---|---|---|---|---|
| $C_3H_5$ | $CH_3$ | Cl | Cl | H | S | $O-C_2H_5$ | $t-C_4H_9-O$ |
| $C_3H_5$ | $CH_3$ | Cl | Cl | H | S | $O-C_2H_5$ | $i-C_4H_9-CH_2-O$ |
| $C_3H_5$ | $CH_3$ | Cl | Cl | H | S | $O-C_2H_5$ | cyclohexyl-O— |
| $C_3H_5$ | $CH_3$ | Cl | Cl | H | S | $O-C_2H_5$ | phenyl-O— |
| $C_3H_5$ | $CH_3$ | Cl | Cl | H | S | $O-C_2H_5$ | benzyl-O— |
| $C_3H_5$ | $CH_3$ | Cl | Cl | H | S | $O-C_2H_5$ | $CH_3-S-$ |
| $C_3H_5$ | $CH_3$ | Cl | Cl | H | S | $O-C_2H_5$ | $C_2H_5-S-$ |
| $C_3H_5$ | $CH_3$ | Cl | Cl | H | S | $O-C_2H_5$ | $C_3H_7-S-$ |
| $C_3H_5$ | $CH_3$ | Cl | Cl | H | S | $O-C_2H_5$ | $i-C_3H_7-S-$ |
| $C_3H_5$ | $CH_3$ | Cl | Cl | H | S | $O-C_2H_5$ | $i-C_4H_9-S-$ |
| $C_3H_5$ | $CH_3$ | Cl | Cl | H | S | $O-C_2H_5$ | $s-C_4H_9-S-$ |
| $C_3H_5$ | $CH_3$ | Cl | Cl | H | S | $O-C_2H_5$ | $t-C_4H_9-S-$ |
| $C_3H_5$ | $CH_3$ | Cl | Cl | H | S | $O-C_2H_5$ | $t-C_4H_9-CH_2-S-$ |
| $C_3H_5$ | $CH_3$ | $CH_3$ | $CH_3$ | H | S | $O-C_2H_5$ | $CH_3-O-$ |
| $C_3H_5$ | $CH_3$ | $CH_3$ | $CH_3$ | H | S | $O-C_2H_5$ | $C_2H_5-O-$ |
| $C_3H_5$ | $CH_3$ | $CH_3$ | $CH_3$ | H | S | $O-C_2H_5$ | $C_3H_7-O-$ |
| $C_3H_5$ | $CH_3$ | $CH_3$ | $CH_3$ | H | S | $O-C_2H_5$ | $i-C_3H_7-O$ |
| $C_3H_5$ | $CH_3$ | $CH_3$ | $CH_3$ | H | S | $O-C_2H_5$ | $i-C_4H_9-O$ |
| $C_3H_5$ | $CH_3$ | $CH_3$ | $CH_3$ | H | S | $O-C_2H_5$ | $s-C_4H_9-O$ |
| $C_3H_5$ | $CH_3$ | $CH_3$ | $CH_3$ | H | S | $O-C_2H_5$ | $t-C_4H_9-O$ |
| $C_3H_5$ | $CH_3$ | $CH_3$ | $CH_3$ | H | S | $O-C_2H_5$ | $t-C_4H_9-CH_2-O$ |
| $C_3H_5$ | $CH_3$ | $CH_3$ | $CH_3$ | H | S | $O-C_2H_5$ | cyclohexyl-O— |
| $C_3H_5$ | $CH_3$ | $CH_3$ | $CH_3$ | H | S | $O-C_2H_5$ | phenyl-O— |
| $C_3H_5$ | $CH_3$ | $CH_3$ | $CH_3$ | H | S | $O-C_2H_5$ | benzyl-O— |
| $C_3H_5$ | $CH_3$ | $CH_3$ | $CH_3$ | H | S | $O-C_2H_5$ | $CH_3-S-$ |
| $C_3H_5$ | $CH_3$ | $CH_3$ | $CH_3$ | H | S | $O-C_2H_5$ | $C_2H_5-S-$ |
| $C_3H_5$ | $CH_3$ | $CH_3$ | $CH_3$ | H | S | $O-C_2H_5$ | $C_3H_7-S-$ |
| $C_3H_5$ | $CH_3$ | $CH_3$ | $CH_3$ | H | S | $O-C_2H_5$ | $i-C_3H_7-S-$ |
| $C_3H_5$ | $CH_3$ | $CH_3$ | $CH_3$ | H | S | $O-C_2H_5$ | $i-C_4H_9-S-$ |
| $C_3H_5$ | $CH_3$ | $CH_3$ | $CH_3$ | H | S | $O-C_2H_5$ | $s-C_4H_9-S-$ |
| $C_3H_5$ | $CH_3$ | $CH_3$ | $CH_3$ | H | S | $O-C_2H_5$ | $t-C_4H_9-S-$ |
| $C_3H_5$ | $CH_3$ | $CH_3$ | $CH_3$ | H | S | $O-C_2H_5$ | $t-C_4H_9-CH_2-S-$ |
| $C_3H_5$ | $CH_3$ | $CH_3$ | $CH_3$ | $6-CH_3$ | S | $O-C_2H_5$ | $CH_3-O-$ |
| $C_3H_5$ | $CH_3$ | $CH_3$ | $CH_3$ | $6-CH_3$ | S | $O-C_2H_5$ | $C_2H_5-O-$ |
| $C_3H_5$ | $CH_3$ | $CH_3$ | $CH_3$ | $6-CH_3$ | S | $O-C_2H_5$ | $C_3H_7-O-$ |
| $C_3H_5$ | $CH_3$ | $CH_3$ | $CH_3$ | $6-CH_3$ | S | $O-C_2H_5$ | $i-C_3H_7-O$ |
| $C_3H_5$ | $CH_3$ | $CH_3$ | $CH_3$ | $6-CH_3$ | S | $O-C_2H_5$ | $i-C_4H_9-O$ |

TABLE 5-continued

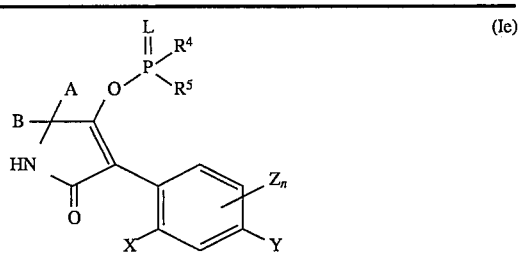

(Ie)

| A* | B | X | Y | $Z_n$ | L | $R^4$ | $R^5$ |
|---|---|---|---|---|---|---|---|
| $C_3H_5$ | $CH_3$ | $CH_3$ | $CH_3$ | 6-$CH_3$ | S | O—$C_2H_5$ | s-$C_4H_9$—O |
| $C_3H_5$ | $CH_3$ | $CH_3$ | $CH_3$ | 6-$CH_3$ | S | O—$C_2H_5$ | t-$C_4H_9$—O |
| $C_3H_5$ | $CH_3$ | $CH_3$ | $CH_3$ | 6-$CH_3$ | S | O—$C_2H_5$ | t-$C_4H_9$—$CH_2$—O |
| $C_3H_5$ | $CH_3$ | $CH_3$ | $CH_3$ | 6-$CH_3$ | S | O—$C_2H_5$ | cyclohexyl-O— |
| $C_3H_5$ | $CH_3$ | $CH_3$ | $CH_3$ | 6-$CH_3$ | S | O—$C_2H_5$ | phenyl-O— |
| $C_3H_5$ | $CH_3$ | $CH_3$ | $CH_3$ | 6-$CH_3$ | S | O—$C_2H_5$ | benzyl-O— |
| $C_3H_5$ | $CH_3$ | $CH_3$ | $CH_3$ | 6-$CH_3$ | S | O—$C_2H_5$ | $CH_3$—S— |
| $C_3H_5$ | $CH_3$ | $CH_3$ | $CH_3$ | 6-$CH_3$ | S | O—$C_2H_5$ | $C_2H_5$—S— |
| $C_3H_5$ | $CH_3$ | $CH_3$ | $CH_3$ | 6-$CH_3$ | S | O—$C_2H_5$ | $C_3H_7$—S— |
| $C_3H_5$ | $CH_3$ | $CH_3$ | $CH_3$ | 6-$CH_3$ | S | O—$C_2H_5$ | i-$C_3H_7$—S— |
| $C_3H_5$ | $CH_3$ | $CH_3$ | $CH_3$ | 6-$CH_3$ | S | O—$C_2H_5$ | i-$C_4H_9$—S— |
| $C_3H_5$ | $CH_3$ | $CH_3$ | $CH_3$ | 6-$CH_3$ | S | O—$C_2H_5$ | s-$C_4H_9$—S— |
| $C_3H_5$ | $CH_3$ | $CH_3$ | $CH_3$ | 6-$CH_3$ | S | O—$C_2H_5$ | t-$C_4H_9$—S— |
| $C_3H_5$ | $CH_3$ | $CH_3$ | $CH_3$ | 6-$CH_3$ | S | O—$C_2H_5$ | t-$C_4H_9$—$CH_2$—S— |
| $C_6H_{11}$ | $CH_3$ | Cl | Cl | H | S | O—$C_2H_5$ | $CH_3$—O— |
| $C_6H_{11}$ | $CH_3$ | Cl | Cl | H | S | O—$C_2H_5$ | $C_2H_5$—O— |
| $C_6H_{11}$ | $CH_3$ | Cl | Cl | H | S | O—$C_2H_5$ | $C_3H_7$—O— |
| $C_6H_{11}$ | $CH_3$ | Cl | Cl | H | S | O—$C_2H_5$ | i-$C_3H_7$—O |
| $C_6H_{11}$ | $CH_3$ | Cl | Cl | H | S | O—$C_2H_5$ | i-$C_4H_9$—O |
| $C_6H_{11}$ | $CH_3$ | Cl | Cl | H | S | O—$C_2H_5$ | s-$C_4H_9$—O |
| $C_6H_{11}$ | $CH_3$ | Cl | Cl | H | S | O—$C_2H_5$ | t-$C_4H_9$—O |
| $C_6H_{11}$ | $CH_3$ | Cl | Cl | H | S | O—$C_2H_5$ | t-$C_4H_9$—$CH_2$—O |
| $C_6H_{11}$ | $CH_3$ | Cl | Cl | H | S | O—$C_2H_5$ | cyclohexyl-O— |
| $C_6H_{11}$ | $CH_3$ | Cl | Cl | H | S | O—$C_2H_5$ | phenyl-O— |
| $C_6H_{11}$ | $CH_3$ | Cl | Cl | H | S | O—$C_2H_5$ | benzyl-O— |
| $C_6H_{11}$ | $CH_3$ | Cl | Cl | H | S | O—$C_2H_5$ | $CH_3$—S— |
| $C_6H_{11}$ | $CH_3$ | Cl | Cl | H | S | O—$C_2H_5$ | $C_2H_5$—S— |
| $C_6H_{11}$ | $CH_3$ | Cl | Cl | H | S | O—$C_2H_5$ | $C_3H_7$—S— |
| $C_6H_{11}$ | $CH_3$ | Cl | Cl | H | S | O—$C_2H_5$ | i-$C_3H_7$—S— |
| $C_6H_{11}$ | $CH_3$ | Cl | Cl | H | S | O—$C_2H_5$ | i-$C_4H_9$—S— |
| $C_6H_{11}$ | $CH_3$ | Cl | Cl | H | S | O—$C_2H_5$ | s-$C_4H_9$—S— |
| $C_6H_{11}$ | $CH_3$ | Cl | Cl | H | S | O—$C_2H_5$ | t-$C_4H_9$—S— |
| $C_6H_{11}$ | $CH_3$ | Cl | Cl | H | S | O—$C_2H_5$ | t-$C_4H_9$—$CH_2$—S— |
| $C_6H_{11}$ | $CH_3$ | $CH_3$ | $CH_3$ | H | S | O—$C_2H_5$ | $CH_3$—O— |
| $C_6H_{11}$ | $CH_3$ | $CH_3$ | $CH_3$ | H | S | O—$C_2H_5$ | $C_2H_5$—O— |
| $C_6H_{11}$ | $CH_3$ | $CH_3$ | $CH_3$ | H | S | O—$C_2H_5$ | $C_3H_7$—O— |
| $C_6H_{11}$ | $CH_3$ | $CH_3$ | $CH_3$ | H | S | O—$C_2H_5$ | i-$C_3H_7$—O |

TABLE 5-continued (Ie)

| A* | B | X | Y | $Z_n$ | L | $R^4$ | $R^5$ |
|---|---|---|---|---|---|---|---|
| $C_6H_{11}$ | $CH_3$ | $CH_3$ | $CH_3$ | H | S | $O-C_2H_5$ | $i-C_4H_9-O$ |
| $C_6H_{11}$ | $CH_3$ | $CH_3$ | $CH_3$ | H | S | $O-C_2H_5$ | $s-C_4H_9-O$ |
| $C_6H_{11}$ | $CH_3$ | $CH_3$ | $CH_3$ | H | S | $O-C_2H_5$ | $t-C_4H_9-O$ |
| $C_6H_{11}$ | $CH_3$ | $CH_3$ | $CH_3$ | H | S | $O-C_2H_5$ | $t-C_4H_9-CH_2-O$ |
| $C_6H_{11}$ | $CH_3$ | $CH_3$ | $CH_3$ | H | S | $O-C_2H_5$ | cyclohexyl-O— |
| $C_6H_{11}$ | $CH_3$ | $CH_3$ | $CH_3$ | H | S | $O-C_2H_5$ | phenyl-O— |
| $C_6H_{11}$ | $CH_3$ | $CH_3$ | $CH_3$ | H | S | $O-C_2H_5$ | benzyl-O— |
| $C_6H_{11}$ | $CH_3$ | $CH_3$ | $CH_3$ | H | S | $O-C_2H_5$ | $CH_3-S-$ |
| $C_6H_{11}$ | $CH_3$ | $CH_3$ | $CH_3$ | H | S | $O-C_2H_5$ | $C_2H_5-S-$ |
| $C_6H_{11}$ | $CH_3$ | $CH_3$ | $CH_3$ | H | S | $O-C_2H_5$ | $C_3H_7-S-$ |
| $C_6H_{11}$ | $CH_3$ | $CH_3$ | $CH_3$ | H | S | $O-C_2H_5$ | $i-C_3H_7-S-$ |
| $C_6H_{11}$ | $CH_3$ | $CH_3$ | $CH_3$ | H | S | $O-C_2H_5$ | $i-C_4H_9-S-$ |
| $C_6H_{11}$ | $CH_3$ | $CH_3$ | $CH_3$ | H | S | $O-C_2H_5$ | $s-C_4H_9-S-$ |
| $C_6H_{11}$ | $CH_3$ | $CH_3$ | $CH_3$ | H | S | $O-C_2H_5$ | $t-C_4H_9-S-$ |
| $C_6H_{11}$ | $CH_3$ | $CH_3$ | $CH_3$ | H | S | $O-C_2H_5$ | $t-C_4H_9-CH_2-S-$ |
| $C_6H_{11}$ | $CH_3$ | $CH_3$ | $CH_3$ | $6-CH_3$ | S | $O-C_2H_5$ | $CH_3-O-$ |
| $C_6H_{11}$ | $CH_3$ | $CH_3$ | $CH_3$ | $6-CH_3$ | S | $O-C_2H_5$ | $C_2H_5-O-$ |
| $C_6H_{11}$ | $CH_3$ | $CH_3$ | $CH_3$ | $6-CH_3$ | S | $O-C_2H_5$ | $C_3H_7-O-$ |
| $C_6H_{11}$ | $CH_3$ | $CH_3$ | $CH_3$ | $6-CH_3$ | S | $O-C_2H_5$ | $i-C_3H_7-O$ |
| $C_6H_{11}$ | $CH_3$ | $CH_3$ | $CH_3$ | $6-CH_3$ | S | $O-C_2H_5$ | $i-C_4H_9-O$ |
| $C_6H_{11}$ | $CH_3$ | $CH_3$ | $CH_3$ | $6-CH_3$ | S | $O-C_2H_5$ | $s-C_4H_9-O$ |
| $C_6H_{11}$ | $CH_3$ | $CH_3$ | $CH_3$ | $6-CH_3$ | S | $O-C_2H_5$ | $t-C_4H_9-O$ |
| $C_6H_{11}$ | $CH_3$ | $CH_3$ | $CH_3$ | $6-CH_3$ | S | $O-C_2H_5$ | $t-C_4H_9-CH_2-O$ |
| $C_6H_{11}$ | $CH_3$ | $CH_3$ | $CH_3$ | $6-CH_3$ | S | $O-C_2H_5$ | cyclohexyl-O— |
| $C_6H_{11}$ | $CH_3$ | $CH_3$ | $CH_3$ | $6-CH_3$ | S | $O-C_2H_5$ | phenyl-O— |
| $C_6H_{11}$ | $CH_3$ | $CH_3$ | $CH_3$ | $6-CH_3$ | S | $O-C_2H_5$ | benzyl-O— |
| $C_6H_{11}$ | $CH_3$ | $CH_3$ | $CH_3$ | $6-CH_3$ | S | $O-C_2H_5$ | $CH_3-S-$ |
| $C_6H_{11}$ | $CH_3$ | $CH_3$ | $CH_3$ | $6-CH_3$ | S | $O-C_2H_5$ | $C_2H_5-S-$ |
| $C_6H_{11}$ | $CH_3$ | $CH_3$ | $CH_3$ | $6-CH_3$ | S | $O-C_2H_5$ | $C_3H_7-S-$ |
| $C_6H_{11}$ | $CH_3$ | $CH_3$ | $CH_3$ | $6-CH_3$ | S | $O-C_2H_5$ | $i-C_3H_7-S-$ |
| $C_6H_{11}$ | $CH_3$ | $CH_3$ | $CH_3$ | $6-CH_3$ | S | $O-C_2H_5$ | $i-C_4H_9-S-$ |
| $C_6H_{11}$ | $CH_3$ | $CH_3$ | $CH_3$ | $6-CH_3$ | S | $O-C_2H_5$ | $s-C_4H_9-S-$ |
| $C_6H_{11}$ | $CH_3$ | $CH_3$ | $CH_3$ | $6-CH_3$ | S | $O-C_2H_5$ | $t-C_4H_9-S-$ |
| $C_6H_{11}$ | $CH_3$ | $CH_3$ | $CH_3$ | $6-CH_3$ | S | $O-C_2H_5$ | $t-C_4H_9-CH_2-S-$ |

A* =

TABLE 5-continued (Ie)

| A* | B | X | Y | $Z_n$ | L | $R^4$ | $R^5$ |
|----|---|---|---|-------|---|-------|-------|

$C_3H_5 = $ —◁ (cyclopropyl)

$C_5H_9 = $ —⬠ (cyclopentyl)

$C_6H_{11} = $ —⬡ (cyclohexyl)

The following compounds of the formula (If) may be mentioned individually in addition to the compounds mentioned in the Preparation Examples:

TABLE 6

(If)

| X | Y | $Z_n$ | A* | B | E |
|---|---|-------|-----|---|---|
| Cl | Cl | H | $C_3H_5$ | $CH_3$ | Na |
| Cl | H | 6-Cl | $C_3H_5$ | $CH_3$ | Na |
| Cl | H | 6-F | $C_3H_5$ | $CH_3$ | Na |
| $CH_3$ | $CH_3$ | H | $C_3H_5$ | $CH_3$ | Na |
| $CH_3$ | $CH_3$ | 6-$CH_3$ | $C_3H_5$ | $CH_3$ | Na |
| Cl | Cl | H | $C_5H_9$ | $CH_3$ | Na |
| Cl | H | 6-Cl | $C_5H_9$ | $CH_3$ | Na |
| Cl | H | 6-F | $C_5H_9$ | $CH_3$ | Na |
| $CH_3$ | $CH_3$ | H | $C_5H_9$ | $CH_3$ | Na |
| $CH_3$ | $CH_3$ | 6-$CH_3$ | $C_5H_9$ | $CH_3$ | Na |
| Cl | Cl | H | $C_6H_{11}$ | $CH_3$ | Na |
| Cl | H | 6-Cl | $C_6H_{11}$ | $CH_3$ | Na |
| Cl | H | 6-F | $C_6H_{11}$ | $CH_3$ | Na |
| $CH_3$ | $CH_3$ | H | $C_6H_{11}$ | $CH_3$ | Na |
| $CH_3$ | $CH_3$ | 6-$CH_3$ | $C_6H_{11}$ | $CH_3$ | Na |
| Cl | Cl | H | $C_3H_5$ | $CH_3$ | $(CH_3)_2CHNH_3$ |
| Cl | H | 6-Cl | $C_3H_5$ | $CH_3$ | $(CH_3)_2CHNH_3$ |
| Cl | H | 6-F | $C_3H_5$ | $CH_3$ | $(CH_3)_2CHNH_3$ |
| $CH_3$ | $CH_3$ | H | $C_3H_5$ | $CH_3$ | $(CH_3)_2CHNH_3$ |
| $CH_3$ | $CH_3$ | 6-$CH_3$ | $C_3H_5$ | $CH_3$ | $(CH_3)_2CHNH_3$ |
| Cl | Cl | H | $C_5H_9$ | $CH_3$ | $(CH_3)_2CHNH_3$ |
| Cl | H | 6-Cl | $C_5H_9$ | $CH_3$ | $(CH_3)_2CHNH_3$ |
| Cl | H | 6-F | $C_5H_9$ | $CH_3$ | $(CH_3)_2CHNH_3$ |
| $CH_3$ | $CH_3$ | H | $C_5H_9$ | $CH_3$ | $(CH_3)_2CHNH_3$ |
| $CH_3$ | $CH_3$ | 6-$CH_3$ | $C_5H_9$ | $CH_3$ | $(CH_3)_2CHNH_3$ |
| Cl | Cl | H | $C_6H_{11}$ | $CH_3$ | $(CH_3)_2CHNH_3$ |
| Cl | H | 6-Cl | $C_6H_{11}$ | $CH_3$ | $(CH_3)_2CHNH_3$ |
| Cl | H | 6-F | $C_6H_{11}$ | $CH_3$ | $(CH_3)_2CHNH_3$ |
| $CH_3$ | $CH_3$ | H | $C_6H_{11}$ | $CH_3$ | $(CH_3)_2CHNH_3$ |
| $CH_3$ | $CH_3$ | 6-$CH_3$ | $C_6H_{11}$ | $CH_3$ | $(CH_3)_2CHNH_3$ |

TABLE 6-continued (If)

| X | Y | $Z_n$ | A* | B | E |
|---|---|-------|-----|---|---|

$A* = C_3H_5 = $ —◁  $C_5H_9 = $ —⬠  $C_6H_{11} = $ —⬡

The following compounds of the formula (Ig) may be mentioned individually in addition to the compounds mentioned in the preparation Examples:

TABLE 7

(Ig)

| X | Y | $Z_n$ | A* | B | $R^6$ | $R^7$ |
|---|---|-------|-----|---|-------|-------|
| Cl | Cl | H | $C_3H_5$ | $CH_3$ | $CH_3$ | $CH_3$ |
| Cl | H | 6-Cl | $C_3H_5$ | $CH_3$ | $CH_3$ | $CH_3$ |
| Cl | H | 6-F | $C_3H_5$ | $CH_3$ | $CH_3$ | $CH_3$ |
| $CH_3$ | $CH_3$ | H | $C_3H_5$ | $CH_3$ | $CH_3$ | $CH_3$ |
| $CH_3$ | $CH_3$ | 6-$CH_3$ | $C_3H_5$ | $CH_3$ | $CH_3$ | $CH_3$ |
| Cl | Cl | H | $C_5H_9$ | $CH_3$ | $CH_3$ | $CH_3$ |

TABLE 7-continued

| X | Y | $Z_n$ | A* | B | $R^6$ | $R^7$ |
|---|---|---|---|---|---|---|
| Cl | H | 6-Cl | $C_5H_9$ | $CH_3$ | $CH_3$ | $CH_3$ |
| Cl | H | 6-F | $C_5H_9$ | $CH_3$ | $CH_3$ | $CH_3$ |
| $CH_3$ | $CH_3$ | H | $C_5H_9$ | $CH_3$ | $CH_3$ | $CH_3$ |
| $CH_3$ | $CH_3$ | 6-$CH_3$ | $C_5H_9$ | $CH_3$ | $CH_3$ | $CH_3$ |
| Cl | Cl | H | $C_6H_{11}$ | $CH_3$ | $CH_3$ | $CH_3$ |
| Cl | H | 6-Cl | $C_6H_{11}$ | $CH_3$ | $CH_3$ | $CH_3$ |
| Cl | H | 6-F | $C_6H_{11}$ | $CH_3$ | $CH_3$ | $CH_3$ |
| $CH_3$ | $CH_3$ | H | $C_6H_{11}$ | $CH_3$ | $CH_3$ | $CH_3$ |
| $CH_3$ | $CH_3$ | 6-$CH_3$ | $C_6H_{11}$ | $CH_3$ | $CH_3$ | $CH_3$ |
| Cl | Cl | H | $C_3H_5$ | $CH_3$ | $-(CH_2)_2-O-(CH_2)_2-$ | |
| Cl | H | 6-Cl | $C_3H_5$ | $CH_3$ | $-(CH_2)_2-O-(CH_2)_2-$ | |
| Cl | H | 6-F | $C_3H_5$ | $CH_3$ | $-(CH_2)_2-O-(CH_2)_2-$ | |
| $CH_3$ | $CH_3$ | H | $C_3H_5$ | $CH_3$ | $-(CH_2)_2-O-(CH_2)_2-$ | |
| $CH_3$ | $CH_3$ | 6-$CH_3$ | $C_3H_5$ | $CH_3$ | $-(CH_2)_2-O-(CH_2)_2-$ | |
| Cl | Cl | H | $C_5H_9$ | $CH_3$ | $-(CH_2)_2-O-(CH_2)_2-$ | |
| Cl | H | 6-Cl | $C_5H_9$ | $CH_3$ | $-(CH_2)_2-O-(CH_2)_2-$ | |
| Cl | H | 6-F | $C_5H_9$ | $CH_3$ | $-(CH_2)_2-O-(CH_2)_2-$ | |
| $CH_3$ | $CH_3$ | H | $C_5H_9$ | $CH_3$ | $-(CH_2)_2-O-(CH_2)_2-$ | |
| $CH_3$ | $CH_3$ | 6-$CH_3$ | $C_5H_9$ | $CH_3$ | $-(CH_2)_2-O-(CH_2)_2-$ | |
| Cl | Cl | H | $C_6H_{11}$ | $CH_3$ | $-(CH_2)_2-O-(CH_2)_2-$ | |
| Cl | H | 6-Cl | $C_6H_{11}$ | $CH_3$ | $-(CH_2)_2-O-(CH_2)_2-$ | |
| Cl | H | 6-F | $C_6H_{11}$ | $CH_3$ | $-(CH_2)_2-O-(CH_2)_2-$ | |
| $CH_3$ | $CH_3$ | H | $C_6H_{11}$ | $CH_3$ | $-(CH_2)_2-O-(CH_2)_2-$ | |
| $CH_3$ | $CH_3$ | 6-$CH_3$ | $C_6H_{11}$ | $CH_3$ | $-(CH_2)_2-O-(CH_2)_2-$ | |

If, according to process (A) N-2,4-dichlorophenylacetyl-2-cyclohexylalanine ethyl ester is used, the course of the process according to the invention can be represented by the following equation:

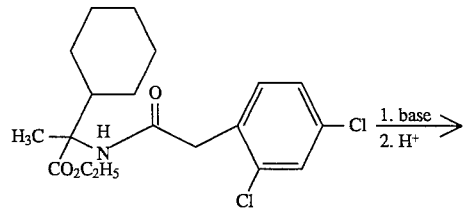

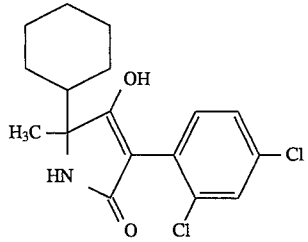

If, according to process (B) (variant α), 3-(2,4,6-trimethylphenyl)-5-cyclopropyl-5-methyl-pyrrolidine-2,4-dione and pivaloyl chloride are used as starting substances, the course of the process according to the invention can be represented by the following equation:

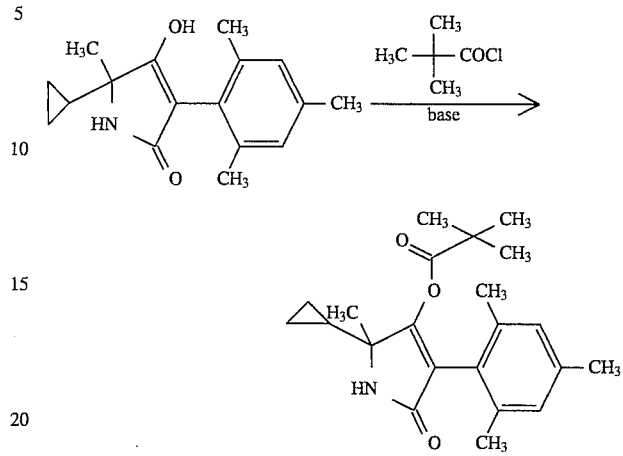

If, according to process B (variant β), 3-(2,4,6-trimethylphenyl)-5-cyclopentyl-5-ethyl-pyrrolidine-2,4-dione and acetic anhydride are used as starting compounds, the course of the process according to the invention can be represented by the following equation:

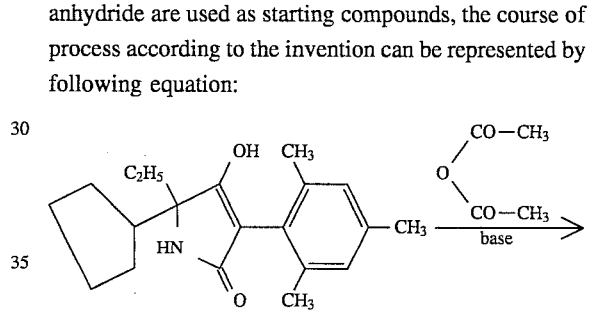

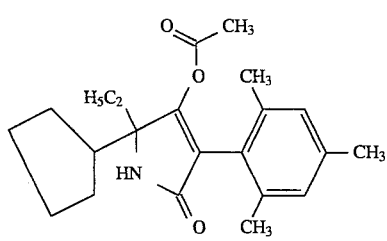

If, according to process (C), 3-(2,4,6-trimethylphenyl)-5-[(4-methyl)-cyclohexyl]-5-methyl-pyrrolidine-2,4-dione and ethoxyethyl chloroformate are used as starting compounds, the course of the process according to the invention can be represented by the following equation.

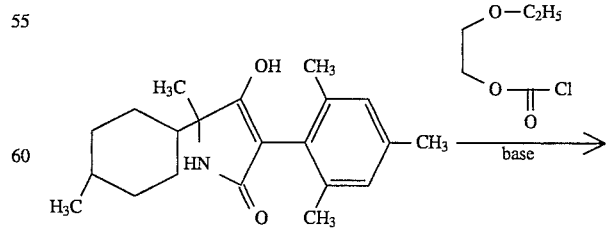

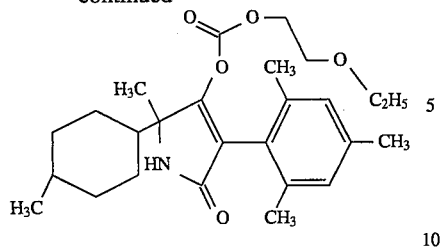

If, according to process ($D_\alpha$), 3-(2,4,6-trimethylphenyl)-5-cyclopentyl-5-methyl-pyrrolidine-2,4-dione and methyl chloromonothioformate are used as starting materials, the course of the reaction can be represented as follows:

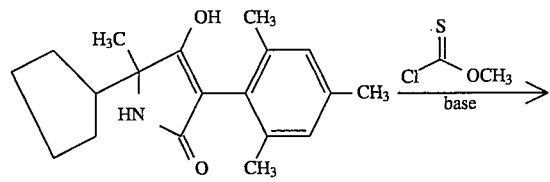

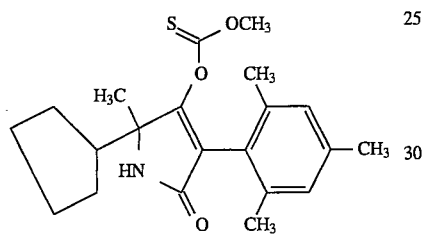

If, according to process ($D_\beta$), 3-(2,4,6-trimethylphenyl)-5-[(3-methyl)-cyclohexyl]-5-ethyl-pyrrolidn-2,4-dione, carbon disulphide and methyl iodide are used as starting components, the course of the reaction can be represented as follows:

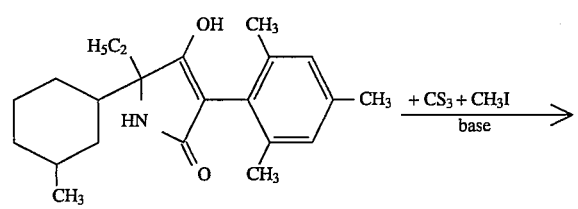

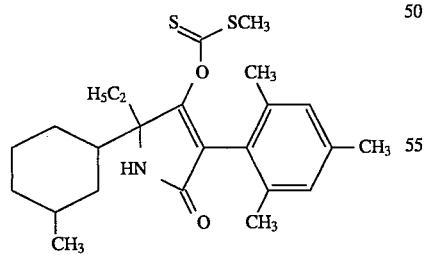

If, according to process (E), 3-(2,4,6-trimethylphenyl)-5-cyclohexyl-5-trifluoromethyl-pyrrolidine-2,4-dione and methanesulphonyl chloride are used as starting material, the course of the reaction can be represented by the following equation:

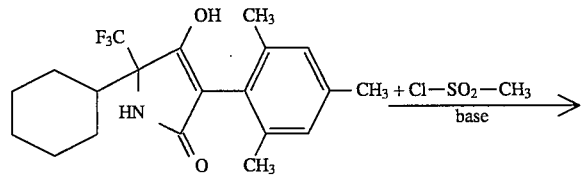

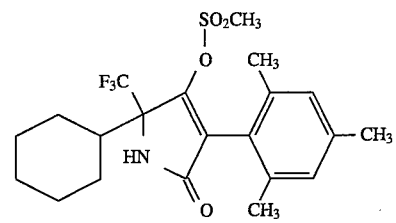

If, according to process (F), 3-(2,4-dimethylphenyl)-5-cyclopropyl-5-methyl-pyrrolidine-2,4-dione and 2,2,2-trifluoroethyl methanethio-chlorophosphonate are used as starting materials, the course of the reaction can be represented by the following equation:

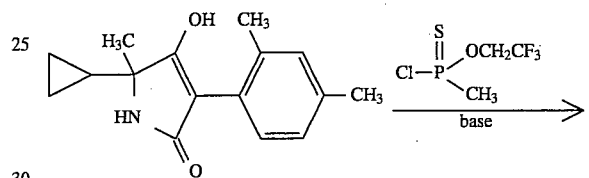

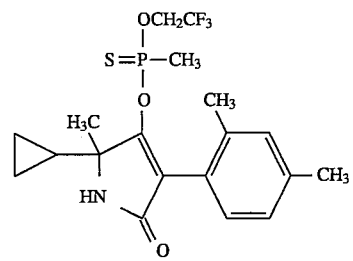

If, according to process (G), 3-(2,4,6-trimethylphenyl)-5-cyclohexyl-5-butyl-pyrrolidine-2,4-dione and NaOH are used as reactants, the course of the process according to the invention can be represented by the following equation:

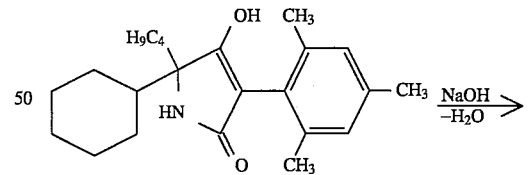

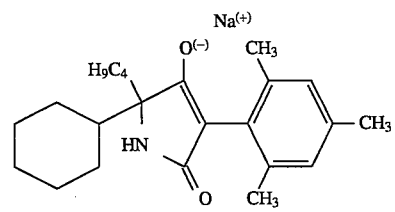

If, according to process ($H_\alpha$), 3-(2,4,6-trimethylphenyl)-5-[(4-methoxy)-cyclohexyl]-5-methyl-pyrrolidine-2,4-dione and ethyl isocyanate are used as starting materials, the course of the reaction can be represented by the following equation:

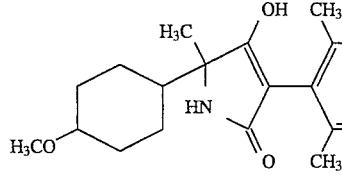 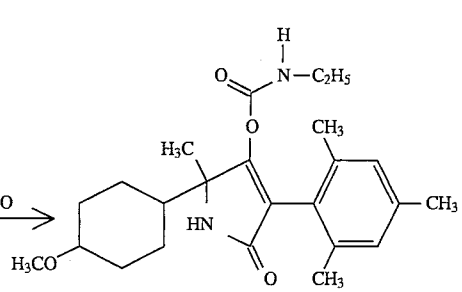

If, according to process (H$_\beta$), 3-(2,4,6-trimethylphenyl)-5-cyclopentyl-5-methyl-pyrrolidine-2,4-dione and dimethyl-carbamoyl chloride are used as starting materials, the course of the reaction can be represented by the following equation:

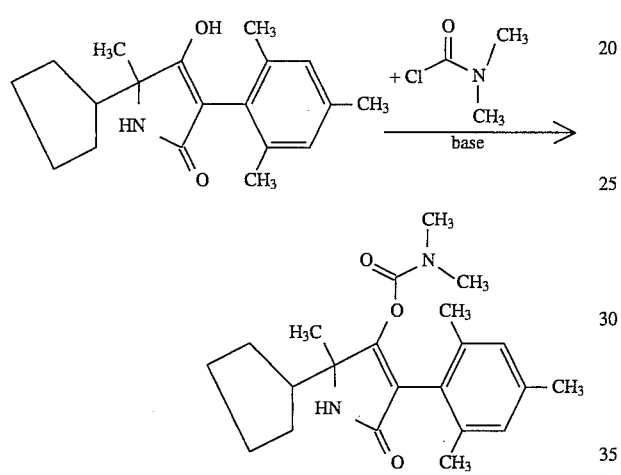

Some of the compounds of the formula (II)

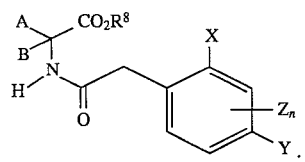

in which

A, B, X, Y, Z, n and R$^8$ have the abovementioned meaning, which are required as starting substances in process (A) according to the invention, are known and the subject of a patent application by the applicant company which has not been disclosed to date (P 42 36 400).

For example, acyl-amino acid esters of the formula (II) are obtained when amino acid derivatives of the formula (XIV)

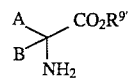

in which

R$^{9'}$ represents hydrogen (XIVa) and alkyl (XIVb) and A and B have the abovementioned meaning, are acylated with phenylacetyl halides of the formula

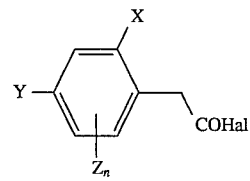

in which

X, Y, Z and n have the abovementioned meaning and

Hal represents chlorine or bromine, (Chem. Reviews 52, 237–416 (1953); Bhattacharya, Indien J. Chem. 6, 341–5, 1968) or when acylamino acids of the formula (IIa)

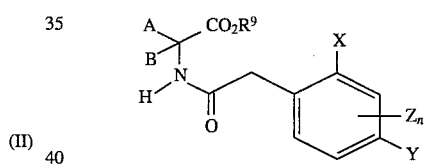

in which

A, B, X, Y, Z and n have the abovementioned meaning and

R$^9$ represents hydrogen, are esterified (them. Ind. (London) 1568 (1968)).

Furthermore, the starting substances of the formula (II)

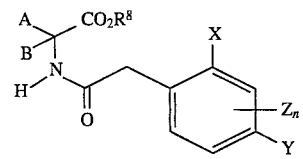

in which

A, B, X, Y, Z, n and R$^8$ have the abovementioned meaning, and which are used in the above process (A), can be prepared when aminonitriles of the formula (XVI)

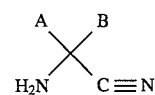

in which

A and B have the abovementioned meaning, are reacted with phenylacetyl halides of the formula (XV)

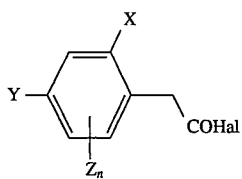

(XV)

in which

X, Y, Z and n have the abovementioned meaning and Hal represents chlorine or bromine, to give compounds of the formula (XVII)

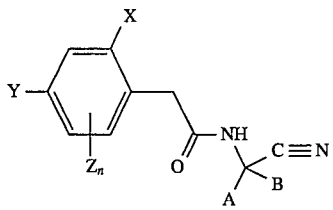

(XVII)

in which

A, B, X, Y, Z and n have the abovementioned meaning, which are subsequently subjected to alcoholysis in sulphuric acid.

Some of the compounds of the formula (XVII) are also known and the subject of a patent application by the applicant company which has not been disclosed to date (P 42 36 400).

The following compounds of the formula (II) may be mentioned by way of example, in addition to the intermediates mentioned in the Preparation Examples, but not by way of limitation:

N-(2,4-dichlorophenylacetyl)-2-cyclopropyl-alanine methyl ester,

N-(2,4-dichlorophenylacetyl)-2-cyclohexyl-alanine methyl ester,

N-(2,4-dichlorophenylacetyl)-2-cyclopropyl-alanine ethyl ester,

N-(2,4-dichlorophenylacetyl)-2-cyclohexyl-alanine ethyl ester,

N-(2,6-dichlorophenylacetyl)-2-cyclopropyl-alanine methyl ester,

N-(2,6-dichlorophenylacetyl)-2-cyclohexyl-alanine methyl ester,

N-(2,6-dichlorophenylacetyl)-2-cyclopropyl-alanine ethyl ester,

N-(2,6-dichlorophenylacetyl)-2-cyclohexyl-alanine ethyl ester,

N-(2-chloro-6-fluoro-phenyl-acetyl)-2-cyclopropyl-alanine methyl ester,

N-(2-chloro-6-fluorophenylacetyl)-2-cyclohexyl-alanine methyl ester,

N-(2-chloro-6-fluorophenylacetyl)-2-cyclopropyl-alanine ethyl ester,

N-(2-chloro-6-fluorophenylacetyl)-2-cyclohexyl-alanine ethyl ester,

N-(2,4,6-trimethylphenylacetyl)-2-cyclopropyl-alanine methyl ester,

N-(2,4,6-trimethylphenylacetyl)-2-cyclohexyl-alanine methyl ester,

N-(2,4,6-trimethylphenylacetyl)-2-cyclopropyl-alanine ethyl ester,

N-(2,4,6-trimethylphenylacetyl)-2-cyclohexyl-alanine ethyl ester,

N-(2,4-dimethylphenylacetyl)-2-cyclopropyl-alanine methyl ester,

N-(2,4-dimethylphenylacetyl)-2-cyclohexyl-alanine methyl ester,

N-(2,4-dimethylphenylacetyl)-2-cyclopropyl-alanine ethyl ester,

N-(2,4-dimethylphenylacetyl)-2-cyclohexyl-alanine ethyl ester,

Compounds of the formula (IIa) can be obtained, for example, from the phenylacetyl halides of the formula (XV) and amino acids of the formula (XIVa) by the method of Schotten-Baumann (Organikum [Laboratory Course in Organic Chemistry], 9th edition, 446 (1970) VEB Deutscher Verlag der Wissenschaften, Berlin).

The acid halides of the formula (III), carboxylic anhydrides of the formula (IV), chloroformic esters or chloroformic thioesters of the formula (V), chloromonothioformic esters or chlorodithioformic esters of the formula (VI), alkyl halides of the formula (VII), sulphonyl chlorides of the formula (VIII), phosphorus compounds of the formula (IX) and metal hydroxides or amines of the formula (X) and (XI) and isocyanates or carbamoyl chloride of the formula (XIII), all of which are furthermore required as starting substances for carrying out processes (B), (C), (D), (E), (F), (G) and (H) according to the invention, are generally known compounds of organic or inorganic chemistry.

Process (A) is characterized in that compounds of the formula (II), in which A, B, X, Y, Z, n and $R^8$ have the abovementioned meaning, are subjected to an intramolecular condensation reaction in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, iso-butanol and tert.-butanol.

Bases (deprotonating agents) which can be employed when carrying out process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, sodium carbonate, potassium carbonate and calcium carbonate, all of which can also be employed in the presence of phase transfer catalysts, such as, for example, triethylbenzylammonium chloride, tetrabutylammonium bromide, Adogen 464 or TDA 1[*]. Alkali metals such as sodium or potassium can furthermore be employed. Other substances which can be employed are alkali metal amides, alkali metal hydrides, alkaline earth metal amides and alkaline earth metal hydrides, such as sodium amide, sodium hydride and calcium hydride, moreover also alkali metal alcoholates, such as sodium methylate, sodium ethylate and potassium tert.-butylate.

[*] Adogen 464=methyltrialkyl ($C_8$–$C_{10}$) ammonium chloride
TDA 1=tris-(methoxyethoxyethyl)-amine When carrying out process (A) according to the invention, the reaction temperatures can be varied within a substantial range. In general, the process is carried out at temperatures between 0° C. and 250° C., preferably between 50° C. and 150° C.

In general, process (A) according to the invention is carried out under atmospheric pressure.

When carrying out process (A) according to the invention, the reactants of the formulae (II) and the deprotonating bases are generally employed in about twice the equimolar amounts. However, it is also possible to use the one or the other reactant in a larger excess (up to 3 mol).

Process (Bα) is characterized in that compounds of the formula (Ia) are reacted with carboxylic halides of the formula (III).

If the acid halides are used in process (Bα) according to the invention, then diluents which can be employed are all solvents which are inert towards these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylic esters, such as ethyl acetate, and also strongly polar solvents, such as dimethyl sulphoxide and sulpholane. If the acid halide is sufficiently stable to hydrolysis, the reaction can also be carried out in the presence of water.

If the corresponding carboxylic halides are used, then acid-binding agents which are suitable for the reaction in accordance with process (Bα) according to the invention are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

When carrying out process (Bα) according to the invention, the reaction temperatures can also be varied within a substantial range, which also applies if carboxylic halides are used. In general, the process is carried out at temperatures between −20° C. and +150° C., preferably between 0° C. and 100° C.

When carrying out process (Bα) according to the invention, the starting substances of the formula (Ia) and the carboxylic halide of the formula (III) are generally used in approximately equivalent amounts. However, it is also possible to employ the carboxylic halide in a larger excess (up to 5 mol). Working-up is carried out by customary methods.

Process (Bβ) is characterized in that compounds of the formula (Ia) are reacted with carboxylic anhydrides of the formula (IV).

If, in process (Bβ) according to the invention, carboxylic anhydrides are used as reactant of the formula (IV), then diluents which can preferably be used are those which are also preferably suitable when acid halides are used. Besides, a carboxylic anhydride employed in excess can also simultaneously act as the diluent.

When carrying Out process (Bβ) according to the invention, the reaction temperatures can be varied within a substantial range, which also applies if carboxylic anhydrides are used. In general, the process is carried out at temperatures between −20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Working-up is carried out by customary methods.

In general, a procedure is followed in which diluent and excess carbolyxic anhydride as well as the carboxylic acid which forms are removed by distillation or by washing with an organic solvent or with water. Process (C) is characterized in that compounds of the formula (Ia) are reacted with chloroformic esters or chloroformic thioesters of the formula (V).

If the corresponding chloroformic esters or chloroformic thioesters are used, then acid-binding agents in the reaction in accordance with process (C) according to the invention are all customary acid acceptors. The following can preferably be used: tertiary amines, such as triethylamine, pyridine, DABCO, DBU, DBA, Hünig base and N,N-dimethyl-aniline, furthermore alkaline earth metal oxides, such as magnesium oxide and calcium oxide, furthermore alkali metal carbonates and alkaline earth metal carbonates, such as sodium carbonate, potassium carbonate and calcium carbonate, and also alkali metal hydroxides, such as sodium hydroxide and potassium hydroxide.

If the chloroformic esters or chloroformic thioesters ere used, then diluents which can be employed in process (C) according to the invention are all solvents which are inert towards these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, furthermore ketones, such as acetone and methyl isopropyl ketone, moreover ethers, such as diethyl ether, tetrahydrofuran and dioxane, in addition carboxylic esters, such as ethyl acetate, and also strongly polar solvents, such as dimethyl sulphoxide and sulpholane.

If the chloroformic esters or chloroformic thioesters are used as carboxylic acid derivatives of the formula (V), then the reaction temperatures can be varied within a substantial range when carrying out process (C) according to the invention. If the process is carried out in the presence of a diluent and of an acid-binding agent, then the reaction temperatures are generally between −20° C. and 100° C., preferably between 0° C and 50° C.

Process (C) according to the invention is generally carried out under atmospheric pressure.

When carrying out process (C) according to the invention, the starting substances of the formula (Ia) and the chloroformic ester or chloroformic thioester of the formula (V) in question are generally used in approximately equivalent amounts. However, it is also possible to employ one or the other reactant in a larger excess (up to 2 mol). Working-up is then carried out by customary methods. In general, a procedure is followed in which precipitated salts are removed and the reaction mixture which remains is concentrated by stripping off the diluent.

In preparation process (D), approximately 1 mol of chloromonothioformic ester or chlorodithioformic ester of the formula (VI) is reacted at 0° to 120° C., preferably at 20° to 60° C., per mole of starting compound of the formula (Ia).

Suitable diluents which may be added are all inert polar organic solvents, such as ethers, amides, sulphones or sulphoxides.

Dimethyl sulphoxide, tetrahydrofuran, dimethylformamide and dimethyl sulphide are preferably employed.

If, in a preferred embodiment, the enolate salt of the compound Ia is prepared by adding strong deprotonating agents, such as, for example, sodium hydride or potassium tertiary butylate, the further addition of acid-binding agents can be dispensed with.

If acid-binding agents are employed, then suitable substances are customary inorganic or organic bases, sodium hydroxide, sodium carbonate, potassium carbonate, pyridine and triethylamine being mentioned by way of example.

The reaction can be carried out under atmospheric pressure or under increased pressure; it is preferably carried out under atmospheric pressure. Working-up is carried out by customary methods.

In preparation process ($D_\beta$), the equimolar amount, or an excess, of carbon disulphide is added per mole of starting compound of the formula (Ia). This process is preferably carried out at temperatures from 0° to 50° C. and, in particular, at 20° to 30° C.

Frequently, it is expedient to first prepare the corresponding salt from the compound of the formula (Ia) by adding a deprotonating agent (such as, for example, potassium tertiary butylate or sodium hydride). The compound (Ia) is reacted with carbon disulphide until the formation of the intermediate is complete, for example after stirring for several hours at room temperature.

The further reaction with the alkyl halide of the formula (VII) is preferably carried out at 0° to 70° C., in particular at 20+20 to 50° C. At least the equimolar amount of alkyl halide is employed.

The process is carried out under atmospheric pressure or under increased pressure, preferably under atmospheric pressure.

Again, working-up is carried out by customary methods.

In preparation process (E), approximately 1 mol of sulphonyl chloride (VIII) is reacted per mole of starting compound of the formula (Ia) at −20° to 150° C., preferably at 0° to 70° C.

Suitable diluents which may be added are all inert polar organic solvents, such as ethers, amides, nitriles, sulphones, sulphoxides or halogenated hydrocarbons, such as methylene chloride.

Dimethyl sulphoxide, tetrahydrofuran, dimethylformamide, dimethyl sulphide and methylen chloride are preferably employed.

If, in a preferred embodiment, the enolate salt of the compound Ia is prepared by adding strong deprotonating agents (such as, for example, sodium hydride or potassium tertiary butylate), the further addition of acid-binding agents can be dispensed with.

If acid-binding agents are employed, then suitable substances are customary inorganic or organic bases, sodium hydroxide, sodium carbonate, potassium carbonate, pyridine and triethylamine being mentioned by way of example.

The reaction can be carried out under atmospheric pressure or under increased pressure, it is preferably carried out under atmospheric pressure. Working-up is carried out by customary methods.

To obtain compounds of the structure (Ie) 1 to 2, preferably 1 to 1.3 mol of the phosphorus compound of the formula (IX) are reacted in preparation process (F) per mole of the compound (Ia) at temperatures between −40° C. and 150° C., preferably between −10° and 110° C.

Suitable diluents which my be added are all inert, polar organic solvents, such as ethers, amides, nitriles, alcohols, sulphides, sulphones, sulphoxides and the like.

Acetonitrile, dimethyl sulphoxide, tetrahydrofuran, dimethylformamide or methylene chloride are preferably employed.

Suitable acid-binding agents which may be added are customary inorganic or organic bases, such as hydroxides or carbonates. Examples which may be mentioned are sodium hydroxide, sodium carbonate, potassium carbonate, pyridine and triethylamine.

The reaction can be carried out under atmospheric pressure or under increased pressure, it is preferably carried out under atmospheric pressure. Working-up is carried out by customary methods of organic chemistry. The end products obtained are preferably purified by crystallization, chromatography or by so-called "incipient distillation", i.e. removal of the volatile components in vacuo.

Process (G) is characterized in that compounds of the formula (Ia) are reacted with metal hydroxides (X) or amines (XI).

Diluents which can be employed in the process according to the invention are, preferably, ethers, such as tetrahydrofuran, dioxane or diethyl ether, or else alcohols, such as methanol, ethanol, isopropanol, but also water. Process (G) according to the invention is preferably carried out under atmospheric pressure. The reaction temperatures are generally between −20° C. and 100° C., preferably between 0° C. and 50° C.

In preparation process ($H_\alpha$), approximately 1 mol of isocyanate, or isothiocyanate, of the formula (XII) is reacted per mole of starting compound of the formula (Ia) at 0° to 100° C., preferably at 20° to 50° C.

Suitable diluents which may be added are all inert organic solvents, such as ethers, amides, nitriles, sulphones or sulphoxides.

If appropriate, catalysts may be added to accelerate the reaction. Catalysts which are very advantageously employed are organotin compounds, such as, for example, dibutyltin dilaurate. The process is preferably carried out under atmospheric pressure.

In preparation process ($H_\beta$), approximately 1 mol of carbamoyl chloride of the formula (XIII) is reacted per mole of starting compound of the formula (Ia) at 0° to 150° C., preferably at 20° to 70° C.

Suitable diluents which may be added are all inert polar organic solvents, such as ethers, amides, sulphones or sulphoxides.

Dimethyl sulphoxide, tetrahydrofuran, dimethylformamide or methylene chloride are preferably employed.

If, in a preferred embodiment, the enolate salt of the compound (Ia) is prepared by adding strong deprotonating agents (such as, for example, sodium hydride or potassium tertiary butylate), the further addition of acid-binding agents can be dispensed with.

If acid-binding agents are employed, then suitable substances are customary inorganic or organic bases, sodium hydroxide, sodium carbonate, potassium carbonate, triethylamine or pyridine being mentioned by way of example.

The reaction can be carried out under atmospheric pressure or under increased pressure, it is preferably carried out under atmospheric pressure. Working-up is carried out by customary methods.

The active compounds are suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The abovementioned pests include:

From the order of the Isopoda, for example, *Oniscus asellus, Armadillidium vulgare* and *Porcellio scaber.*

From the order of the Diplopoda, for example, *Blaniulus guttulatus* From the order of the Chilopoda, for example, *Geophilus carpophagus* and *Scutigera spec.* From the order of the Symphyla, for example, *Scutigerella immaculata.*

From the order of the Thysanura, for example, *Lepisma saccharina*. From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria* migratorioides, *Melanoplus differentialis* and *Schistocerca gregaria*.

From the order of the Dermaptera, for example, *Forficula auricularia*. From the order of the Isoptera, for example, Reticulitermes spp.

From the order of the Anoplura, for example, *Phylloxera vastatrix*, Pemphigus spp., *Pediculus humanus* corporis, Haematopinus spp. and Linognathus spp. From the order of the Mallophaga, for example, Trichodectes spp. and Damalinea spp. From the order of the Thysanoptera, for example, *Hercinohrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum*, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., Trichoplusia ni, *Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Hylotrupes byjulus, Agelastica alni, Leptinotarsa decemlineata, Phaedon cochleariae*, Diabrotica spp., *Psylliodes chrysocephala, Epilachna varivestis*, Atomaria spp., Oryzaephilus surinamensis, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp. From the order of the Arachnida, for example, *Scorpio maurus* and *Latrodectus mactans*.

From the order of the Acarina, for example, Acarus siro, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention are not only active against plant, hygiene and stored product pests, but also, in the veterinary medicine sector, against animal parasites (ectoparasites and endoparasites), such as scaly ticks, Argasidae, scab mites, Trombidae, flies (stinging and sucking), parasitic fly larvae, lice, hair lice, bird lice, fleas and endoparasitic worms. For example, they show an outstanding activity against *Lucilia cuprina* larvae.

The active compounds according to the invention are distinguished by a powerful insecticidal and acaricidal activity.

They can be employed particularly successfully for combating plant-injurious mites, such as, for example, against the greenhouse red spider mite (*Tetranychus urticae*).

The active compounds according to the invention also have a leaf-acting insecticidal activity.

The active compounds according to the invention can also be also used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The active compounds according to the invention are highly suitable for selectively combating monocotyledon weeds in dicotyledon cultures either pre- or post-emergence. For example, they can be used very successfully for combating swedes in soya beans or sugar beet. The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2dimethylpropyl)-1,3,5-triazine-2,4(1H, 3H)-dione (AMETHYDIONE) or N-(2-benzothiazolyl)-N,N'-dimethylurea (METABENZTHIAZURON) for combating weeds in cereals; 4-amino- 3-methyl-6-phenyl-1,2,4-triazin-5-(4H)-one (METAMITRON) for combating weeds in sugar beet, and 4-amino-6-(1,1-dimethylethyl)-3-methylthio-1,2,4-triazin-5(4H)-one (METRIBUZIN) for combating weeds in soya beans. Other suitable herbicides are 2,4-dichlorophenoxyacetic acid (2,4-D); 4-(2,4-dichlorophenoxy) butyric acid (2,4-DB); 2,4-dichlorophenoxypropionic acid (2,4-DP); 3-isopropyl-2, 1, 3-benzothiadiazin-4-one-2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CLORSULFURON); 2-[4-(2,4-dichlorophenoxy)-phenoxy]propionic acid, its methyl or its ethyl ester (DICLOFOPMETHYL); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl or its ethyl ester (FENOXAPROP); [(4-amino-3,5-dichloro-6-fluoro-2-pyridinyl)-oxy]-acetic acid or its 1-methylheptyl ester (FLUROXYPYR); methyl 2-[4,5-dihydro-4-methyl-4-(1-methylethyl)-5-oxo-1H- imidazol-2-yl]-4 (5) -methylbenzoate (IMAZAMETHABENZ); 3,5-diiodo-4-hydroxybenzonitrile (IOXYNIL); N,N-dimethyl-N'-(4-isopropylphenyl)urea (ISOPROTURON); (2-methyl-4-chlorophenoxy) acetic acid (MCPA); (4-chloro-2-methylphenoxy)-propionic acid (MCPP); N-methyl-2-(1,3-benzothiazol-2-yloxy) acetanilide (MEFENACET); 2-{[ [((4-methoxy-6-methyl-1,3,5-triazin-2-yl)-amino)-carbonyl]-amino]-sulphonyl}-benzoic acid or its methylester (METSULFURON); N-(1-ethylpropyl)-3,4-dimethyl-2,6-dinitroaniline (PENDIMETHALIN); 0-(6-chloro- 3-phenyl-pyridazin-4-yl) S-octyl thiocarbonate (PYRIDATE); 4-ethylamino-2-t-butylamino-6-methylthio-s-triazine (TERBUTRYNE); and 3-[[[[(4-methoxy-6-methyl-1,3,5-triazin-2-yl)-amino]-carbonyl]-amino]-sulphonyl]thiophene-2-carboxylic acid (THIAMETURON). Surprisingly, some mixtures also show synergistic action.

Mixtures with i other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds accord-

PREPARATION EXAMPLES

Example (Ia-1)

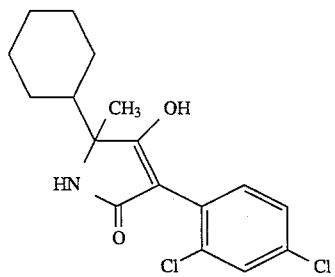

55.5 g (0.493 mol) of potassium tert.-butylate are heated at reflux temperature in 150 ml of absolute tetrahydrofuran. 83.4 g (0.224 tool) of N-(2,4-dichlorophenylacetyl) 2-cyclohexyl-alanine methyl ester in 450 ml of absolute toluene are added dropwise and the mixture is refluxed for 90 minutes. After the reaction has ended, the batch is brought to room temperature, and 720 ml of water are added. The aqueous phase is separated off, and the toluene phase is extracted using 340 ml of water. The combined aqueous phases are washed with toluene and subsequently treated with 75 ml of concentrated hydrochloric acid at room temperature. The crude product which has precipitated is filtered off with suction, washed and dried.

53.10 g (70% of theory) of 3-(2,4-dichlorophenyl)-5-cyclohexyl-5-methylpyrrolidine-2,4-dione of melting point m.p. 196°–198° C. are obtained.

The end products of the formula (Ia) which are listed below in Table 8 are obtained analogously to Example (Ia-1) and following the general information which can be found in the description for the processes according to the invention:

TABLE 8

| Ex. No.: | A | B | X | Y | $Z_n$ | Phylical constant [°C.] |
|---|---|---|---|---|---|---|
| (Ia-2) | △ | $CH_3$ | Cl | Cl | H | m.p.: 150 |
| (Ia-3) | △ | $CH_3$ | $CH_3$ | $CH_3$ | 6-$CH_3$ | m.p.: >220 |
| (Ia-4) | cyclohexyl | $CH_3$ | $CH_3$ | $CH_3$ | 6-$CH_3$ | m.p.: 223–225 |
| (Ia-5) | △ | $CH_3$ | $CH_3$ | $CH_3$ | H | m.p.: 172–173 |

(formula Ia shown above table)

Example (Ib-1)

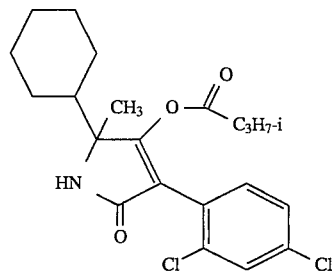

5.1 g (0.015 mol) of 3-(2,4-dichlorophenyl)-5-cyclohexyl-5-methyl-pyrrolidine-2,4-dione are suspended in 70 ml of absolute dichloromethane and treated with 2.1 ml of triethylamine. 1.58 ml of isobutyryl chloride in 5 ml of absolute dichloromethane are added at 0°–10° C. The end of the reaction is determined by thin-layer chromatography. The mixture is subsequently washed twice using in each case 100 ml of 0.5N sodium hydroxide solution and the organic phase is dried over magnesium sulphate. The residue obtained after evaporation of the solvent is recrystallized from ether/n-hexane 1:5.

4.4 g (72% of theory) of 3-(2,4-dichlorophenyl)-5-cyclohexyl-5-methyl-4-isobutyroxy-Δ3-pyrolin-2-one of melting point m.p. 138°–140° C. are obtained.

The end products of the formula (I-b) which are listed below in Table 9 are obtained analogously to Example (Ib-1) and following the general information for the processes according to the invention:

TABLE 9

(I-b)

| Ex. No.: | A | B | X | Y | $Z_n$ | R1 | Physical constant [°C.] |
|---|---|---|---|---|---|---|---|
| (Ib-2) | △ | $CH_3$ | Cl | Cl | H | $CH_3$ | 174–176 |
| (Ib-3) | △ | $CH_3$ | Cl | Cl | H | $i\text{-}C_3H_7$ | 180 |
| (Ib-4) | △ | $CH_3$ | Cl | Cl | H | $t\text{-}C_4H_9$ | 175 |
| (Ib-5) | △ | $CH_3$ | $CH_3$ | $CH_3$ | $6\text{-}CH_3$ | $CH_3$ | 209 |
| (Ib-6) | △ | $CH_3$ | $CH_3$ | $CH_3$ | $6\text{-}CH_3$ | $i\text{-}C_3H_7$ | 166–167 |
| (Ib-7) | ⬡ | $CH_3$ | Cl | Cl | H | $CH_3$ | 181–183 |
| (Ib-8) | ⬡ | $CH_3$ | Cl | Cl | H | $t\text{-}C_4H_9$ | 161–163 |
| (Ib-9) | ⬡ | $CH_3$ | $CH_3$ | $CH_3$ | $6\text{-}CH_3$ | $CH_3$ | 233–237 |
| (Ib-10) | ⬡ | $CH_3$ | $CH_3$ | $CH_3$ | $6\text{-}CH_3$ | $i\text{-}C_3H_7$ | 182–184 |
| (Ib-11) | △ | $CH_3$ | $CH_3$ | $CH_3$ | H | $CH_3$ | 155 |
| (Ib-12) | △ | $CH_3$ | $CH_3$ | $CH_3$ | H | $i\text{-}C_3H_7$ | 153 |
| (Ib-13) | △ | $CH_3$ | $CH_3$ | $CH_3$ | H | $t\text{-}C_4H_9$ | 133–135 |

Example (Ic-1)

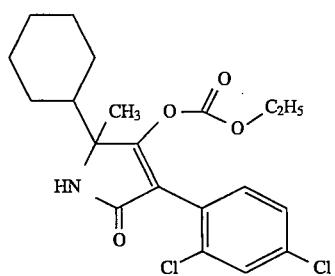

5.1 g (0.015 mol) of 3-(2,4-dichlorophenyl)-5-cyclohexyl-5-methyl-pyrrolidine-2,4-dione are suspended in 70 ml of absolute dichloromethane and the mixture is treated with 2.1 ml of triethylamine. 1.5 ml of ethyl chloroformate in 5 ml of absolute dichloromethane are added at 0°–10° C., and stirring of the batch is continued at room temperature. The end of the reaction is determined by thin-layer chromatography. The mixture is then washed twice using in each case 100 ml of 0.5N sodium hydroxide solution, and the organic phase is dried over magnesium sulphate. The residue obtained after evaporation of the solvent is recrystallized from ether/n-hexane (1:5).

4.6 g (74% of theory) of O-ethyl O-[3-(2,4-dichlorophenyl)-5-cyclohexyl-5-methyl-Δ3-pyrolin-4-yl-2-one] carbonate of melting point m.p. 175°–176° C. are obtained.

The end products of the formula (Ic) which are listed below in Table 10 are obtained analogously to Example (Ic-1) and following the general information for the processes according to the invention:

TABLE 10

(I-c)

| Ex. No. | A | B | X | Y | $Z_n$ | L | M | $R^2$ | m.p. °C. |
|---|---|---|---|---|---|---|---|---|---|
| (Ic-2) |  | $CH_3$ | Cl | Cl | H | O | O | $C_2H_5$ | 140 |
| (Ic-3) |  | $CH_3$ | Cl | Cl | H | O | O | s-$C_4H_9$ | 127 |
| (Ic-4) |  | $CH_3$ | $CH_3$ | $CH_3$ | 6-$CH_3$ | O | O | $C_2H_5$ | 143 |
| (Ic-5) |  | $CH_3$ | $CH_3$ | $CH_3$ | 6-$CH_3$ | O | O | s-$C_4H_9$ | 156–157 |
| (Ic-6) |  | $CH_3$ | Cl | Cl | H | O | O | s-$C_4H_9$ | 162–163 |
| (Ic-7) |  | $CH_3$ | $CH_3$ | $CH_3$ | 6-$CH_3$ | O | O | $C_2H_5$ | 218–219 |
| (Ic-8) |  | $CH_3$ | $CH_3$ | $CH_3$ | 6-$CH_3$ | O | O | s-$C_4H_9$ | 201 |
| (Ic-9) |  | $CH_3$ | $CH_3$ | $CH_3$ | 6-$CH_3$ | O | S | i-$C_3H_7$ | 133–135 |
| (Ic-10) |  | $CH_3$ | $CH_3$ | $CH_3$ | H | O | O | $C_2H_5$ | 155 |
| (Ic-11) |  | $CH_3$ | $CH_3$ | $CH_3$ | H | O | O | s-$C_4H_9$ | 65 |

Example (Ie-1)

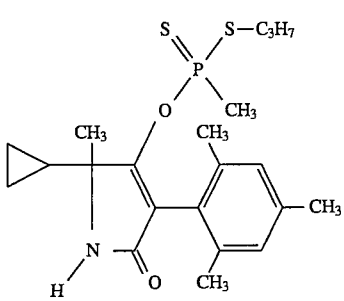

(Ie-1)

3g (11 mmol) of 3-(2,4,6-trimethylphenyl)-5-cyclopropyl-5-methyl-pyrrolidine-2,4-dione are suspended in 20 ml of absolute tetrahydrofurane and the mixture is treated with 1.7 ml of triethylamine. 2.2 g of methyl-propylmercaptothiophosphonic acid chloride are added, then the mixture is stirred at 50° C. for 24 hours. The residue obtained after evaporation of the solvent is chromatographed on silica gel using n-hexane/acetone 9/1 as eluent. 1.7 g (37% of theory) of the compound of the formula (Ie-1) of melting point m.p. 143° C. are obtained.

Example (Ie-2)

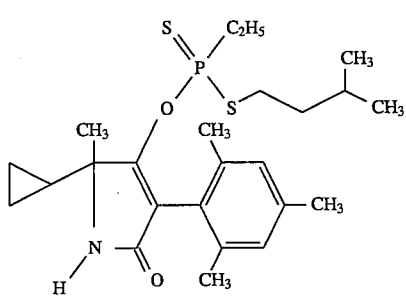

(Ie-2)

Analogously the compound of formula (Ie-2) of melting point m.p. 100° C. is obtained.

Example (Ig-1)

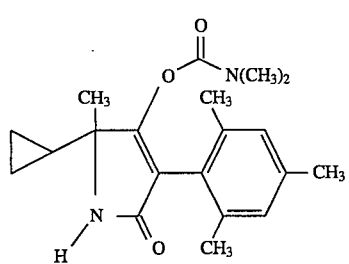

(Ig-1)

4.86 g (0.02 mol) of 3-(2,4,6-trimethylphenyl)-5-cyclopropyl-5-methyl-pyrrolidine-2,4,-dione are suspended in 70 ml of absolute tetrahydrofurane and the mixture is treated with 2.8 ml of triethylamine. 1.84 ml of dimethylcarbamoyl chloride and 20 mg of 4-N,N-dimethylaminopyridine in 5 ml of absolute tetrahydrofurane are added at 0°–10° C. The reaction mixture is refluxed and the end of the reaction is determined by thin-layer chromatography. The residue obtained after evaporation of the solvent is dissolved in CH$_2$Cl$_2$, washed twice using 0.5N sodium hydroxide solution, the organic phase is dried over magnesium sulphate and the solvent is stripped off in vacuo. 3.1 g (45% of theory) of 4-dimethylcarbamoyloxy-5-cyclopropyl-5-methyl-3-(2,4,6-trimethylphenyl)-Δ3-pyrroline-2-one of melting point m.p. 201°–205° C. are obtained.

Example (Ig-2)

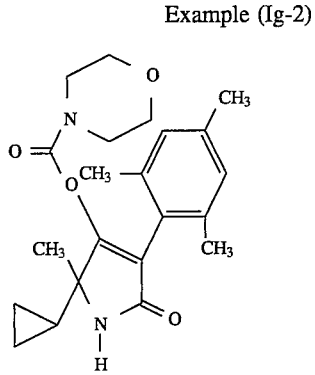

(Ig-2)

Analogously to Example (Ig-1) 4-morpholinocarbamoyloxy-5-cyclopropyl-5-methyl-3-(2,4,6-trimethylphenyl)-Δ3-pyrroline-2-one of melting point m.p. 137°–141° C. are obtained.

Preparation of the starting compounds

Example (II-1)

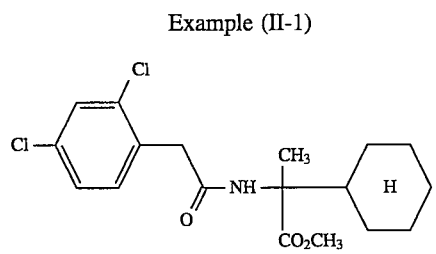

(II-1)

89.2 g (0.263 mol) of N-(1-cyano-1-methyl-cyclohexylmethyl)-2-(2,4-dichlorophenyl)-acetamide, dissolved in 270 ml of dichloromethane, are added dropwise with stirring and ice-cooling to 128 g (1.31 mol) of concentrated sulphuric acid, during which process the temperature of the reaction mixture rises to 40° C., and, after the addition has ended, stirring is continued for 2 hours at 40° C. until the dichloromethane phase of the reaction mixture has become colourless. 184 ml of absolute methanol are subsequently added dropwise with ice-cooling, during which process the temperature of the reaction mixture rises to 40° C., and stirring is continued for 6 hours at 40°–50° C. For working-up, the reaction mixture is poured into 1500 g of ice, with stirring, and the mixture is extracted using dichloromethane, the combined organic phases are washed using aqueous sodium hydrogencarbonate solution until free from acid and dried over magnesium sulphate, and the solvent is removed in vacuo.

83.6 g (85% of theory) of N-(2,4-dichlorophenyl-acetyl)-2-cyclohexyl-alanine methyl ester of melting point m.p. 107°–108° C. are obtained.

Example (II-2)

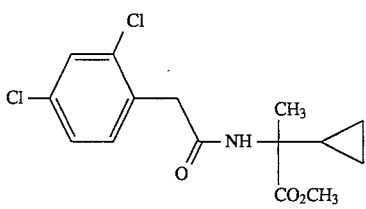

Analogously to Example (II-1), N-(2,4-dichlorophenylacetyl)-2-cyclopropyl-alanine methyl ester of melting point m.p. 81° C. is obtained.

Use Examples

In the Use Examples which follow, the compounds listed below were employed as comparison substances:

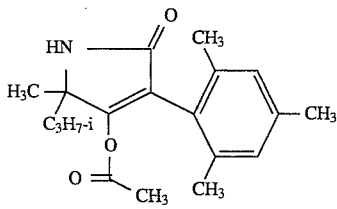

(A)

3-(2,4,6-Trimethylphenyl)-5-methyl-5-isopropyl-4-acetoxy-Δ3-pyrrolin-2-one, disclosed in EP 456,063.

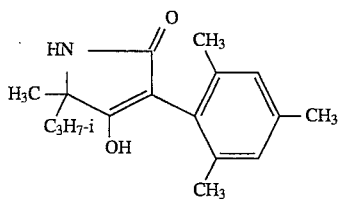

(B)

3-(2,4,6-Trimethylphenyl)-5-methyl-5-isopropyl-pyrrolidine-2,4-dione, disclosed in EP 456,063.

Use Example

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, the following results were obtained at an exemplary application rate of 125 g/ha, the active compounds being tolerated well to very well by sugar-beets:

| Plant | % Activity | Compound of Preparation Example No. |
|---|---|---|
| Digitaria | ≧80 | Ia-3, Ib-5, Ib-6, Ic-4 |
| Alopeccurus | ≧80 | Ia-3, Ib-5, Ib-6, Ic-4 |
| Lolium | ≧90 | Ia-3, Ib-5, Ib-6, Ic-4 |

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area.

After three weeks, the degree of damage to the plants is rated in % damage in comparison to the development of the untreated control. The figures denote:

0%=no action (like untreated control)

100%=total destruction

In this test the following results were obtained at an exemplary application rate of 125 g/ha, the active compounds being tolerated well to very well by soya beans:

| Plant | % Activity | Compound of Preparation Example No. |
|---|---|---|
| Cynodon | 30 | Ia-2, Ia-3, Ib-2, Ib-3, Ib-5, Ib-6, Ic-3, Ic-4 |
| Echinochia | 80 | Ia-2, Ia-3, Ib-2, Ib-3, Ib-5, Ib-6, Ic-3, Ic-4 |
| Sataria | 80 | Ia-2, Ia-3, Ib-2, Ib-3, Ib-5, Ib-6, Ic-3, Ic-4 |

Example C

Tetranychus test (OP-resistant)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested with all development stages of the greenhouse red spider mite or two-spotted spider mite (Tetranychus urticae) are treated by being dipped into the active compound preparation of the desired concentration.

After the desired time, the destruction is determined in %. 100% means that all spider mites have been destroyed; 0% means that no spider mites have been destroyed.

In this test, a destruction of 100% was shown after 7 days, for example, by the compound of the Preparation Example (Ic-3) at an exemplary active compound concentration of 0.02%.

Example: D

Blowfly larvae test

Test animals: Lucili cuprina larvae

Emulsifier: 35 parts by weight of ethylene glycol monomethyl ether 35 parts by weight of nonylphenol polyglycol ether To produce a suitable preparation of active compound, three parts by weight of active compound are mixed with seven parts by weight of the abovementioned mixture and the resulting emulsion concentrate is diluted with water to the particular desired concentration.

About 20 Lucilia cuprina res. larvae are introduced into a test tube which contains approx. 1 cm³ of horse meat and 0.5 ml of the preparation of active compound. After 24 hours, the activity of the preparation of active compound is determined. 100% means that all blowfly larvae have been destroyed; 0% means that no blowfly larvae have been destroyed.

In this test, a destruction of 100% was shown, for example, by compound (Ia-3) of the Preparation Examples at an exemplary active compound concentration of 300 ppm.

We claim:

1. A 1-H-3[P]-phenyl-5-cycloalkylpyrrolidine-2,4-dione [s] of the formula [(I)]

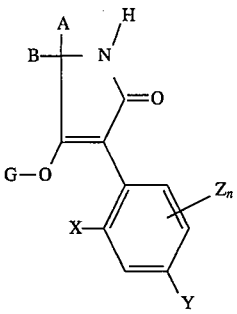

in which
A represents optionally substituted cycloalkyl and
B represents optionally substituted alkyl,
X represents alkyl, halogen or alkoxy,
Y represents hydrogen, alkyl, halogen, alkoxy or halogenoalkyl,
Z represents alkyl, halogen or alkoxy,
n represents a number 0, 1, 2 or 3,
G represents hydrogen (a) or the groups

 (b)

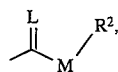 (c)

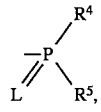 (e)

or

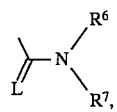 (g)

L and M represent oxygen and/or sulphur,
$R^1$ represents in each case optionally halogen-substituted alkyl, alkenyl, alkoxyalkyl, alkylthioalkyl, polyalkoxyalkyl or cycloalkyl, wherein said cycloalkyl group is optionally interrupted by hetero atoms, or represents optionally substituted phenyl, optionally substitute phenylalkyl, substituted hetaryl, substituted phenoxyalkyl or substituted hetaryloxyalkyl,
$R^2$ represents in each case optionally halogen-substituted alkyl, alkenyl, alkoxyalkyl, polyalkoxyalkyl or in each case optionally substituted cycloalkyl, phenyl or benzyl,
$R^4$ and $R^5$ independently of one another represent in each case optionally halogen-substituted alkyl, alkoxy, cycloalkyloxy, alkylamino, dialkylamino, alkylthio, alkenylthio or cycloalkylthio and in each case optionally substituted phenyl, phenoxy, benzyloxy or phenylthio,
$R^6$ and $R^7$ independently of one another represent hydrogen, in each case optionally halogen-substituted alkyl, alkenyl, alkoxy or alkoxyalkyl, optionally substituted phenyl, optionally substituted benzyl, or together with the N-atom to which they are bound represent a cycle which is optionally interrupted by oxygen or sulphur.

2. A 1-H-3-phenyl-5-cycloalkylpyrrolidine-2,4-dione according to claim 1, of the formula

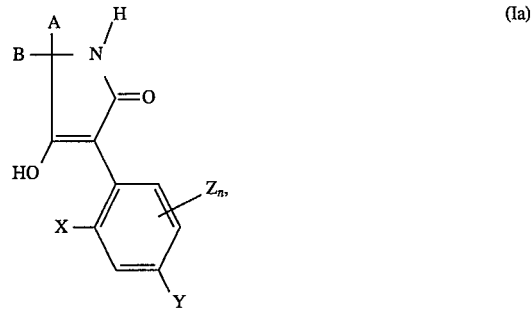 (Ia)

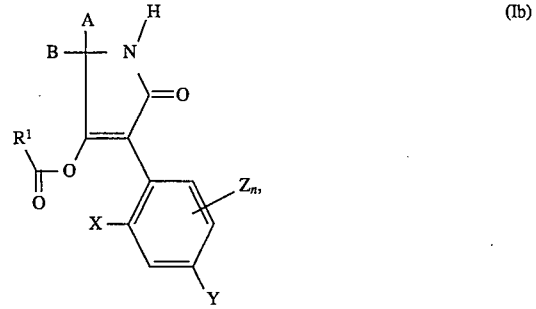 (Ib)

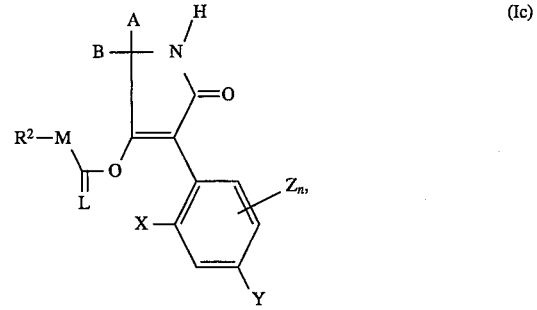 (Ic)

in which
A, B, L, M, X, Y, $Z_n$, $R^1$ and $R^2$ having the meanings given in claim 1.

3. A 1-H-3-Phenyl-5-cycloalkylpyrrolidine-2,4-dione according to claim 1, in which
A represents $C_3$–$C_{10}$-cycloalkyl which is optionally substituted by halogen, $C_1$–$C_6$-alkyl, $C_1$–$C_6$-alkoxy, $C_1$–$C_4$-halogenoalkyl or $C_1$–$C_4$-halogenoalkoxy, B represents hydrogen or optionally halogen-substituted straight-chain or branched alkyl, X represents $C_1$–$C_6$-alkyl, halogen or $C_1$–$C_6$-alkoxy, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, G represents hydrogen (a) or the groups

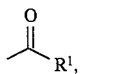 (b)

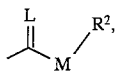 (c)

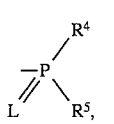 (e)

or

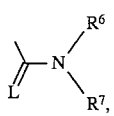 (g)

in which

L and M in each case represent oxygen and/or sulphur, $R^1$ represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_2$–$C_8$-alkyl or cycloalkyl having 3 to 8 ring atoms, which is optionally interrupted by oxygen and/or sulphur atoms, or represents phenyl which is optionally substituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, or represents hetaryl which is optionally substituted by halogen and/or $C_1$–$C_6$-alkyl, or represents phenoxy-$C_1$–$C_6$-alkyl which is optionally substituted by halogen and/or $C_1$–$C_6$-alkyl, or represents hetaryloxy-$C_1$–$C_6$-alkyl which is optionally substituted by halogen, amino and/or $C_1$–$C_6$-alkyl, $R^2$ represents in each case optionally halogen-substituted $C_1$–$C_{20}$-alkyl, $C_3$–$C_{20}$-alkenyl, $C_1$–$C_8$-alkoxy-$C_2$–$C_8$-alkyl or $C_1$–$C_8$-polyalkoxy-$C_2$–$C_8$-alkyl, or represents $C_3$–$C_8$-cycloalkyl which is optionally substituted by halogen, $C_1$–$C_6$-alkyl, $C_1$–$C_6$-alkoxy and/or $C_1$–$C_6$-alkylthio, or represents phenyl or benzyl, each of which is optionally substituted by halogen, nitro, $C_1$–$C_6$-alkyl, $C_1$–$C_6$-alkoxy or $C_1$–$C_6$-halogenoalkyl-, $R^4$ and $R^5$ independently of one another represent in each case optionally halogen-substituted $C_1$–$C_8$-alkyl, $C_1$–$C_8$-alkoxy, $C_3$–$C_7$-cycloalkyloxy, $C_1$–$C_8$-alkylamino, di-($C_1$–$C_8$)-alkylamino, $C_1$–$C_8$-alkylthio, $C_3$–$C_8$-alkenylthio or $C_3$–$C_7$-cycloalkylthio, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl and $R^6$ and $R^7$ independently of one another represent hydrogen or represent in each case halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-alkyl, $C_1$–$C_8$-halogenoalkyl or $C_1$–$C_8$-alkoxy, or together with the nitrogen atom to which they are bound represent a ring having 3–6 C-atoms which is optionally interrupted by oxygen or sulphur.

4. A 1-H-3-phenyl-5-cycloalkylpyrrolidine-2,4-dione according to claim 1, in which A represents $C_3$–$C_8$-cycloalkyl which is optionally substituted by fluorine, chlorine, $C_1$–$C_5$-alkyl, $C_1$–$C_5$-alkoxy, $C_1$–$C_2$-halogenoalkyl or $C_1$–$C_2$-halogenoalkoxy, B represents hydrogen or straight-chain or branched $C_1$–$C_6$-alkyl which is optionally substituted by chlorine or fluorine, X represents $C_1$–$C_4$-alkyl, halogen or $C_1$–$C_4$-alkoxy, Y represents hydrogen, $C_1$–$C_4$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy;

G represents hydrogen (a) or the groups

 (b)

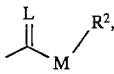 (c)

 (e)

or

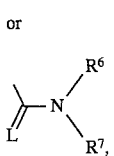 (g)

in which

L and M in each case represent oxygen and/or sulphur, $R^1$ represents in each case optionally halogen-substituted $C_1$–$C_{16}$-alkyl, $C_2$–$C_{16}$-alkenyl, $C_1$–$C_6$-alkoxy-$C_1$–$C_6$-alkyl, $C_1$–$C_{16}$-alkylthio-$C_1$–$C_6$-alkyl, $C_1$–$C_6$-polyalkoxy-$C_2$–$C_6$-alkyl or cycloalkyl having 3 to 7 ring atoms which can be interrupted by 1–2 oxygen and/or sulphur atoms, or represents phenyl which is optionally substituted by halogen, nitro, $C_1$–$C_4$-alkyl, $C_1$–$C_4$-alkoxy, $C_1$–$C_3$-halogenoalkyl, $C_1$–$C_3$-halogenoalkoxy $C_1$–$C_6$-alkylthio or $C_1$–$C_6$-alkylsulphonyl, or represents phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, or represents hetaryl which is optionally substituted by fluorine, chlorine, bromine and/or $C_1$–$C_4$-alkyl, or represents phenoxy-$C_1$–$C_5$-alkyl which is optionally substituted by fluorine, chlorine, bromine, amino and/or $C_1$–$C_4$-alkyl, or represents hetaryloxy-$C_1$–$C_5$-alkyl which is optionally substituted by fluorine, chlorine, bromine, amino and/or $C_1$–$C_4$-alkyl, $R^2$ represents in each case optionally halogen-substituted $C_1$–$C_{16}$-alkyl, $C_3$–$C_{16}$-alkenyl, $C_1$–$C_6$-alkoxy-$C_2$–$C_6$-alkyl or $C_1$–$C_6$-polyalkoxy-$C_2$–$C_6$-alkyl, or represents $C_3$–$C_7$-cycloalkyl which is optionally substituted by halogen, $C_1$–$C_4$-alkyl, $C_1$–$C_4$-alkoxy and/or $C_1$–$C_4$-alkylthio, or represents phenyl or benzyl, each of which is optionally substituted by halogen, nitro, $C_1$–$C_6$-alkyl, $C_1$–$C_3$-alkoxy or $C_1$–$C_3$-halogenoalkyl, $R^4$ and $R^5$ independently of one another represent in each case optionally halogen-substituted $C_1$–$C_6$-alkyl, $C_1$–$C_6$-alkoxy, $C_3$–$C_6$-cycloalkyloxy, $C_1$–$C_6$-alkylamino, di-($C_1$–$C_6$-alkyl)amino, $C_1$–$C_6$-alkylthio, $C_3$–$C_6$-alkenylthio or $C_3$–$C_6$-cycloalkylthio, or represent phenyl, phenoxy, benzyloxy, or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl and $R^6$ and $R^7$ independently of one another represent hydrogen, or represent in each case optionally halogen-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together with the N-atom to which they are bound represent a ring having 3–6 C-atoms which is optionally substituted by oxygen or sulphur.

5. A 1-H-3-phenyl-5-cycloalkylpyrrolidine-2,4-dione according to claim 1, in which A represents $C_3$–$C_6$-cycloalkyl which is optionally substituted by fluorine, methyl, ethyl, propyl, i-propyl, butyl, i-butyl, s-butyl, methoxy, ethoxy, propoxy, i-propoxy, trifluoromethyl or trifluoromethoxy, t-butyl, B represents hydrogen or methyl, ethyl, propyl, i-propyl, butyl, i-butyl, s-butyl or t-butyl, each of which is optionally substituted by fluorine, X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or tri-fluoromethyl, Z represents methyl, ethyl, propyl, butyl, i-butyl, tert.-butyl, fluorine, chlorine, bromine, methoxy or ethoxy, i-propyl, G represents hydrogen (a) or the groups

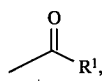 (b)

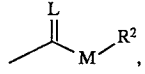 (c)

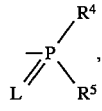 (e)

E  (f)

or

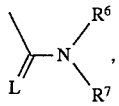 (g)

in which

L and M represent oxygen and/or sulphur, $R^1$ represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_2$–$C_4$-alkyl or cyaloalkyl having 3 to 6 ring atoms which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy, nitro, methylthio, ethylthio, methylsulphonyl or ethylsulphonyl, or represents phenyl-$C_1$–$C_3$-alkyl which is optionally substituted by fluorine, chlorine, bromine, methyl, ethyl, propyl, i-propyl, methoxy, ethoxy, trifluoromethyl or trifluoromethoxy, or represents furanoyl, thienyl, pyridyl, pyrimidyl, thiazolyl and pyrazolyl, each of which is optionally substituted by fluorine, chlorine, bromine, methyl or ethyl, or represents phenoxy-$C_1$–$C_4$-alkyl which is optionally substituted by fluorine, chlorine, methyl or ethyl, or represents pyridyloxy-$C_1$–$C_4$-alkyl, pyrimidyloxy-$C_1$–$C_4$-alkyl and thiazolyloxy-$C_1$–$C_4$-alkyl, each of which is optionally substituted by fluorine, chlorine, amino, methyl or ethyl, $R^2$ represents $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, each of which is optionally substituted by fluorine or chlorine, or represents $C_3$–$C_6$-cycloalkyl which is optionally substituted by fluorine, chlorine, methyl, ethyl, propyl, methoxy, ethoxy, methylthio or ethylthio, or represents phenyl or benzyl, each of which is optionally substituted by fluorine, chlorine, nitro, methyl, ethyl, propyl, i-propyl, methoxy, ethoxy or trifluoromethyl, $R^4$ and $R^5$ independently of one another represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, each of which is optionally substituted by fluorine or chlorine, or represent phenyl, phenoxy, benzyloxy or phenylthio, each of which is optionally substituted by fluorine, chlorine, bromine, nitro, cyano, $C_1$–$C_2$-alkoxy, $C_1$–$C_4$-fluoroalkoxy, $C_1$–$C_2$-alkylthio, $C_1$–$C_2$-fluoroalkylthio or $C_1$–$C_3$-alkyl and $R^6$ and $R^7$ independently of one another represent hydrogen, or represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine, chlorine or bromine, or represent phenyl which is optionally substituted by fluorine, chlorine, bromine, $C_1$–$C_4$-halogenoalkyl, $C_1$–$C_4$-alkyl or $C_1$–$C_4$-alkoxy, or represent benzyl which is optionally substituted by fluorine, chlorine, bromine, $C_1$–$C_4$-alkyl, $C_1$–$C_4$-halogenoalkyl or $C_1$–$C_4$-alkoxy, or together with the N-atom to which they are bound represent a ring having 4–6 C-atoms which is optionally substituted by oxygen or sulphur.

6. A pesticidal or herbicidal composition comprising an effective amount of a 1-H-3-phenyl-5-cycloalkylpyrrolidine-2,4-dione according to claim 1 and an inert carrier.

7. A method of combating pests, wherein a 1-H-3-phenyl-5-cycloalkylpyrrolidine-2,4-dione according to claim 1 is allowed to act on pests, undesired plants and/or their environment.

8. A compound according to claim 1, which has the formula

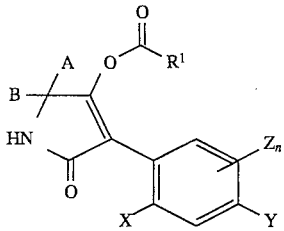
(Ib)

in which

A represents $C_3$–$C_{10}$ cycloalkyl,

B represents $C_1$–$C_6$ alkyl,

X represents $C_1$–$C_4$ alkyl or halogen;

Y represents hydrogen, $C_1$–$C_4$ alkyl or halogen,

Z represents $C_1$–$C_4$ alkyl or halogen, or $R^1$ represents $C_1$–$C_{14}$ alkyl.

9. A compound according to claim 1, which has the formula

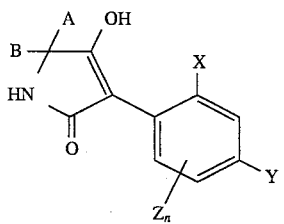
(Ia)

in which

A represents $C_3$–$C_{10}$ cycloalkyl,

B represents $C_1$–$C_6$ alkyl,

X represents halogen,

Y represents halogen,

Z represents hydrogen.

10. A compound according to claim 1, which has the formula

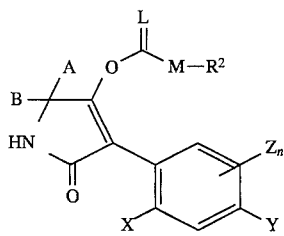
(Ic)

in which

A represents $C_3$–$C_{10}$ cycloalkyl,

B represents $C_1$–$C_6$ alkyl,

X represents halogen,

Y represents halogen,

Z represents hydrogen, and $C_1$–$C_4$ alkyl and $R^2$ represents $C_1$–$C_{14}$ alkyl.

11. A compound according to claim 1, which has the formula

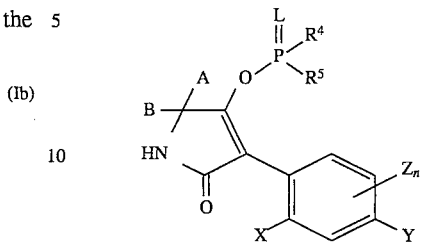
(Ie)

in which

A represents $C_3$–$C_{10}$ cycloalkyl,

B represents $C_1$–$C_6$ alkyl,

L represents S or O,

X represents $C_1$–$C_4$ alkyl,

Y represents $C_1$–$C_4$ alkyl,

Z represents hydrogen, $R^4$ represents $C_1$–$C_4$ alkyl, and $R^5$ represents $C_1$–$C_4$ alkoxy or $C_1$–$C_4$ alkylthio.

12. A compound according to claim 1, wherein $R^1$ and $R^2$ represent $C_1$–$C_{14}$ alkyl, $C_3$–$C_7$ cycloalkyl, phenyl or benzyl.

13. A compound according to claim 10, wherein L is oxygen.

14. A compound according to claim 10, which has the following formula

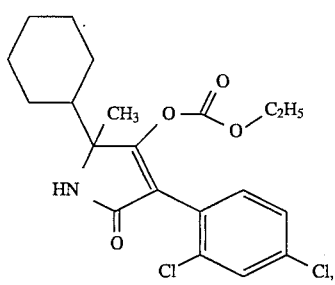

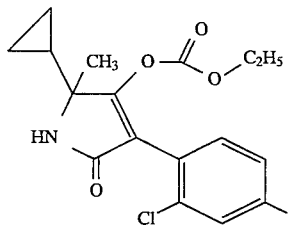
and

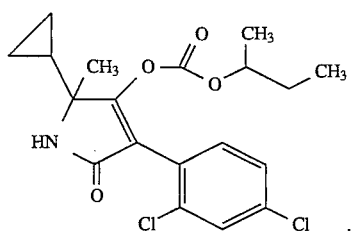

15. A compound according to claim 9, which as the formula
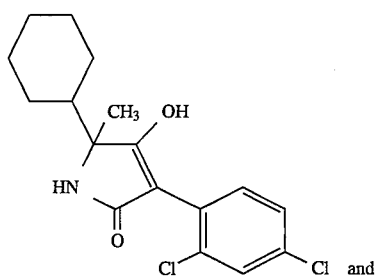 and
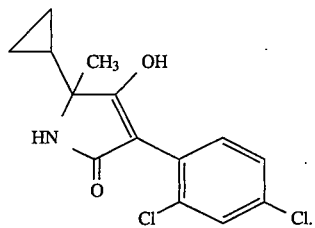
16. A compound according to claim 8, which has the formula
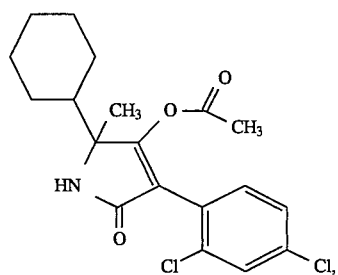
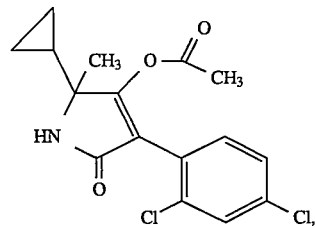
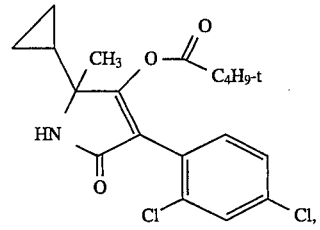
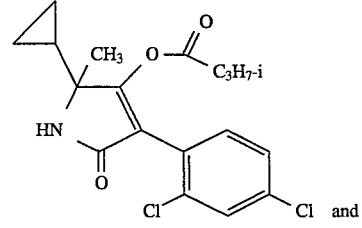 and
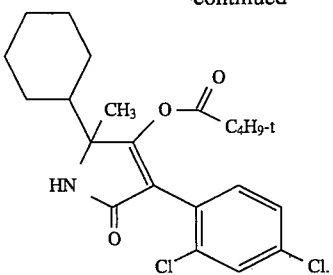
17. A compound according to claim 11, which has the formula
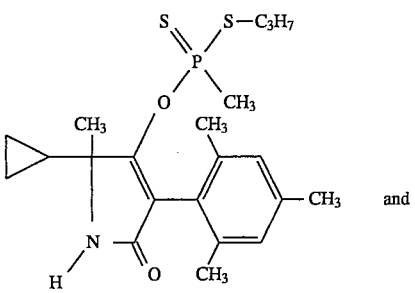 and
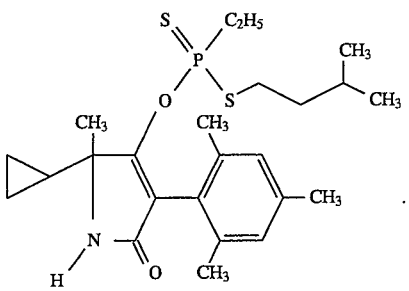
18. A compound according to claim 10, which has the formula
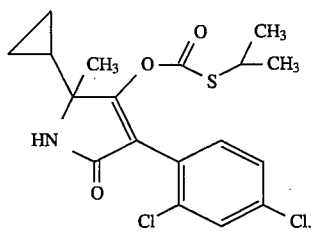
19. A compound according to claim 1, which has the formula
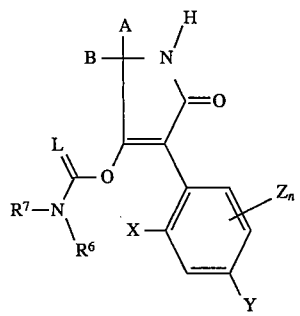

in which

A represents $C_3$–$C_{10}$ cycloallyl,

B represents $C_1$–$C_6$ allyl,

X represents H or $C_1$–$C_4$ alkyl,

Y represents H or $C_1$–$C_4$ allyl, $R^6$ and $R^7$ independently of one another represent hydrogen, or represent in each case optionally halogen-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, or represent phenyl which is optionally substituted by halogen, $C_1$–$C_5$-halogenoalkyl, $C_1$–$C_5$-alkyl or $C_1$–$C_5$-alkoxy, or represent benzyl which is optionally substituted by halogen, $C_1$–$C_5$-alkyl, $C_1$–$C_5$-halogenoalkyl or $C_1$–$C_5$-alkoxy, or together represent morpholine.

20. A compound according to claim 19, which has the formula

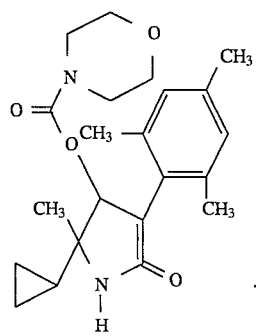

UNITED STATES PATENT AND TRADEMARK OFFICE
CERTIFICATE OF CORRECTION

PATENT NO. : 5,567,671  Page 1 of 3
DATED : October 22, 1996
INVENTOR(S) : Reiner Fischer, et al.

It is certified that error appears in the above-identified patent and that said Letters Patent is hereby corrected as shown below:

| | |
|---|---|
| Title Page, [57], Abstract Line 1 | Delete "1-H-3-phenyl-5-cyloalkyl" and substitute -- 1-H-3-phenyl-5-cycloalkyl-- |
| Col. 107, Line 19 | Delete "[P]" |
| Col. 107, Line 20 | Delete "[s]" and "[ (I) ]" |
| Col. 111, Line 64 | Delete "E (f) " |
| Col. 117, Line 2 | Delete "$C_3$ -$C_{10}$-cycloallyl" and substitute --$C_3$ -$C_{10}$-cycloalkyl-- |
| Col. 117, Line 3 | Delete "$C_1$ -$C_6$-allyl" and substitute --$C_1$ -$C_6$ -alkyl-- |
| Col. 117, Line 5 | Delete "$C_1$ -$C_4$ -allyl" and substitute --$C_1$ -$C_4$ -alkyl-- |

UNITED STATES PATENT AND TRADEMARK OFFICE
CERTIFICATE OF CORRECTION

PATENT NO. : 5,567,671

DATED : October 22, 1996

INVENTOR(S) : Reiner Fischer, et al.

It is certified that error appears in the above-identified patent and that said Letters Patent is hereby corrected as shown below:

Col. 118, Lines 3-14        Delete

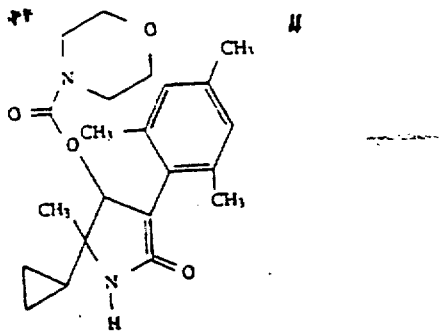

UNITED STATES PATENT AND TRADEMARK OFFICE
CERTIFICATE OF CORRECTION

PATENT NO. : 5,567,671
DATED : October 22, 1996
INVENTOR(S): Reiner Fischer, et al.

It is certified that error appears in the above-identified patent and that said Letters Patent is hereby corrected as shown below:

and substitute -- 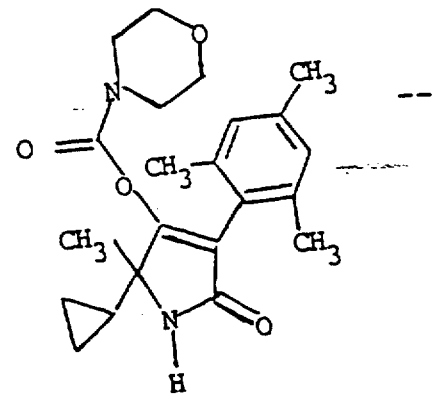 --

Signed and Sealed this

Fourth Day of January, 2000

Attest:

Attesting Officer

Acting Commissioner of Patents and Trademarks